US007671073B2

(12) United States Patent
Duffy et al.

(10) Patent No.: US 7,671,073 B2
(45) Date of Patent: Mar. 2, 2010

(54) CYCLOHEXYLALANINE DERIVATIVES AS DIPEPTIDYL PEPTIDASE-IV INHIBITORS FOR THE TREATMENT OR PREVENTION OF DIABETES

(75) Inventors: Joseph L. Duffy, Cranford, NJ (US); David E. Kaelin, Jr., East Brunswick, NJ (US); Ann E. Weber, Scotch Plains, NJ (US); Brian A Kirk, Sudbury, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 656 days.

(21) Appl. No.: 11/579,265

(22) PCT Filed: May 13, 2005

(86) PCT No.: PCT/US2005/016825

§ 371 (c)(1),
(2), (4) Date: Nov. 1, 2006

(87) PCT Pub. No.: WO2005/116029

PCT Pub. Date: Dec. 8, 2005

(65) Prior Publication Data

US 2008/0027093 A1 Jan. 31, 2008

Related U.S. Application Data

(60) Provisional application No. 60/572,065, filed on May 18, 2004.

(51) Int. Cl.
*A61K 31/44* (2006.01)
*A61K 31/41* (2006.01)
*A61K 31/42* (2006.01)
*A61K 31/415* (2006.01)
*A61K 31/40* (2006.01)
*C07D 401/10* (2006.01)
*C07D 271/06* (2006.01)
*C07D 263/24* (2006.01)
*C07D 249/16* (2006.01)

(52) U.S. Cl. .................. 514/343; 514/357; 514/383; 514/364; 514/376; 514/392; 514/423; 548/131; 548/227; 548/262.4; 548/538; 546/208; 546/279.1

(58) Field of Classification Search ............... 548/131, 548/229, 262.4, 538; 546/208, 279.1; 514/343, 514/357, 383, 364, 376, 392, 423
See application file for complete search history.

(56) References Cited

U.S. PATENT DOCUMENTS

| 5,939,560 | A | 8/1999 | Jenkins et al. |
| 6,011,155 | A | 1/2000 | Villhauer et al. |
| 6,166,063 | A | 12/2000 | Villhauer et al. |
| 6,303,661 | B1 | 10/2001 | Demuth et al. |
| 6,432,969 | B1 | 8/2002 | Villhauer |
| 6,699,871 | B2 | 3/2004 | Edmondson et al. |

FOREIGN PATENT DOCUMENTS

| WO | WO 97/40832 A1 | 11/1997 |
| WO | WO 98/19998 A2 | 5/1998 |
| WO | WO 98/19998 A3 | 5/1998 |
| WO | WO 00/34241 | 6/2000 |
| WO | WO 01/34594 A1 | 5/2001 |
| WO | WO 01/96295 A2 | 12/2001 |
| WO | WO 02/02560 A2 | 1/2002 |
| WO | WO 02/076450 A1 | 10/2002 |
| WO | WO 03/000180 A2 | 1/2003 |
| WO | WO 03/000180 A3 | 1/2003 |
| WO | WO 03/000181 A2 | 1/2003 |
| WO | WO 03/082817 A2 | 10/2003 |
| WO | WO 2004/007468 A1 | 1/2004 |
| WO | WO 2004/032836 A2 | 4/2004 |
| WO | WO 2004/043940 A1 | 5/2004 |
| WO | WO 2004/050022 A2 | 6/2004 |
| WO | WO 2004/058266 | 7/2004 |
| WO | WO 2004/064778 A2 | 8/2004 |
| WO | WO 2004/069162 A2 | 8/2004 |
| WO | WO 2004/110436 A1 | 12/2004 |
| WO | WO 2004/112701 A2 | 12/2004 |
| WO | WO 2004/112701 A3 | 12/2004 |

(Continued)

OTHER PUBLICATIONS

Caldwell, C.G., et al., "Fluoropyrrolidine amides as dipeptidyl peptidase IV inhibitors" Bioorganic & Medicinal Chemistry Letters, vol. 14, pp. 1265-1268, 2004.
Edmondson, S.D., et al., "Potent and selective proline derived dipeptidyl peptidase IV inhibitors" Bioorganic & Medicinal Chemistry Letters, vol. 14, pp. 5151-5155, 2004.
Holst, J.J., "Treatment of Type 2 diabetes mellitus with agonist of the GLP-1 receptor or DPP-IV inhibitors" Expert Opin. Emerg. Drugs, vol. 9, pp. 155-166, 2004.
Deacon C.F., et al., "Inhibitors of dipeptidyl peptidase IV: a novel approach for the prevention and treatment of Type 2 diabetes?" Expert Opin. Investig. Drugs, vol. 13, pp. 1091-1102, 2004.
Augustyns, K., et al., "Dipeptidyl peptidase IV inhibitors as new therapeutic agents for the treatment of Type 2 diabetes" Expert Opin. Ther. Patents, vol. 13, pp. 499-510, 2003.

(Continued)

*Primary Examiner*—Rebecca L Anderson
(74) *Attorney, Agent, or Firm*—Philippe L. Durette; Catherine D. Fitch

(57) ABSTRACT

The present invention is directed to novel cyclohexylalanine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

16 Claims, No Drawings

FOREIGN PATENT DOCUMENTS

| | | |
|---|---|---|
| WO | WO 2005/011581 A2 | 2/2005 |
| WO | WO 2005/044195 A2 | 5/2005 |
| WO | WO 2005/056003 A1 | 6/2005 |
| WO | WO 2005/056013 A1 | 6/2005 |
| WO | WO 2005/108382 A1 | 11/2005 |
| WO | WO 2005/116029 A1 | 12/2005 |
| WO | WO 2005/123685 A1 | 12/2005 |
| WO | WO 2006/009886 A1 | 1/2006 |
| WO | WO 2006/023750 A2 | 3/2006 |

OTHER PUBLICATIONS

"Novel N-substituted-2-cyanopyrrolidines as potent inhibitors of dipeptidyl peptidase IV in the treatment of non-insulin-dependent diabetes mellitus" Exp. Opin. Ther. Patents, vol. 10, pp. 1937-1942, 2000.

Vahl, T.P., et al., "Gut peptides in the treatment of diabetes mellitus" Expert Opin. Investig. Drugs, vol. 13, pp. 177-188, 2004.

Holst, J.J., et al., "Glucagon-like peptide 1 and inhibitors of dipeptidyl peptidase IV in the treatment of type 2 diabetes melitus" Current Opinion in Pharmacology, vol. 4, pp. 589-596, 2004.

Augustyns, K., et al., "Inhibitors of proline-specific dipeptidyl peptidases: DPP IV inhibitors as a novel approach for the treatment of Type 2 diabetes" Expert Opin. Ther Patents, vol. 15, pp. 1387-1407, 2005.

Knudsen, L.B., "Glucagon-like Peptide-1: The Basis of a New Class of Treatment for Type 2 Diabetes" J. Med. Chem., vol. 47, pp. 4128-4134, 2004.

Drucker, D.J., "Therapeutic potential of dipeptidyl peptidase IV inhibitors for the treatment of type 2 diabetes" Expert Opin. Investig. Drugs, vol. 12, pp. 87-100, 2003.

Xu, J., et al., "Discovery of potent and selective phenylalanine based dipeptidyl peptidase IV inhibitors" Bioorganic & Medicinal Chemistry Letters, vol. 15, pp. 2533-2536, 2005.

Weber, A.E., "Dipeptidyl Peptidase IV Inhibitors for the Treatment of Diabetes" J. Med. Chem., vol. 47, pp. 4135-4141, 2004.

Demuth, H.U., et al., "Type 2 diabetes—Therapy with dipeptidyl peptidase IV inhibitors" Biochimica et Biophysica Acta, vol. 1751, pp. 33-44, 2005.

CYCLOHEXYLALANINE DERIVATIVES AS DIPEPTIDYL PEPTIDASE-IV INHIBITORS FOR THE TREATMENT OR PREVENTION OF DIABETES

CROSS REFERENCE TO RELATED APPLICATIONS

This application is the National Stage of International Application No. PCT/US2005/016825, filed 13 May 2005, which claims the benefit under 35 U.S.C. 119(e) of U.S. Provisional Application No. 60/572,065, filed 18 May 2004.

FIELD OF THE INVENTION

The present invention relates to novel cyclohexylamine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic ☐ cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensitization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, Bioorg. Med. Chem. Lett., 6: 1163-1166 (1996); and *Bioorg. Med. Chem. Lett.* 6: 2745-2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-IV inhibitors have not been studied extensively to date, especially for utilities other than diabetes. New compounds are needed so that improved DP-IV inhibitors can be found for the treatment of diabetes and potentially other diseases and conditions. The therapeutic potential of DP-IV inhibitors for the treatment of type 2 diabetes is discussed by D. J. Drucker in *Exp. Opin. Invest. Drugs*, 12: 87-100 (2003) and by K. Augustyns, et al., in *Exp. Opin. Ther. Patents*, 13: 499-510 (2003).

SUMMARY OF THE INVENTION

The present invention is directed to novel cyclohexylalanine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to novel cyclohexylalanine derivatives useful as inhibitors of dipeptidyl peptidase-IV. Compounds of the present invention are described by structural formula I:

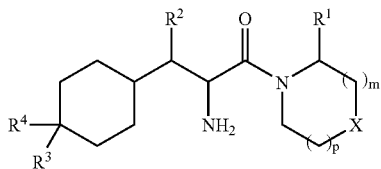

I or a pharmaceutically acceptable salt thereof; wherein each n is independently 0, 1, or 2;

m and p are independently 0 or 1;

X is $CH_2$, S, CHF or $CF_2$;

$R^1$ is hydrogen or cyano;

$R^2$ is selected from the group consisting of $C_{1-10}$ alkyl, wherein alkyl is unsubstituted or substituted with one to five substituents independently selected from halogen or hydroxy, $C_{2-10}$ alkenyl, wherein alkenyl is unsubstituted or substituted with one to five substituents independently selected from halogen or hydroxy, $(CH_2)_n$-aryl, wherein aryl is unsubstituted or substituted with one to five substituents independently selected hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, $(CH_2)_n$-heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, $(CH_2)_n-C_{3-6}$ cycloalkyl, wherein cycloalkyl is unsubstituted or substituted with one to three substituents independently selected from halogen, hydroxy, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, $(CH_2)_n COOH$, $(CH_2)_n COOC_{1-6}$ alkyl, $(CH_2)_n CONR^5R^6$, wherein $R^5$ and $R^6$ are independently selected from the group consisting of hydrogen, tetrazolyl, thiazolyl, $(CH_2)_n$-phenyl, $(CH_2)_n-C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or $R^5$ and $R^6$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and wherein any individual methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;

each $R^3$ is independently selected from the group consisting of halogen, cyano, hydroxy, phenyloxy, unsubstituted or substituted with one to five substituents independently selected from halogen, hydroxy, $CO_2H$, $CONR^5R^6$, cyano, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens;

$C_{1-6}$ alkyl, wherein alkyl is unsubstituted or substituted with one to five halogens, $C_{1-6}$ alkoxy, wherein alkoxy is unsubstituted or substituted with one to five halogens, $(CH_2)_n-NR^5R^6$, $(CH_2)_n-CONR^5R^6$, $(CH_2)_n-OCONR^5R^6$, $(CH_2)_n-SO_2NR^5R^6$, $(CH_2)_n-SO_2R^7$, $(CH_2)_n-NR^8SO_2R^7$, $(CH_2)_n-NR^8CONR^5R^6$, $(CH_2)_n-NR^8COR^8$, $(CH_2)_n-NR^8CO_2R^7$, $(CH_2)_n-COOH$, $(CH_2)_n$—$COOC_{1-6}$ alkyl, $(CH_2)_n$-aryl, wherein aryl is unsubstituted or substituted with one to five substituents independently selected from halogen, hydroxy, $CO_2H$,
  $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $CO_2H$, $C_{1-6}$ alkyloxycarbonyl, aryl, $C_{1-6}$ alkyl, $C_{3-6}$ cycloalkyl, and $C_{1-6}$ alkoxy, wherein aryl, alkyl and alkoxy are unsubstituted or substituted with one to five halogens, $(CH_2)_n$-heterocyclyl, wherein heterocyclyl is unsubstituted or substituted with one to three substituents independently selected from oxo, hydroxy, halogen, $CO_2H$, $C_{1-6}$ alkyloxycarbonyl, aryl, $C_{1-6}$ alkyl, $C_{3-6}$ cycloalkyl, and $C_{1-6}$ alkoxy, wherein aryl, alkyl and alkoxy are unsubstituted or substituted with one to five halogens, $(CH_2)_n$—$C_{3-6}$ cycloalkyl, wherein cycloalkyl is unsubstituted or substituted with one to three substituents independently selected from halogen, hydroxy, aryl, $C_{1-6}$ alkyl, and $C_{1-6}$ alkoxy, wherein aryl, alkyl and alkoxy are unsubstituted or substituted with one to five halogens, wherein any individual methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;

$R^4$ is selected from the group consisting of:
  hydrogen,
  hydroxy,
  halogen,
  cyano,
  $C_{1-6}$ alkyl, wherein alkyl is unsubstituted or substituted with one to five halogens, and
  $C_{1-6}$ alkoxy, wherein alkoxy is unsubstituted or substituted with one to five halogens;

$R^5$ and $R^6$ are each independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or $R^5$ and $R^6$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens;

$R^7$ is independently selected from the group consisting of $(CH_2)_n$-heteroaryl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein heteroaryl, phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens; and each $R^8$ is hydrogen or $R^7$.

In one embodiment of the compounds of the present invention, the carbon atom marked with an * has the stereochemical configuration as depicted in formula Ia

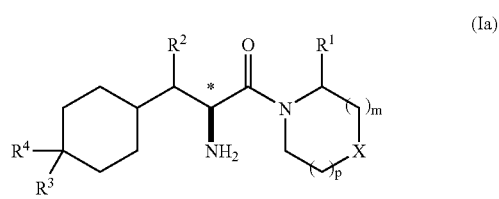

(Ia)

wherein X, m, p, $R^1$, $R^2$, $R^3$, and $R^4$ are as defined herein.

In a class of this embodiment of the compounds of the present invention, the carbon atom marked with an * and the carbon atom attached to $R^1$ and marked with an ** have the stereochemical configurations as depicted in formula Ib:

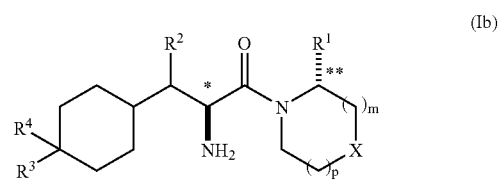

(Ib)

wherein X, m, p, $R^1$, $R^2$, $R^3$, and $R^4$ are as defined herein.

In a second class of this embodiment of the compounds of the present invention, the carbon atom marked with an *, the carbon atom attached to $R^1$ and marked with an , and the carbon atom attached to $R^2$ and marked with an * have the stereochemical configurations as depicted in formula Ic:

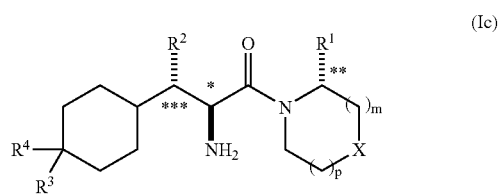

(Ic)

wherein X, m, p, $R^1$, $R^2$, $R^3$, and $R^4$ are as defined herein.

In a second embodiment of the compounds of the present invention, m is 1 and p is 0 as depicted in formula Id:

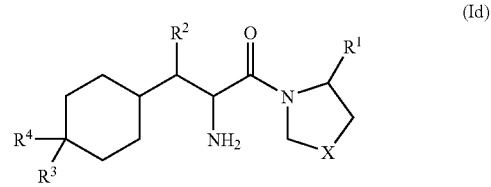

(Id)

wherein X, $R^1$, $R^2$, $R^3$, and $R^4$ are as defined herein.

In a class of this embodiment of the compounds of the present invention, the carbon atom marked with an * and the carbon atom attached to $R^1$ and marked with an ** have the stereochemical configurations as depicted in formula Ie:

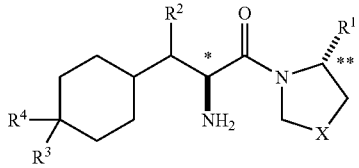

wherein X, $R^1$, $R^2$, $R^3$, and $R^4$ are as defined herein.

In a subclass of this class of this embodiment of the compounds of the present invention, the carbon atom marked with an *, the carbon atom attached to $R^1$ and marked with an , and the carbon atom attached to $R^2$ and marked with an * have the stereochemical configuration as depicted in formula If:

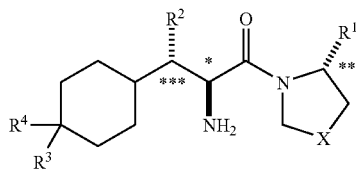

wherein X, $R^1$, $R^2$, $R^3$, and $R^4$ are as defined herein.

In a subclass of this subclass, $R^1$ is hydrogen; $R^4$ is hydrogen or hydroxy; and X is CHF or $CF_2$.

In a fourth embodiment of the compounds of the present invention, $R^2$ is selected from the group consisting of
$C_{1-3}$ alkyl, wherein alkyl is unsubstituted or substituted with one to five substituents independently selected from halogen or hydroxy,
$CH_2$—$C_{3-6}$ cycloalkyl,
COOH,
COOC$_{1-6}$ alkyl, and
CONR$^5$R$^6$, wherein $R^5$ and $R^6$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^5$ and $R^6$ together with the nitrogen atom to which they are attached form a heterocyclic ring selected from pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

In a class of this embodiment, $R^2$ is selected from the group consisting of:
methyl,
ethyl,
$CH_2$-cyclopropyl,
COOH,
COOMe,
COOEt,
CONMe$_2$,
CONH$_2$,
CONHMe,
CONHEt,
pyrrolidin-1-ylcarbonyl,
azetidin-1-ylcarbonyl, and
[(tetrazol-5-yl)amino]carbonyl.

In a fifth embodiment of the compounds of the present invention, $R^3$ is selected from the group consisting of:
phenyloxy, unsubstituted or substituted with one to five substituents independently selected from halogen, hydroxy, CONR$^5$R$^6$, cyano,
$C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens;
NR$^5$R$^6$,
CONR$^5$R$^6$,
OCONR$^5$R$^6$,
NR$^8$SO$_2$R$^7$,
NR$^8$CONR$^5$R$^6$,
NR$^8$COR$^8$,
NR$^8$CO$_2$R$^7$,
$(CH_2)_n$—COOC$_{1-6}$ alkyl,
aryl, wherein aryl is unsubstituted or substituted with one to five substituents independently selected from halogen, hydroxy, CO$_2$H, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
heteroaryl, wherein heteroaryl is unsubstituted or substituted with one to three substituents independently selected from hydroxy, halogen, CO$_2$H, $C_{1-6}$ alkyloxycarbonyl, aryl, $C_{1-6}$ alkyl, $C_{3-6}$ cycloalkyl, and $C_{1-6}$ alkoxy, wherein aryl, alkyl and alkoxy are unsubstituted or substituted with one to five halogens,
heterocyclyl, wherein heterocyclyl is unsubstituted or substituted with one to three substituents independently selected from oxo, hydroxy, halogen, CO$_2$H, $C_{1-6}$ alkyloxycarbonyl, aryl, $C_{1-6}$ alkyl, $C_{3-6}$ cycloalkyl, and $C_{1-6}$ alkoxy, wherein aryl, alkyl and alkoxy are unsubstituted or substituted with one to five halogens,
wherein any methylene ($CH_2$) carbon atom in $R^3$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;

and wherein $R^5$, $R^6$, $R^7$ and $R^8$ are as defined herein

In a class of this embodiment, $R^2$ is selected from the group consisting of:
methyl,
ethyl,
$CH_2$-cyclopropyl,
COOH,
COOMe,
COOEt,
CONMe$_2$,
CONH$_2$,
CONHMe,
CONHEt,
pyrrolidin-1-ylcarbonyl,
azetidin-1-ylcarbonyl, and
[(tetrazol-5-yl)amino]carbonyl.

Illustrative, but nonlimiting, examples of this embodiment of compounds of the present invention that are useful as dipeptidyl peptidase-IV inhibitors are the following:
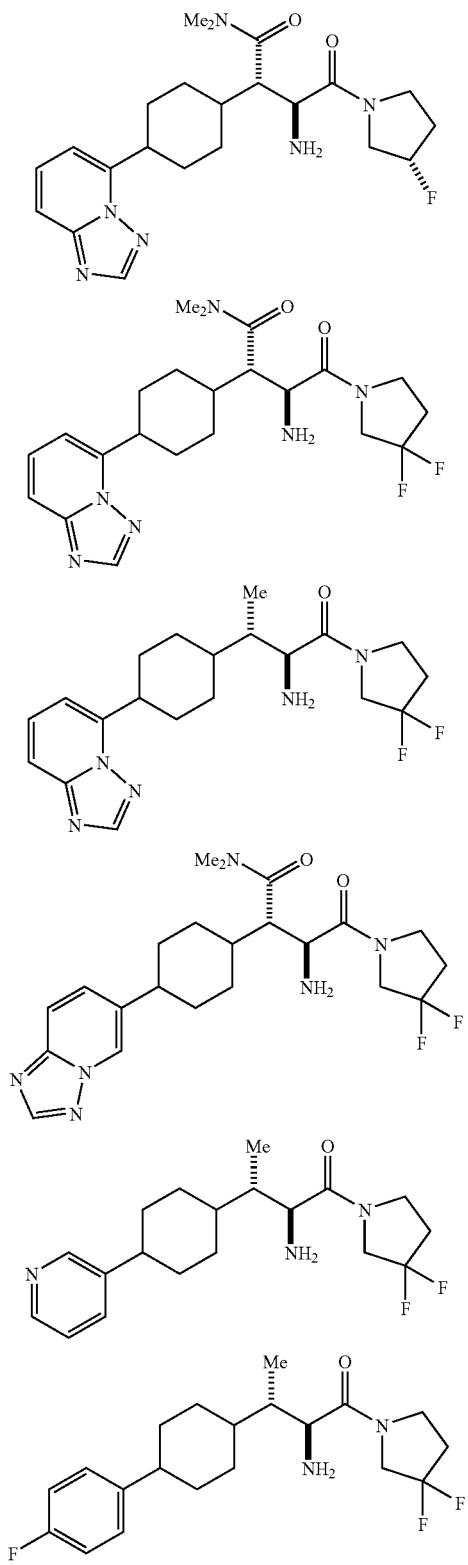
-continued
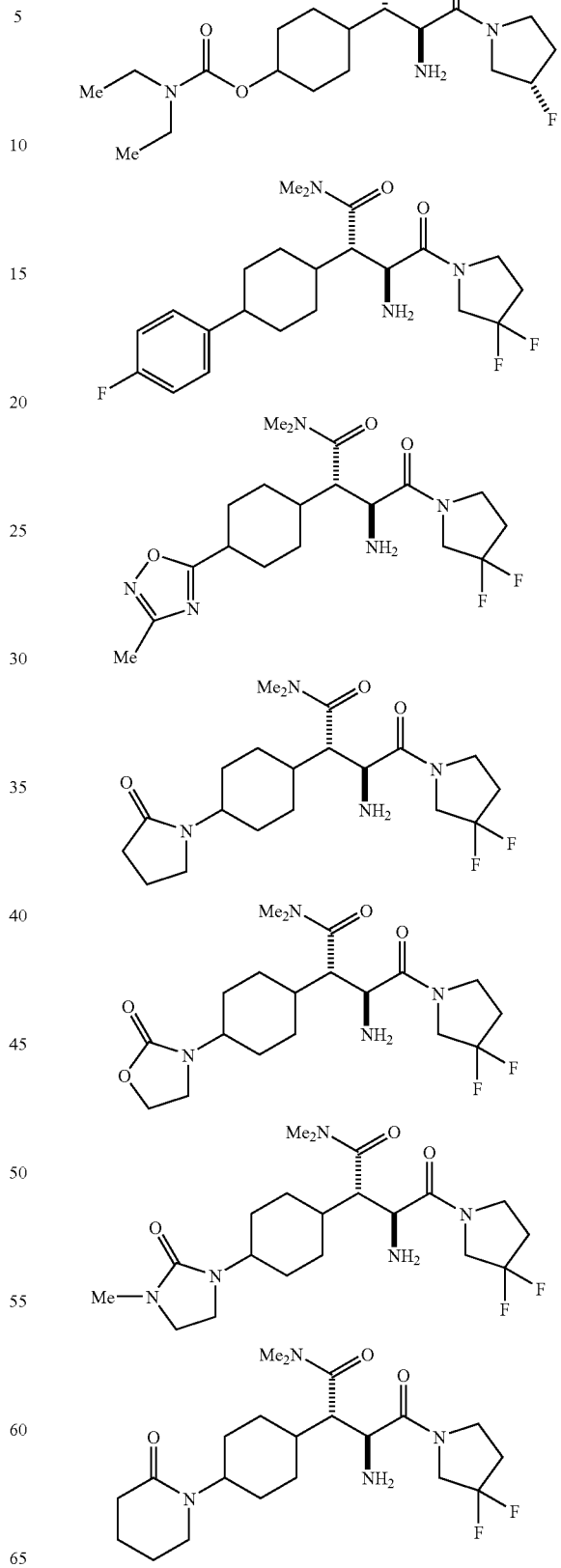

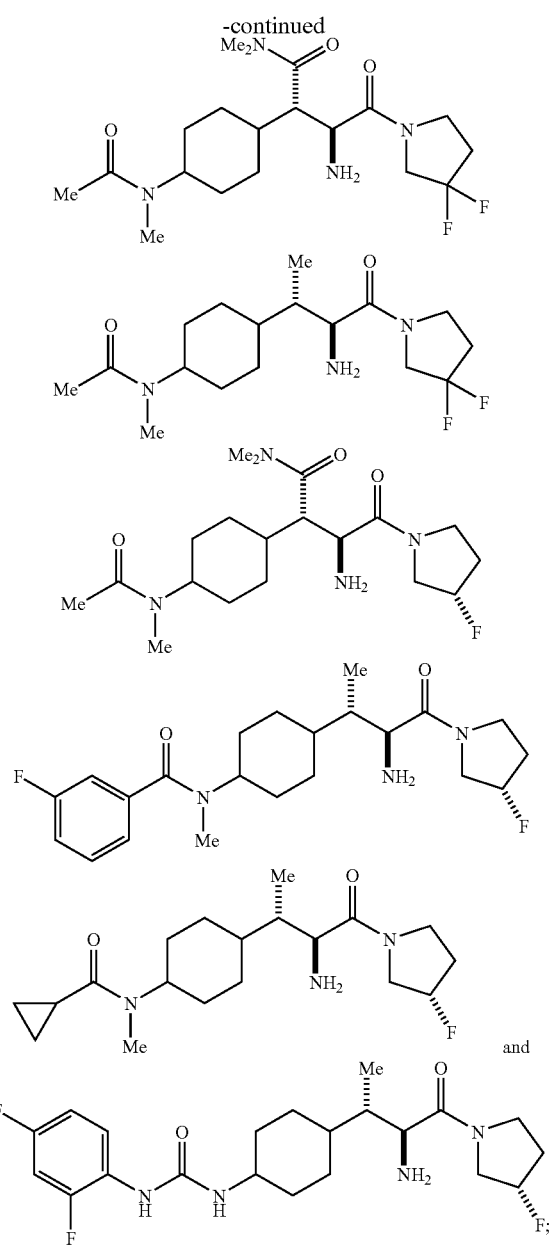

or a pharmaceutically acceptable salt thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and SO$_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, pyrrolidinone, oxazolidin-2-one, imidazolidine-2-one, pyridone, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention contain one or more asymmetric centers and can thus occur as racemates, racemic mixtures, single enantiomers, diastereomeric mixtures, and individual diastereomers. In particular the compounds of the present invention have an asymmetric center at the stereogenic carbon atom marked with an * in formulae Ia, Ib, Ic, Ie, and If; at the stereogenic carbon atoms marked with an * and ** in formulae Ib, Ic, Ie, and If; and at the stereogenic carbon atoms marked with an *, an , and * in formulae Ic and If. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. In particular, the compounds of the present invention contain a 1,4-disubstituted cyclohexane ring system. The present invention is intended to comprehend both the cis-1,4- and trans-1,4-disubstituted cyclohexane geometric isomers, including racemates and racemic mixtures, single enantiomers, diastereomeric mixtures and individual diastereomers thereof. In one embodiment of the compounds of the present invention, the 1,4-disubstituted cyclohexane ring in Formula I has the trans-1,4 stereochemistry.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred stereochemistry at the stereogenic carbon atom to which is attached the amino group of the alpha-amino acid from which these compounds are prepared. Formula Ib shows the preferred stereochemistry at the stereogenic carbon atom to which is attached the amino group of the alpha-amino acid and at the stereogenic carbon atom to which the $R^1$ substituent is attached. Formula Ic shows the preferred stereochemistry at the stereogenic carbon atom to which is attached the amino group of the alpha-amino acid, at the stereogenic carbon atom to which the $R^1$ substituent is attached, and at the stereogenic carbon atom to which the $R^2$ substituent is attached.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m=50$ µM; $k_{cat}=75$ s$^{-1}$; $k_{cat}/K_m=1.5 \times 10^6$ M$^{-1}$ s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an IC$_{50}$ of less than about 1 µM. Such a result is indicative of the intrinsic activity of the compounds in use as inhibitors the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (e.g. PACAP). Inactivation of these peptides by DP-IV may also play a role in glucose homeostasis. The DP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DP-IV inhibitors may also be useful to treat hypertension associated with this condition.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.,* 277: R910-R916 (1999)). ICV administration of GLP-1 in rats and mice also has profound effects on food intake (*Nature Medicine.* 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (*Nature Medicine* 6: 802-807 (2000)). In addition, studies with DP-IV deficient mice suggest that these animals are resistant to diet-induced obesity and associated pathology (e.g. hyperinsulinonemia).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DP-IV inhibitor diprotin A; and (3) GRF[3-44] is found in the plasma of a human GRF transgenic pig (*J. Clin. Invest.,* 83: 1533-1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (*Regulatory Peptides,* 90: 27-32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosuppressants in animal models of transplantation and arthritis. Prodipine (Pro-Pro-diphenyl-phosphonate), an irreversible inhibitor of DP-IV, was shown to double cardiac allograft survival in rats from day 7 to day 14 (*Transplantation,* 63: 1495-1500 (1997)). DP-IV inhibitors have been tested in collagen and alkyldiamine-induced arthritis in rats and showed a statistically significant attenuation of hind paw swelling in this model [Int. *J. Immunopharmacology,* 19:15-24 (1997) and *Immunopharmacology,* 40: 21-26 (1998)]. DP-IV is upregulated in a number of autoimmune diseases including rheumatoid arthritis, multiple sclerosis, Graves' disease, and Hashimoto's thyroiditis (*Immunology Today.* 20: 367-375 (1999)).

HIV Infection: DP-IV inhibition may be useful for the treatment or prevention of HIV infection or AIDS because a number of chemokines which inhibit HIV cell entry are potential substrates for DP-IV (*Immunology Today* 20: 367-375 (1999)). In the case of SDF-1alpha, cleavage decreases antiviral activity (*PNAS,* 95: 6331-6 (1998)). Thus, stabilization of SDF-1alpha through inhibition of DP-IV would be expected to decrease HIV infectivity.

Hematopoiesis: DP-IV inhibition may be useful for the treatment or prevention of hematopoiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m$ about $10^6$ M$^{-1}$ s$^{-1}$ or greater. In an electric shock jump test model of analgesia in rats, a DP-IV inhibitor showed a significant effect that was independent of the presence of exogenous endomorphin-2 (*Brain Research,* 815: 278-286 (1999)). Neuroprotective and neuroregenerative effects of DP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety: Rats naturally deficient in DP-IV have an anxiolytic phenotype (WO 02/34243; Karl et al., *Physiol. Behav.* 2003). DP-IV deficient mice also have an anxiolytic phenotype using the porsolt and light/dark models. Thus DP-IV inhibitors may prove useful for treating anxiety and related disorders.

Memory and Cognition: GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DP-IV inhibitors are expected to show similar effects Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH (*Eur. J. Clin. Chem. Clin. Biochem.*, 30: 333-338 (1992)).

Sperm motility/male contraception: DP-IV inhibition may be useful for the altering sperm motility and for male contraception because in seminal fluid, prostatosomes, prostate derived organelles important for sperm motility, possess very high levels of DP-IV activity (*Eur. J. Clin. Chem. Clin. Biochem.*, 30: 333-338 (1992)).

Gingivitis: DP-IV inhibition may be useful for the treatment of gingivitis because DP-IV activity was found in gingival crevicular fluid and in some studies correlated with periodontal disease severity (*Arch. Oral Biol.*, 37: 167-173 (1992)).

Osteoporosis: DP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297 and muraglitazar, and PPARα agonists such as fenofibric acid derivatives (gemfibrozil, clofibrate, fenofibrate and benzafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) PPARα/γ dual agonists, such as KRP-297 and muraglitazar, (vi) inhibitors of cholesterol absorption, such as beta-sitosterol and ezetimibe, (vii) acyl CoA: cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $□_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs);

(q) glucagon receptor antagonists;

(r) inhibitors of 11β-hydroxysteroid dehydrogenase type 1; and (s) inhibitors of cholesteryl ester transfer protein (CETP), such as torcetrapib.

Dipeptidyl peptidase-IV inhibitors that can be combined with compounds of structural formula I include those disclosed in WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); and WO 03/000181 (3 Jan. 2003). Specific DP-IV inhibitor compounds include isoleucine thiazolidide (P32/98); NVP-DPP-728; and LAF 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide $Y_5$ antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists," *Expert Opin. Ther. Patents*, 12: 1631-1638 (2002).

The potential utility of safe and effective activators of glucokinase (GKAs) for the treatment of diabetes is discussed in J. Grimsby et al., "Allosteric Activators of Glucokinase: Potential Role in Diabetes Therapy," *Science*, 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Synthetic methods for preparing the compounds of the present invention are illustrated in the following Schemes and Examples. Starting materials are commercially available or may be made according to procedures known in the art or as illustrated herein.

The compounds of the present invention can be prepared from alpha amino acid intermediates such as those of formula II and substituted heterocyclic intermediates such as those of formula III, using standard peptide coupling conditions. This coupling may then be followed by further modifications of the intermediate, reduction of the phenyl ring to a cyclohexyl ring, and deprotection to afford compounds of the general formula I. The preparation of these intermediates is described in the following Schemes, wherein m, p, X, $R^1$, $R^2$, and $R^3$ are as defined above. $R^4$ or other substituents may be introduced subsequently, and P is a suitable nitrogen protecting group such as tert-butoxycarbonyl (BOC), benzyloxycarbonyl (Cbz), and 9-fluorenylmethoxycarbonyl (Fmoc).

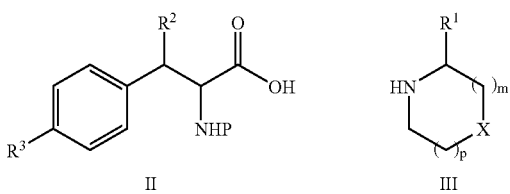

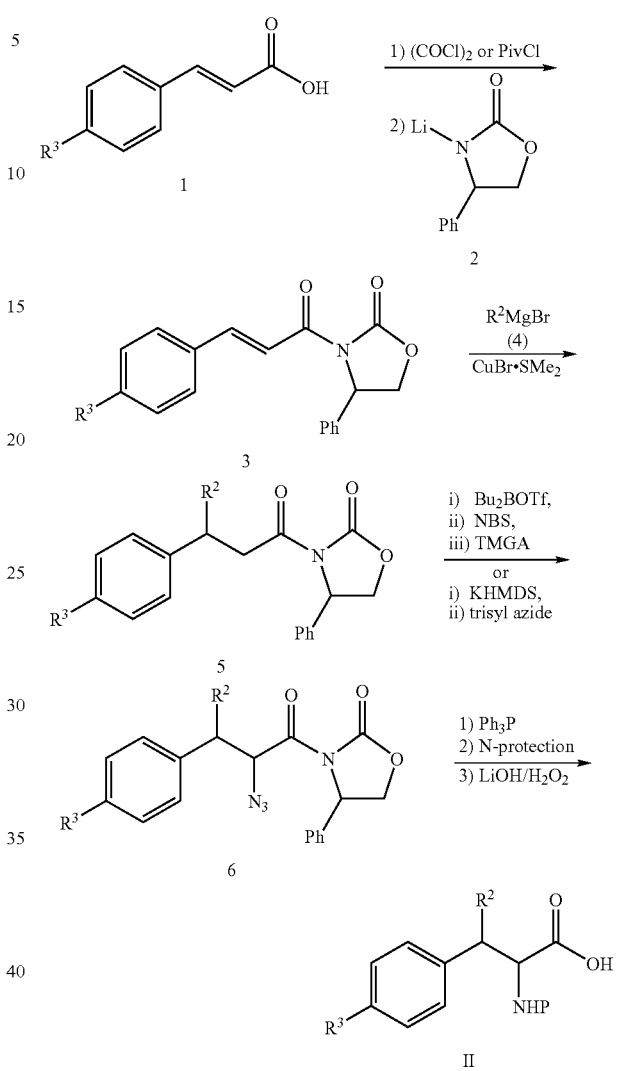

Intermediates of formula II are known in the literature or may be conveniently prepared by a variety of methods familiar to those skilled in the art. One convenient route is illustrated in Scheme 1. Cinnamic acids of the formula 1 are commercially available, known in the literature, or may be conveniently prepared by a variety of methods familiar to those skilled in the art. Activation of the acid, for example as its acid chloride by treatment with oxalyl chloride or as a mixed anhydride by reaction with pivaloyl chloride, followed by treatment with lithium oxazolidinone 2 gives acyl oxazolidinone 3. Copper catalyzed addition of the appropriate Grignard reagent 4 gives the desired intermediate 5. An alpha-azido moiety may be introduced in one of two convenient ways. First, the boron enolate generated from acyl oxazolidinone 5 by treatment with boron triflate and a base such as triethylamine or N,N-diisopropylethylamine is brominated by reaction with N-bromosuccinimide. The resultant bromide is displaced with azide, for example, by treatment with tetramethylguanidinium azide (TMGA) to provide azide 6. Alternatively, the potassium enolate of acyl oxazolidinone 5, generated, for example, with potassium hexamethyldisilazide, may be reacted with 2,4,6-triisopropylbenzenesulfonyl azide (trisyl azide) to provide azide 6 directly. The azide is reduced by treatment with triphenylphosphine and the resultant amine protected with an appropriate group, for example, as its N-tert-butyloxycarbonyl (Boc) derivative by treatment with di-tert-butyldicarbonate. The oxazolidinone is hydrolyzed, conveniently by treatment with lithium hydroperoxide, to provide the desired acid intermediate II. As will be readily apparent to those skilled in the art, all four diastereomers of acid II are available in enantiomerically pure form via this route, through the appropriate selection of either the (R) or (S) enantiomer of oxazolidinone 2 and employing the appropriate method for conversion of acyl oxazolidinone 5 to azide 6.

presence of, for example, the (R) isomer of the CBS catalyst. The alcohol is coupled to N-Boc glycine to provide ester 10. [3,3]-Sigmatropic rearrangement of the enolate of ester 10 may be achieved as described in the literature (U. Kazmaier et al., *Angew. Chem. Int. Ed. Eng*, 1994, 33: 998-999) to provide intermediate IIa.

SCHEME 3

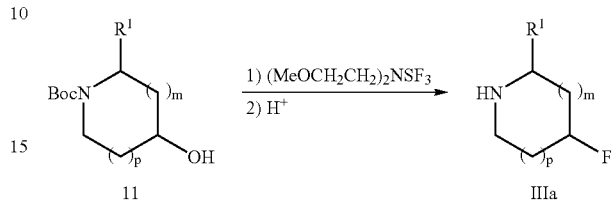

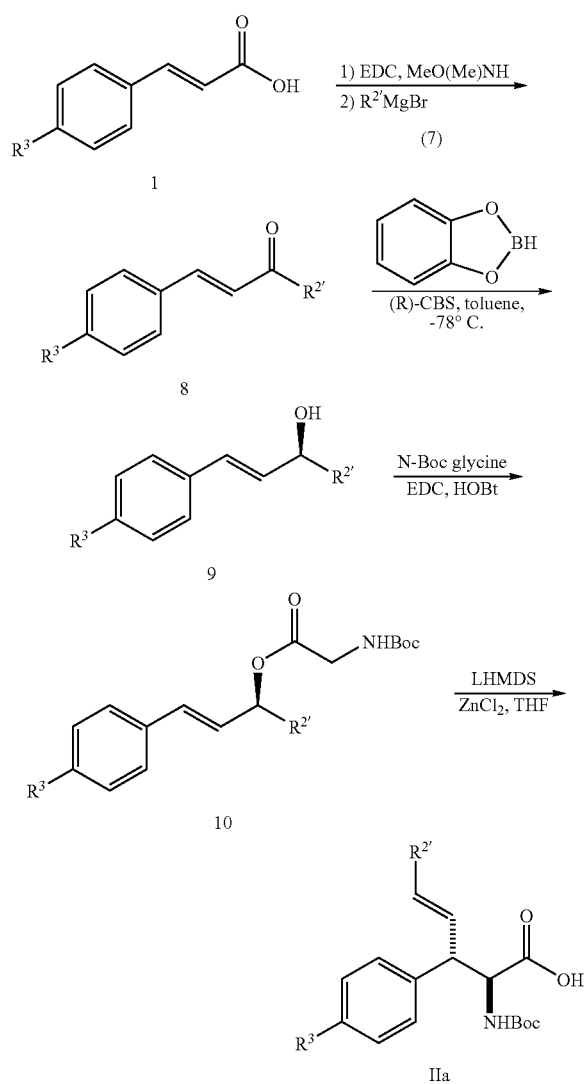

Compounds of formula III are commercially available, known in the literature or may be conveniently prepared by a variety of methods familiar to those skilled in the art. One convenient method for the preparation of intermediate III wherein X is CHF is shown in Scheme 3. An appropriately protected alcohol 11, which itself is known in the literature or may be conveniently prepared by a variety of methods familiar to those skilled in the art, is treated with a fluorinating reagent such as (diethylamino)sulfur trifluoride (DAST) or [bis(2-methoxyethyl)amino]sulfur trifluoride to provide, after deprotection, the fluoro intermediate IIIa.

SCHEME 4

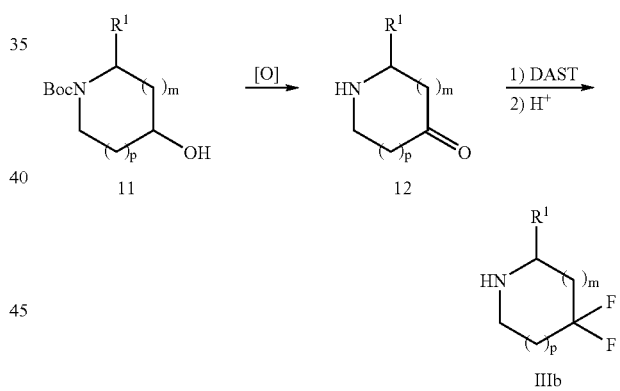

A method for the preparation of intermediate III wherein X is $CF_2$ is shown in Scheme 4. An appropriately protected alcohol 11 is oxidized to the corresponding ketone 12 by a variety of methods known to those skilled in the art. Ketone 12 is treated with a fluorinating reagent such as DAST to provide, after deprotection, the difluoro intermediate IIIb.

An alternate method for the preparation of intermediate II wherein $R^2$ contains an optionally substituted vinyl group, and $R^2$ and the protected amine are anti to each other is shown in Scheme 2. Cinnamic acid 1 may undergo EDC-mediated coupling with N,O-dimethylhydroxylamine followed by treatment with the appropriate Grignard reagent 7 to provide ketone 8. Reduction to alcohol 9 may be achieved in an asymmetric fashion by treatment with catecholborane in the

SCHEME 5

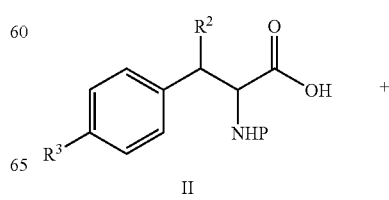

-continued

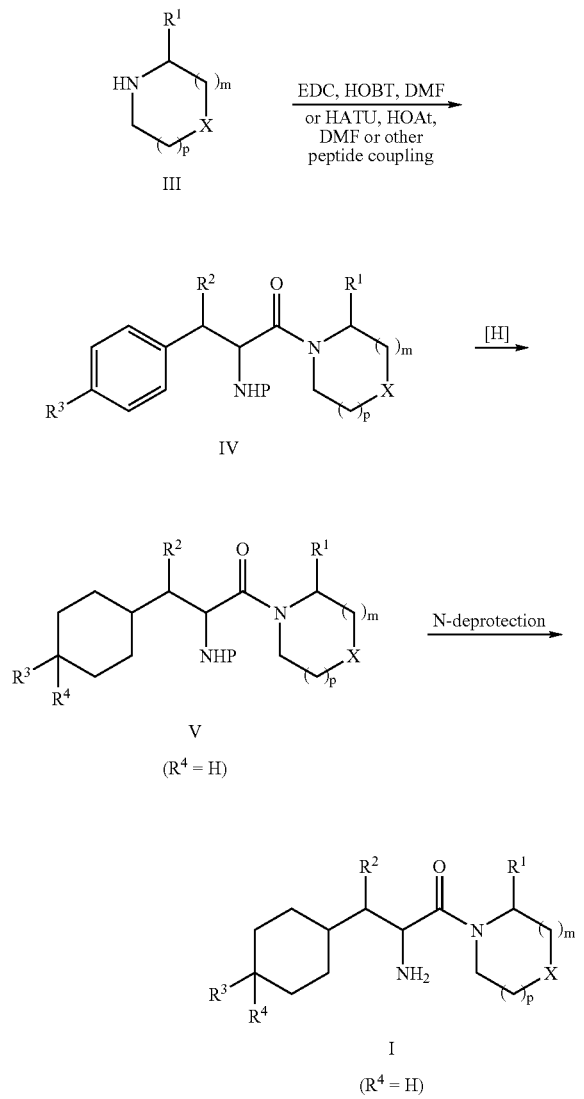

V
($R^4$ = H)

I
($R^4$ = H)

Intermediates II and III are coupled under standard peptide coupling conditions, for example, using 1-ethyl-3-(3-dimethylaminopropyl)carbodiimide and 1-hydroxybenzotriazole (EDC/HOBT) or O-(7-azabenzotriazol-1-yl)-N,N,N',N'-tetramethyluronium hexafluorophosphate and 1-hydroxy-7-azabenzotriazole (HATU/HOAT) in a solvent such as N,N-dimethylformamide (DMF) or dichloromethane for 3 to 48 h at ambient temperature to provide Intermediate IV as shown in Scheme 5. In some cases, Intermediate III may be a salt, such as a hydrochloride or trifluoroacetic acid salt, and in these cases it is convenient to add a base, generally N,N-diisopropylethylamine, to the coupling reaction. Intermediate IV may be further modified to provide compounds of the general formula I. For example, reduction of the phenyl substituent by hydrogenation over a suitable catalyst known to those familiar with the art may afford an intermediate such as V wherein $R^4$=H. This intermediate may be deprotected with acid or base, or the protecting group may be removed in the reduction step, affording compounds of the general formula I wherein $R^4$=H.

SCHEME 6

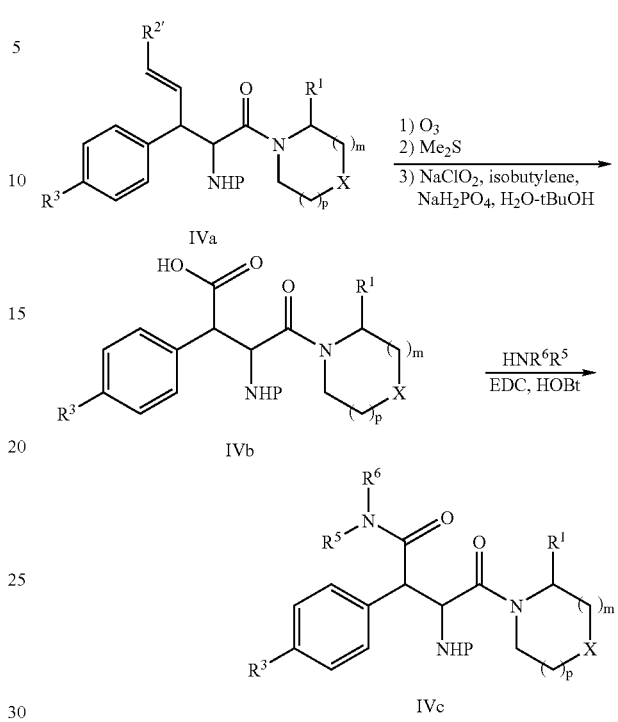

The intermediates described in the above schemes may be further modified before the sequences are completed, for example, by manipulation of the substituents on $R^2$. These manipulations may include, but are not limited to, reduction, oxidation, alkylation, acylation, and hydrolysis reactions which are commonly known to those skilled in the art. One such example of further manipulation is illustrated in Scheme 6, wherein $R^2$ represents an optionally substituted vinyl group as illustrated by intermediate IVa. Ozonolysis of intermediate IVa, followed by oxidation provides acid IVb. The acid may be coupled with an amine to give amide IVc.

SCHEME 7

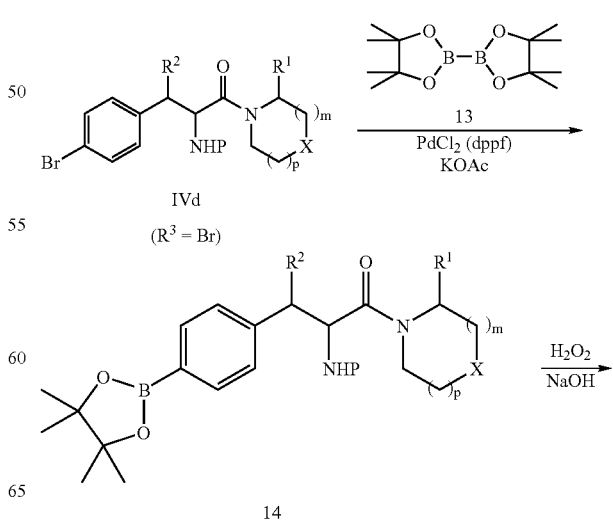

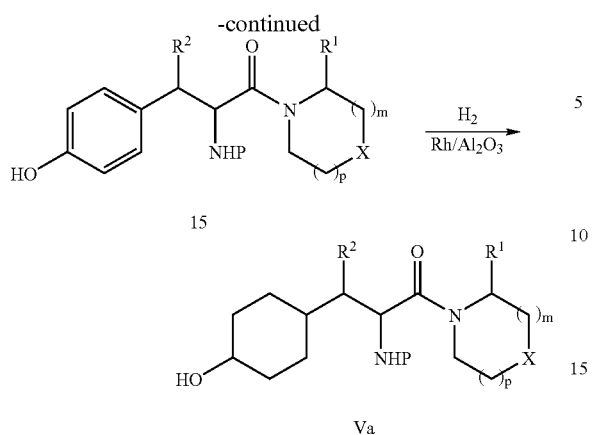

The compounds represented by Intermediate IV are further modified by a variety of methods to afford compounds corresponding to I, and these methods are familiar to anyone skilled in the art. One such method includes hydrogenation of the corresponding phenol, and this method is illustrated in Scheme 7. Conversion of the aromatic bromide intermediate IVd to the corresponding pinacolatoborate ester 14 may be accomplished by heating the compound and bis-(pinacolato)diboron 13 in a polar solvent such as DMSO in the presence of a palladium catalyst such as [1,1'-bis(diphenylphosphino)-ferrocene]dichloropalladium (II) and a base such as potassium acetate. The borate ester thus obtained may then be oxidized by a mild oxygen source such as hydrogen peroxide under basic aqueous conditions to give the corresponding phenol 15. The phenol may then be reduced by exposure to an atmosphere of 50 psi hydrogen in the presence of a catalyst such as 5% elemental rhodium on alumina to afford cyclohexanol Va.

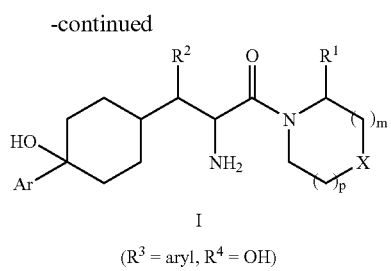

($R^3$ = aryl, $R^4$ = OH)

Intermediate Va may be converted to compounds represented by the general formula I by a variety of methods, and several of those methods are provided in the following schemes to further illustrate the scope of the invention. As is illustrated in Scheme 8, the alcohol Va may be oxidized by a variety of methods, for example by exposure to [1,1,1-tris(acetyloxy)-1,1-dihydro-1,2-benziodoxol-3-(1H)-one] (Dess-Martin periodinane) 16 to afford the corresponding ketone 17. Those instances in compounds of structural formula I where $R^3$ represents an aryl substituent and $R^4$ represents a hydroxyl substituent may be readily prepared from this intermediate. Addition of a variety of aryllithium reagents or arylmagnesium halide reagents to this ketone affords the corresponding tertiary alcohols 18. The amine substituent on these compounds may then be deprotected by a variety of methods such as treatment with acid, base, or hydrogenation, to afford compounds that correspond to the general formula I, wherein $R^3$=aryl and $R^4$=OH.

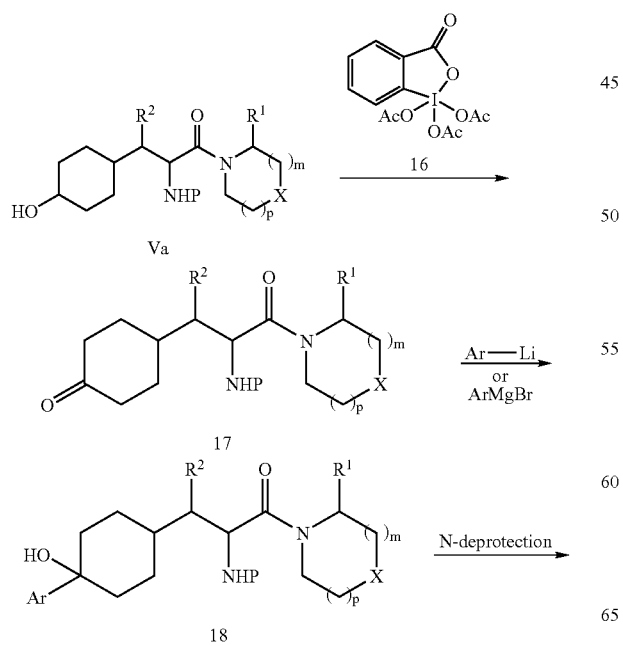

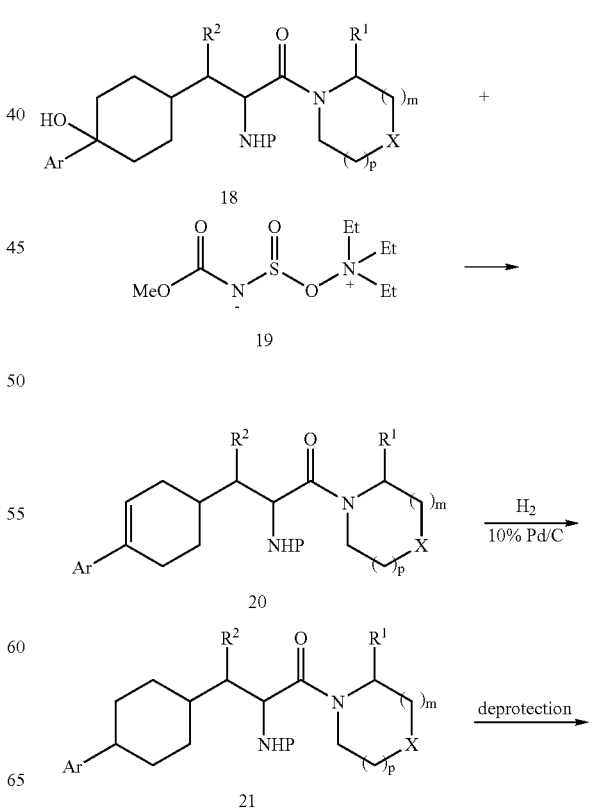

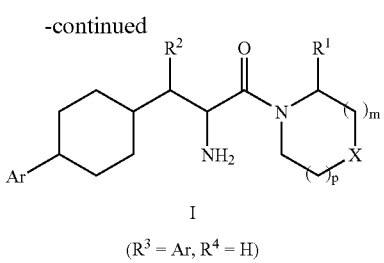

Intermediate 18 from Scheme 8 may be otherwise derivatized to afford compounds corresponding to the general Formula I as illustrated in Scheme 9. The tertiary alcohol may be removed with the use of a dehydrating reagent such as (methoxycarbonylsulfamoyl)triethylammonium hydroxide (Burgess reagent) 19 to afford the olefin 20. Exposure of this intermediate to hydrogen gas in the presence of a catalyst such as 10% palladium on carbon affords the fully saturated cyclohexane 21. The amine on this intermediate may be deprotected with acid or base, or the protecting group may be removed in the preceding hydrogenation step, to afford compounds that correspond to the general Formula I, wherein $R^3$=aryl and $R^4$=H.

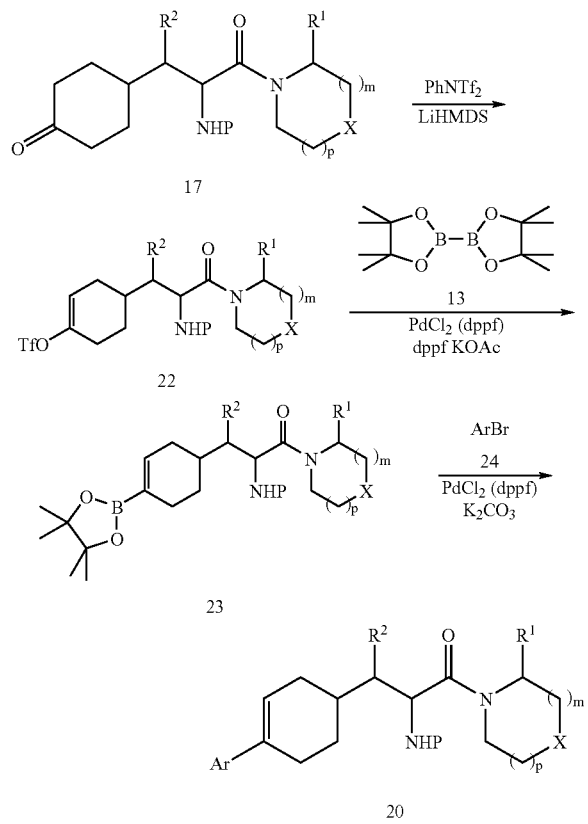

An alternative pathway may also be followed for the conversion of ketone 17 from Scheme 8 to intermediate 20 from Scheme 9, by using the modifications outlined in Scheme 10. Treatment of the ketone 17 with a strong base such as lithium hexamethyldisilizane, followed by treatment with N-phenyl-bis(trifluoromethanesulfonamide) affords the vinylic triflate intermediate 22. Conversion of the vinylic triflate 22 to the corresponding pinacolatoborate ester 23 may be accomplished by heating the compound and bis(pinacolato) diboron 13 in a polar solvent such as DMSO in the presence of a palladium catalyst such as [1,1'-bis(diphenylphosphino)ferrocene]dichloropalladium (II) and a base such as potassium acetate. The boronate ester may then be converted to the aryl vinylic intermediate 20 by heating with an arylbromide 24 in the presence of a base such as potassium carbonate and a palladium catalyst such as [1,1'-bis(diphenylphosphino)ferrocene]dichloropalladium (II). Arylbromides of the structure 24 are commercially available, known in the literature, or may be prepared by those familiar with the art. Intermediate 20 may then be converted to compounds such as I using the procedures detailed in Scheme 9.

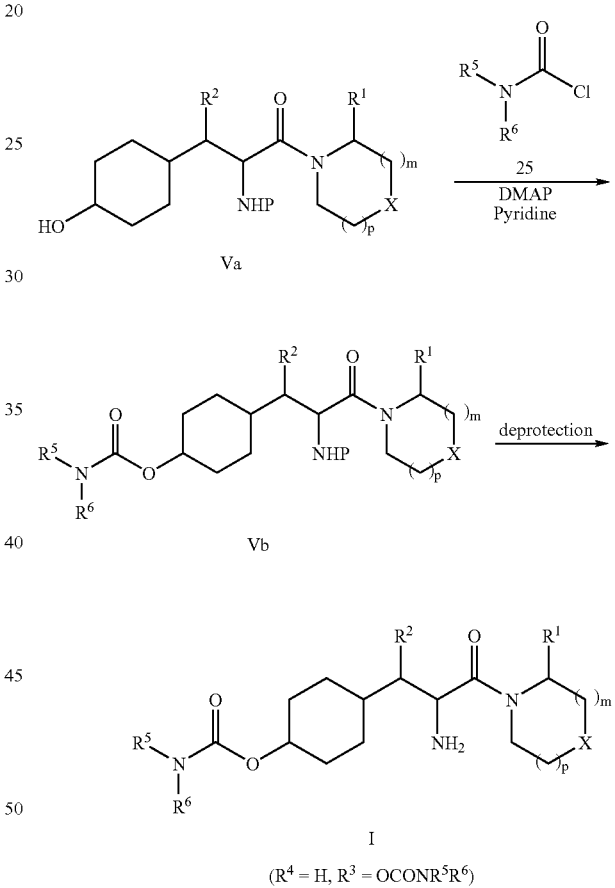

Intermediate Va from Scheme 7 may undergo other transformations to afford compounds of structural formula I as well. One such sequence is detailed in Scheme 11. Intermediate Va may be treated with a carbamoyl chloride reagent 25 in the presence of 4-dimethylaminopyridine and pyridine to afford the carbamate intermediate Vb. Carbamoyl chlorides of the general formula 25 are commercially available, known in the literature, or may be readily synthesized by those familiar with the art. The amine substituent on Intermediate Vb may then be deprotected using, for example, acid, base, or hydrogenation to afford I, wherein $R^3$=OCONR$^5$R$^6$ and $R^4$=H.

SCHEME 12

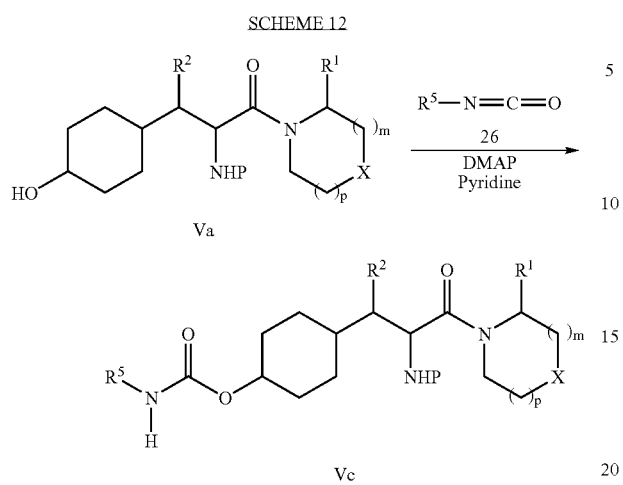

In those instances in which the substituent $R^6$ of compounds of the structural formula I in Scheme 11 is a hydrogen, the compound may also be synthesized using the method outlined in Scheme 12. Intermediate Va may be treated with an isocyanate reagent 26 under basic conditions to afford the carbamate Vc. Isocyanates of the formula 26 are commercially available; known in the literature, or may be readily synthesized by those familiar with the art. Intermediate Vc may then be subjected to the same deprotection conditions as carbamate Vb in Scheme 11, to afford compounds of the formula I wherein $R^3$=OCONHR$^5$ and $R^4$ is a hydrogen.

SCHEME 13

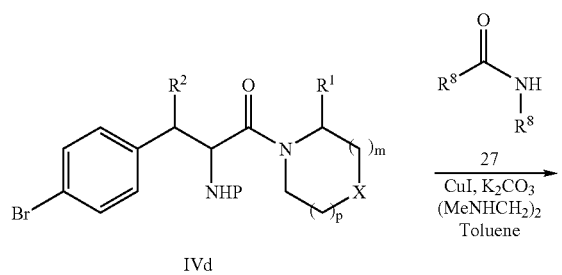

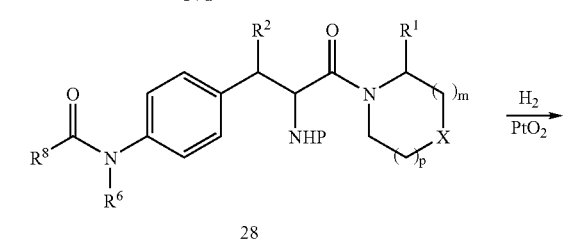

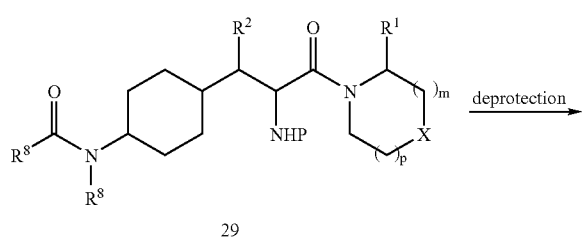

-continued

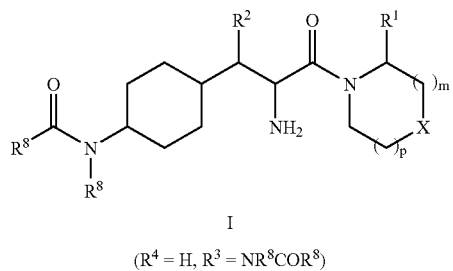

I ($R^4$ = H, $R^3$ = NR$^8$COR$^8$)

Intermediate IVd ($R^3$=Br) from Scheme 7 may be derivatized using other methods as well to afford compounds of the structural formula I. An additional method to accomplish this is presented in Scheme 13. Intermediate IVd may be converted to the corresponding aromatic amide using the procedure described in the literature (S. L. Buchwald et al., *J. Am. Chem. Soc.* 2002, 124, 7421-7428). The aromatic bromide is treated with an amide of structural formula 27 in the presence of Cu(I) to afford the amide 28. Amides of structural formula 27 are commercially available, known in the literature, or may be readily prepared by those familiar with the art. The N-arylamide 28 may then be subjected to a hydrogen gas atmosphere in the presence of a platinum catalyst such as platinum (IV) oxide to afford the corresponding N-cyclohexylamide 29. As will be readily apparent to those skilled in the art, the hydrogenation of intermediate 28 may produce a mixture of cis and trans diastereomers about the newly formed cyclohexyl ring. These diastereomers may be used as a mixture in any ratio or alternatively enriched in either diastereomer by liquid chromatography, fractional crystallization, or other purification methods to afford compounds of the present invention. The amine nitrogen of intermediate 29 may be deprotected by acid, base, hydrogenation, or other reactions to afford compounds of structural formula I wherein $R^3$=NR$^8$COR$^8$ and $R^4$=H, that are within the scope of this invention.

SCHEME 14

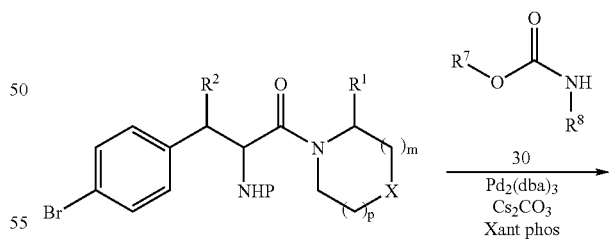

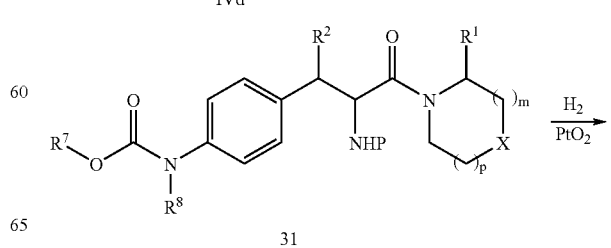

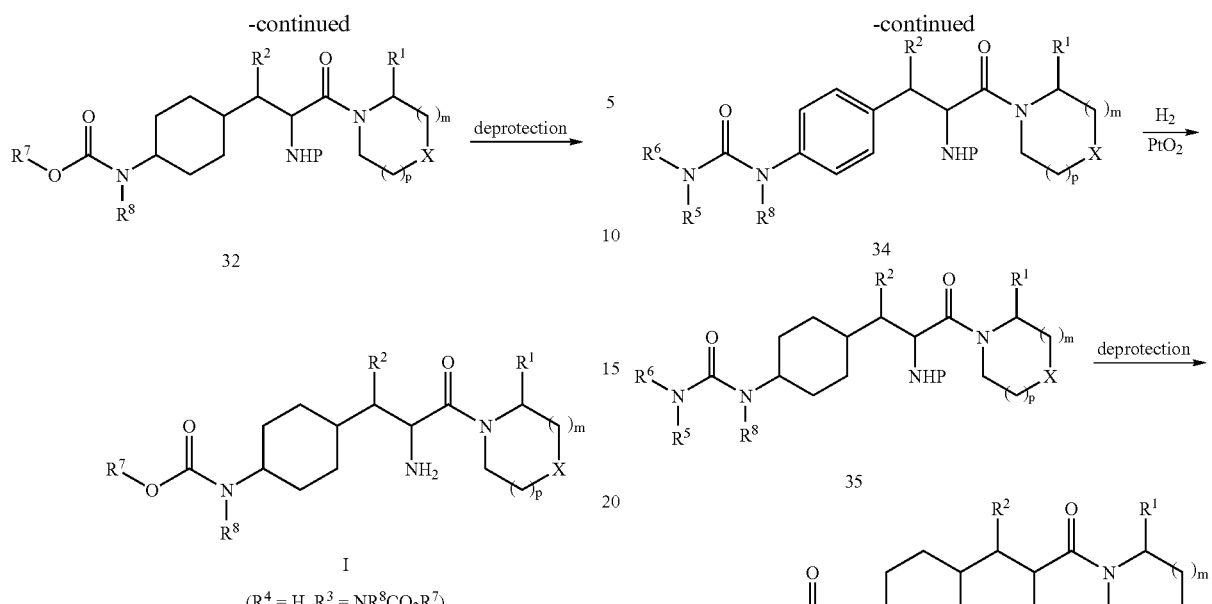

In a similar fashion to the procedure outlined in Scheme 13, the intermediate IVd may be derivatized to the corresponding carbamoyl derivative as illustrated in Scheme 14. Intermediate IVd is reacted with a carbamate of the general structure 30 in the presence of a palladium catalyst such as tris(dibenzylideneacetone)dipalladium(0) and a base such as cesium carbonate in the presence of a phosphine ligand. Carbamates of the general structure 30 are commercially available, known in the literature, or may be readily prepared by those familiar with the art. The N-arylcarbamate 31 is then hydrogenated in the presence of a platinum catalyst such as $PtO_2$ to afford the corresponding cyclohexylcarbamate 32. As will be readily apparent to those skilled in the art, the hydrogenation of intermediate 32 may produce a mixture of cis and trans diastereomers about the newly formed cyclohexyl ring. These diastereomers may be used as a mixture in any ratio or alternatively enriched in either diastereomer by the methods described previously to afford compounds of the present invention. The amine nitrogen of intermediate 32 may be deprotected by acid, base, hydrogenation, or other reactions to afford compounds of structural formula I wherein $R^4$=H and $R^3$=$NR^8CO_2R^7$, that are within the scope of this invention.

SCHEME 15

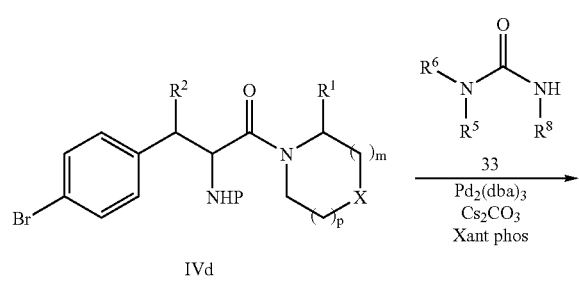

In a similar fashion to the procedure outlined in Scheme 14, intermediate IVd may be derivatized to the corresponding urea derivative as illustrated in Scheme 15. Intermediate IVd is reacted with a urea of the general structure 33 in the presence of a palladium catalyst such as tris(dibenzylideneacetone)dipalladium(0) and a base such as cesium carbonate in the presence of a phosphine ligand. Ureas of the general structure 33 are commercially available, known in the literature, or may be readily prepared by those familiar with the art. The N-arylurea 34 is then hydrogenated in the presence of a platinum catalyst such as $PtO_2$ to afford the corresponding N-cyclohexylurea 35. As will be readily apparent to those skilled in the art, the hydrogenation of intermediate 34 may produce a mixture of cis and trans diastereomers about the newly formed cyclohexyl ring. These diastereomers may be used as a mixture in any ratio or alternatively enriched in either diastereomer using the methods described previously to afford compounds of the present invention. The amine nitrogen of intermediate 35 may be deprotected by acid, base, hydrogenation, or other reactions to afford compounds of structural formula I wherein $R^4$=H and $R^3$=$NR^8CONR^5R^6$, that are within the scope of this invention.

SCHEME 16

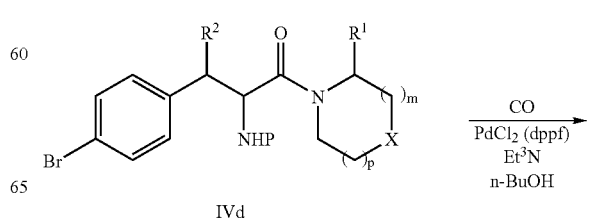

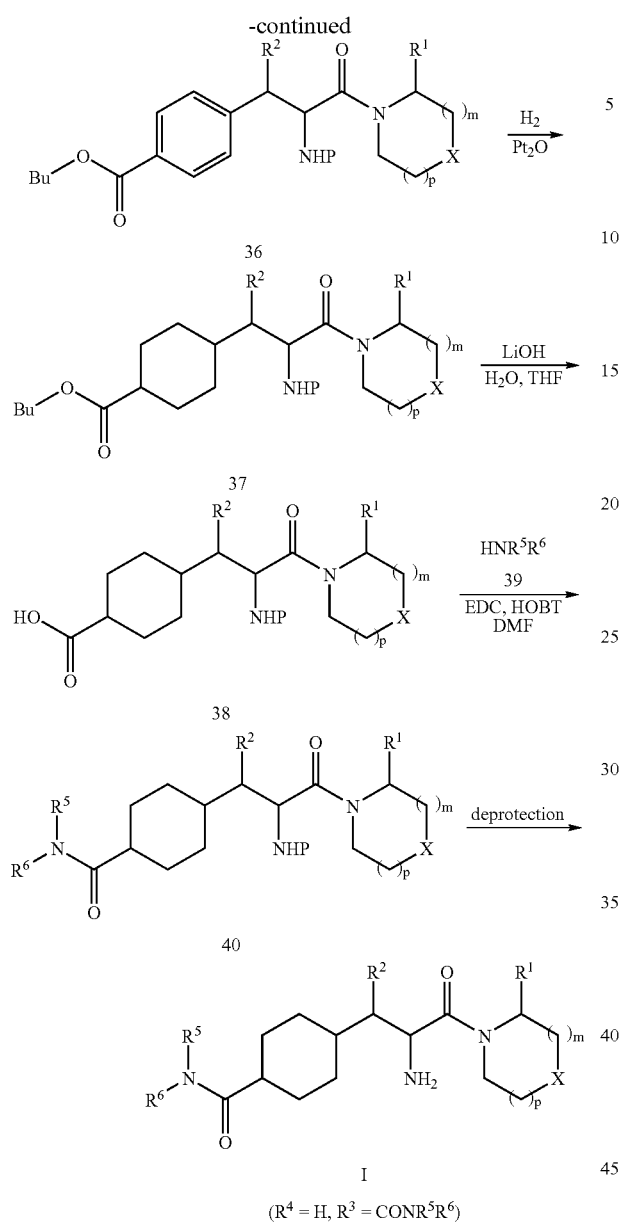

tereomer the methods described previously to afford compounds of the present invention. The butyl ester 37 is then treated with a base such as aqueous lithium hydroxide to afford the corresponding carboxylic acid 38. This material may be reacted with a variety of amines of the general formula 39 under amide coupling conditions such as EDC and HOBT in DMF to afford the corresponding amide derivatives 40. Amines of the formula 39 are commercially available, known in the literature, or may be readily prepared by those familiar with the art. Finally, deprotection of the amine nitrogen affords compounds of the general formula I wherein $R^4=H$ and $R^3=CONR^5R^6$.

SCHEME 17

Intermediate IVd from Scheme 7 may be otherwise derivatized to afford compounds of the structural formula I as is illustrated in Scheme 16. These derivatives may be achieved by conversion of the arylbromide substituent to the ester, and a convenient method to carry out this transformation has been described in the literature (S. Vinogradov et al., *Tetrahedron* 1998, 39, 8935-8938). Thus intermediate IVd is subjected to an atmosphere of carbon monoxide in the presence of a palladium catalyst such as [1,1'-bis(diphenylphosphino)-ferrocene]dichloropalladium (II) and an alcohol solvent such as n-butanol to afford the corresponding butyl ester 36. This material is then reduced in a hydrogen atmosphere by exposure to platinum (IV) oxide to give the cyclohexylcarboxylic acid butyl ester 37. As will be readily apparent to those skilled in the art, the hydrogenation of intermediate 36 may produce a mixture of cis and trans diastereomers about the newly formed cyclohexyl ring. These diastereomers may be used as a mixture in any ratio or alternatively enriched in either dias- Intermediate 38 from Scheme 16 may be otherwise derivatized as well to afford compounds of the structural formula I. One such method involves reacting intermediate 38 with an amide oxime such as acetamide oxime 41, in the presence of EDC and HOBT, as illustrated in Scheme 17. The resulting isoxadiazole 42 may be deprotected at the amine substituent to afford compounds of the structural formula I wherein $R^4=H$ and $R^3=$heteroaryl.

SCHEME 18

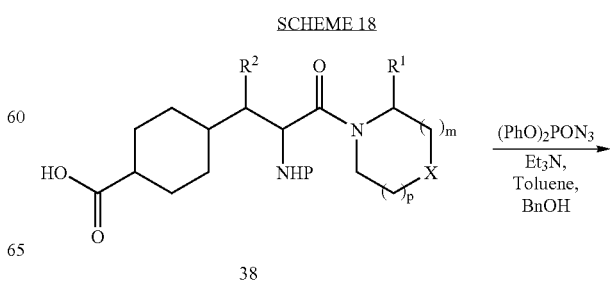

38

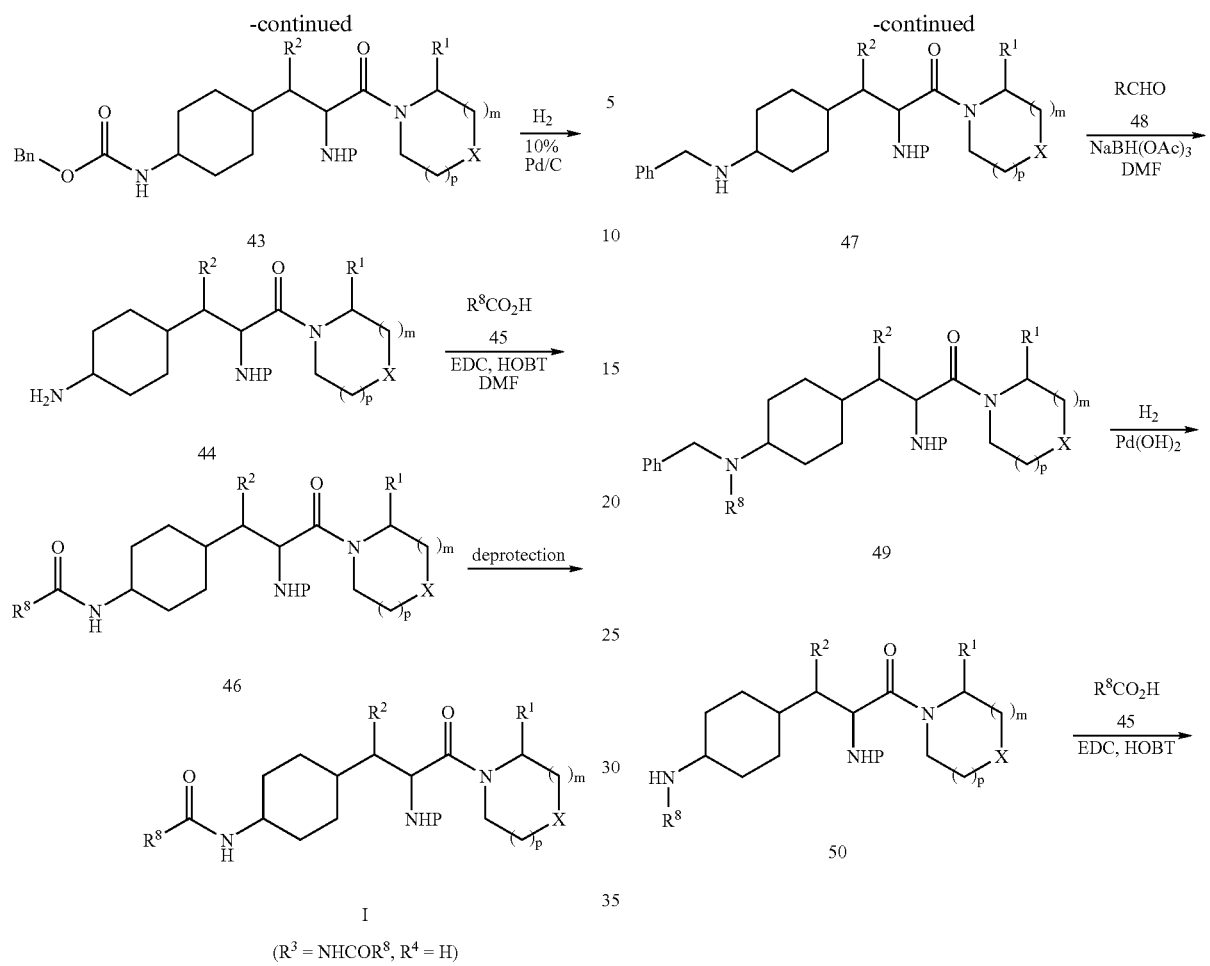

Intermediate 38 from Scheme 16 may be otherwise derivatized as well to afford compounds of the structural formula I. One such method involves reacting intermediate 38 with diphenylphosphorylazide (DPPA) in the presence of a base and heat, followed by treatment with benzyl alcohol, to afford the benzyl carbamate 43. Removal of the carbamoyl substituent may be accomplished by treatment of the compound with hydrogen and a palladium catalyst to afford the amino intermediate 44. This amine may be coupled under standard conditions with carboxylic acids 45 that are commercially available, known in the literature, or may be readily prepared by those familiar with the art. The amide intermediates 46 may then be deprotected at the amino substituent to afford compounds of the general structural formula I wherein $R^3$=NHCOR$^8$ and $R^4$=H.

SCHEME 19

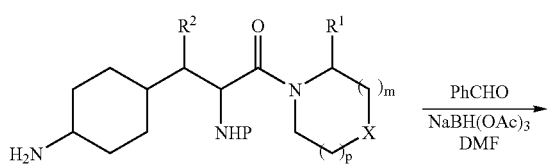

Intermediate 44 from Scheme 18 may also be converted to intermediate 29 from Scheme 13 using the methods illustrated in Scheme 19. Addition of benzaldehyde and sodium triacetoxyborohydride to the amine 44 in a polar solvent such as DMF affords the benzylamine intermediate 47. Addition of an additional aldehyde 48 that comprises the substituent $R^8$ under identical conditions affords the tertiary amine 49. Aldehydes of the formula 48 are commercially available, reported in the literature, or may be readily prepared by those familiar with the art. Removal of the benzylamine substituent in 49 may be accomplished by treatment with hydrogen and a palladium catalyst such as palladium(II) hydroxide to afford the amine intermediate 50. Coupling of this amine to a carboxylic acid 45 as illustrated in Scheme 18 affords the amide intermediate 29. This intermediate may be converted to compounds of the structural formula I using the methods outlined in Scheme 13.

SCHEME 20

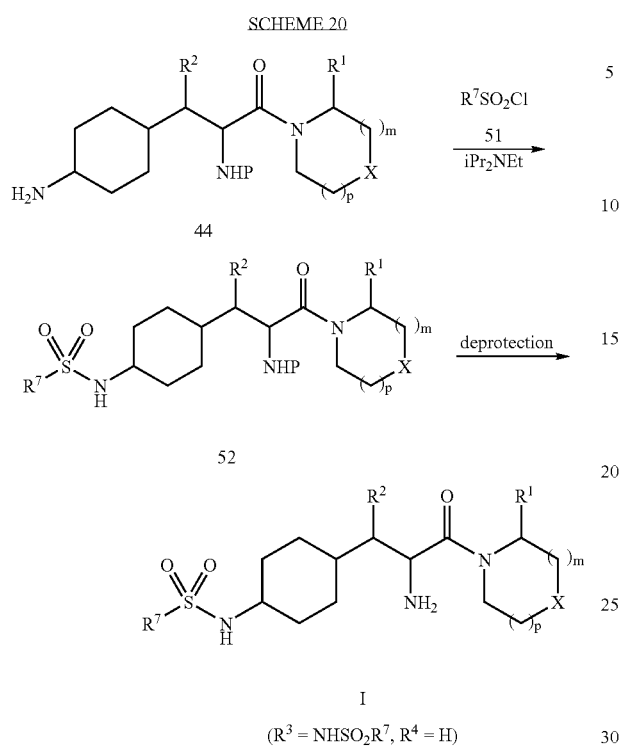

Intermediate 44 from Scheme 18 may be otherwise derivatized as well to afford compounds of the structural formula I, as illustrated in Scheme 20. Sulfonyl chloride reagents 51 are commercially available, known in the literature, or may be readily prepared by those familiar with the art. Addition of a sulfonyl chloride reagent 51 to intermediate 44 in the presence of a base such as N,N-diisopropylethylamine affords the sulfonamide intermediate 52. This sulfonamide may be deprotected at the amine substituent to afford compounds of formula I wherein $R^3=NHSO_2R^7$ and $R^4=H$.

SCHEME 21

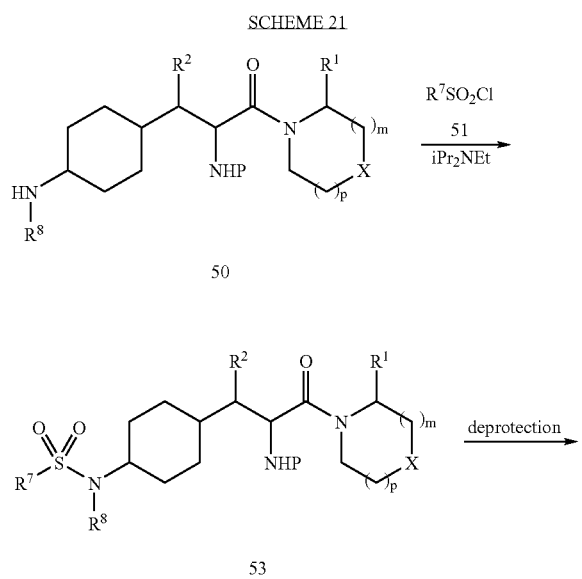

-continued

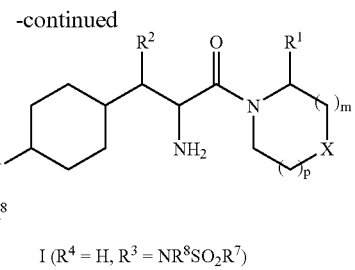

In a similar fashion, intermediate 50 from Scheme 19 may be derivatized to afford compounds of structural formula I, and this is illustrated in Scheme 21. The intermediate may be reacted with a sulfonyl chloride as was illustrated in Scheme 20, affording the sulfonamide intermediate 53. The amine functionality may then be deprotected to afford compounds of formula I wherein $R^4=H$ and $R^3=NR^8SO_2R^7$.

SCHEME 22

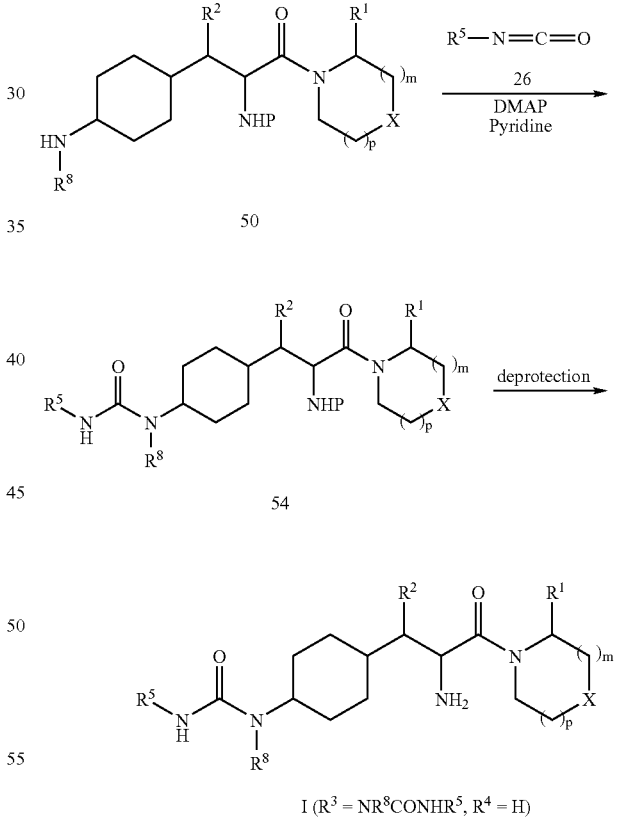

Intermediate 50 from Scheme 19 may be otherwise derivatized as well to afford compounds of the general formula I, and an additional such method is illustrated in Scheme 22. Intermediate 50 may be added to an isocyanate 26 under basic conditions to afford ureas such as 54. This intermediate may then be subjected to amine deprotection conditions to afford compounds of the formula I wherein $R^3=NR^8CONHR^5$ and $R^4=H$.

SCHEME 23

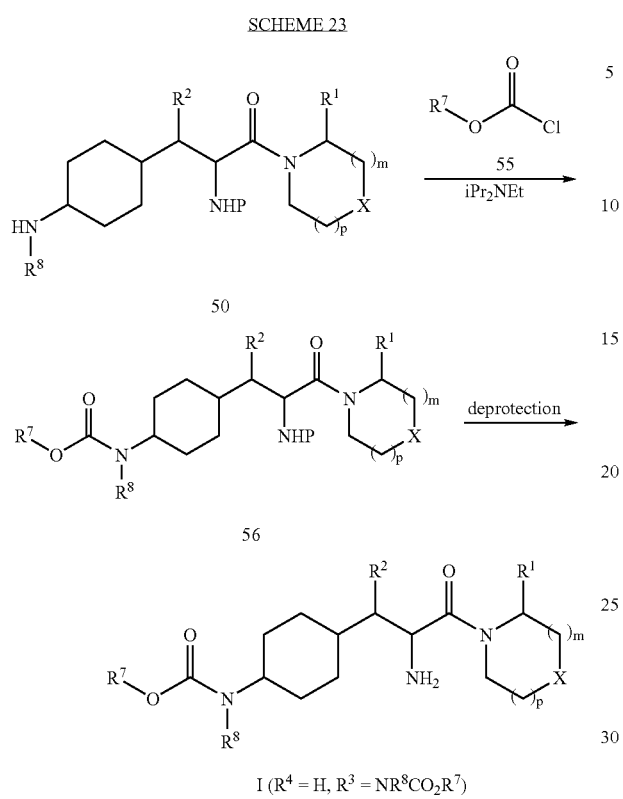

I ($R^4$ = H, $R^3$ = $NR^8CO_2R^7$)

Intermediate 50 from Scheme 19 may be otherwise derivatized as well to afford compounds of the general formula I, and an additional such method is illustrated in Scheme 23. Addition of a chloroformate reagent 55 in the presence of a base such as N,N-diisopropylethylamine affords the carbamate intermediate 56. Chloroformate reagents of the structure of intermediate 55 are commercially available, known in the literature, or may be readily prepared by those familiar with the art. Deprotection of the amine substituent in 56 using the methods described previously affords compounds of the formula I wherein $R^4$=H and $R^3$=$NR^8CO_2R^7$.

SCHEME 24

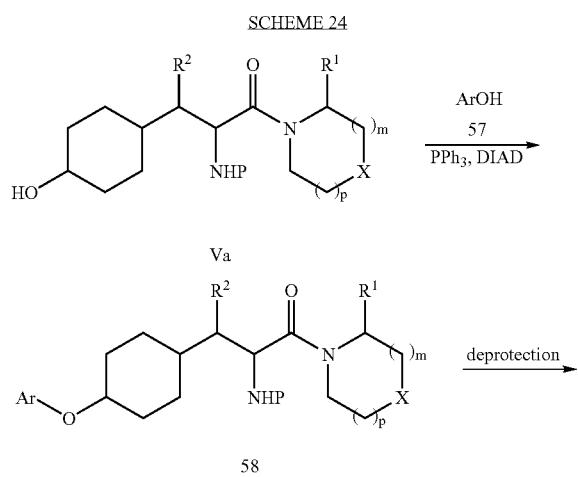

I ($R^4$ = H, $R^3$ = aryloxy)

(aryl = optionally substituted phenyl)

Intermediate Va from Scheme 7 may also be derivatized as illustrated in Scheme 24, involving displacement of the hydroxyl substituent. Addition of an optionally substituted phenol such as 57 in the presence of triphenylphosphine and diisopropyl azidocarboxylate (DIAD) affords the corresponding phenyl ether 58. Optionally substituted phenols of structure 57 are commercially available, known in the literature, or may be readily prepared by those familiar with the art. Deprotection of the amine function of 58 affords compounds of structure I wherein $R^4$=H and $R^3$=optionally substituted phenyloxy.

The following examples are provided so that the invention might be more fully understood. These examples are illustrative only and should not be construed as limiting the invention in any way. In some cases the order of carrying out the foregoing reaction schemes may be varied to facilitate the reaction or to avoid unwanted reaction products.

Intermediate 1

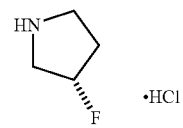

(3S)-3-Fluoropyrrolidine hydrochloride

Step A: Benzyl (3R)-3-hydroxypyrrolidine-1-carboxylate

A 22-L, 3-neck, round bottom flask equipped with mechanical stirrer, thermocouple, addition funnel and nitrogen bubbler was charged with 425 g (4.88 mol) of (3R)-3-hydroxypyrrolidine, 8 L of dichloromethane, and 1 L (7.17 mol) of triethylamine. The solution was cooled to 5-10° C. with an ice bath and then 1000 g (5.86 mol) of benzyl chloroformate was added dropwise over a period of about 1.5 h keeping the reaction temperature below 20° C. The reaction mixture was stirred for an additional h in the ice bath, then the bath was removed and the reaction mixture was allowed to warm to ambient temperature overnight. The mixture was poured into a large extractor containing about 15 L of saturated aqueous sodium bicarbonate solution. The aqueous phase was back-extracted with two 2-L portions of dichloromethane. The combined organics were dried over magnesium sulfate and concentrated to give an orange oil. The crude material was taken up in dichloromethane, applied to a 5-kg column of silica gel prepacked in 50% ethyl acetate/hexane, and eluted sequentially with 8 L of 50%, 16 L of 75%, then 100% ethyl acetate/hexane to provide the title compound as a yellow oil which crystallized upon standing.

Step B: Benzyl (3S)-3-fluoropyrrolidine-1-carboxylate

A 5-L, 3-neck, round bottom flask equipped with mechanical stirrer, thermocouple, addition funnel and nitrogen bubbler was charged with 375 mL (2.84 mol) of (diethylamino) sulfur trifluoride and 400 mL of dichloromethane. The solution was cooled to −78° C. To this was added via addition funnel a solution of 304 g (1.37 mol) of benzyl (3R)-3-hydroxypyrrolidine-1-carboxylate in 400 mL of dichloromethane over a 2-h period keeping the reaction temperature below −70° C. The reaction mixture was allowed to stir and warm slowly to ambient temperature overnight. The reaction mixture was added portion-wise with caution to a large extractor containing ice, water, and saturated aqueous sodium bicarbonate solution. The mixture was extracted with 8 L of ethyl acetate. The organic layer was washed with brine, dried over magnesium sulfate, and concentrated to give a brown oil. Purification by flash chromatography (silica gel, eluting with a 10 to 30% ethyl acetate/hexane gradient) gave the title compound as a brown oil.

Step C: (3S)-3-Fluoropyrrolidine hydrochloride

Benzyl (3S)-3-fluoropyrrolidine-1-carboxylate (249 g, 1.11 mmol) was dissolved in 2.3 L of ethanol and then 115 mL of water was added, followed by 30 g of 10% palladium on carbon. The mixture was shaken under 40 psi hydrogen for ~24 h. An additional 10 g and then 5 g of catalyst were added. The mixture was stirred under 40 psi hydrogen until complete. The mixture was filtered and the filter cake washed with ethanol. The combined filtrate and washings were treated with 185 mL of concentrated hydrochloric acid and concentrated to a colorless oil. The residue was azeotroped with toluene, then 2 L of diethyl ether were added. Isopropyl alcohol was added until the oil crystallized. The mixture was allowed to age at ambient temperature over the weekend. The crystals were collected, washed with diethyl ether, and dried in vacuo to give the title compound. The mother liquors and washings were combined, concentrated, azeotroped with toluene, and triturated with diethyl ether/isopropyl alcohol. The second crop was collected and dried in vacuo to give additional title compound. $[\alpha]_D=+8.64°$ (c=4, methanol).

Intermediate 2

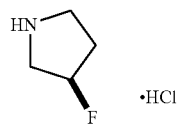

(3R)-3-Fluoropyrrolidine hydrochloride

Step A: Benzyl (3S)-3-acetoxypyrrolidine-1-carboxylate

A 22-L, 3 neck round bottom flask equipped with a mechanical stirrer, thermocouple, addition funnel and nitrogen bubbler was charged with 422 g (1.91 mol) of benzyl (3R)-3-hydroxypyrrolidine-1-carboxylate (Intermediate 1, Step A), 12 L of toluene, 751 g (2.86 mol) of triphenylphosphine, and 164 mL (2.86 mol) of glacial acetic acid. The resultant mixture was stirred at ambient temperature and then 500 g (2.87 mol) of diethyl azodicarboxylate was added via the addition funnel over a period of about 30 min, keeping the internal temperature <28° C. with a cold water bath. The reaction was stirred at ambient temperature overnight. The solvent was removed in vacuo and the residue was triturated with 6 L of diethyl ether. The solid was filtered off and washed well with diethyl ether. The filtrate and ether washings were combined and concentrated to a thick yellow oil with solids. Purification by flash chromatography (silica gel, eluting sequentially with 5% and a gradient of 10% to 30% ethyl acetate/hexane) gave the title compound as a pale yellow oil.

Step B: Benzyl (3S)-3-hydroxypyrrolidine-1-carboxylate

To a 20-L, three neck round bottom flask containing 427 g (1.62 mol) of benzyl (3S)-3-acetoxypyrrolidine-1-carboxylate was added 4 L of absolute ethanol followed by 101 g (1.57 mol) of potassium hydroxide in about 400 mL of water. After about 15 min, the reaction mixture was poured into 8 L of water and extracted with 8 L of ethyl acetate. The aqueous layer was then extracted with an additional 4 L of ethyl acetate. The combined organics were washed with saturated aqueous brine, dried over magnesium sulfate and concentrated to a thick oil and solids.

Step C: Benzyl (3R)-3-fluoropyrrolidine-1-carboxylate

A 366 g (1.62 mol) portion of benzyl (3S)-3-hydroxypyrrolidine-1-carboxylate was converted to the title compound essentially following the procedure outlined in Intermediate 1, Step B.

Step D: (3R)-3-Fluoropyrrolidine hydrochloride salt

A 222 g (1.0 mol) portion of benzyl (3R)-3-fluoropyrrolidine-1-carboxylate was converted to the title compound essentially following the procedure outlined in Intermediate 1, Step C. $[\alpha]_D=-8.61$ (c=4, methanol).

Intermediate 3

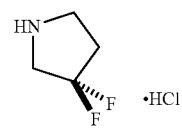

3,3-Difluoropyrrolidine hydrochloride

Step A: Benzyl 3-oxopyrrolidine-1-carboxylate

A 12-L, 3 neck round bottom flask equipped with a mechanical stirrer, thermocouple, condenser, and nitrogen bubbler was charged with 351 g (1.61 mol) of benzyl (3R)-3-hydroxypyrrolidine-1-carboxylate (Intermediate 1, Step A), 6 L of dichloromethane, 500 g of powdered molecular sieves, and 400 g (3.41 mol) of N-methylmorpholine-N-oxide. The resultant suspension was stirred at ambient temperature and to this was added 12.9 g (0.0367 mol) of tetrapropylammonium perruthenate. The reaction temperature was kept at ≦30° C. with a cold water bath. The mixture was stirred at ambient temperature for 2 h. The mixture was poured onto a plug of 5 kg of silica gel and eluted with 10% ethyl acetate/dichloromethane to give the title compound as an orange oil.

Step B: Benzyl 3,3-difluoropyrrolidine-1-carboxylate

A 12-L, 3 neck round bottom flask equipped with a mechanical stirrer, thermocouple, addition funnel and nitrogen bubbler was charged with 292 g (1.33 mol) of benzyl 3-oxopyrrolidine-1-carboxylate and 3 L of dichloromethane. To the stirring solution at ambient temperature was added dropwise 530 mL (4.0 mol) of (diethylamino)sulfur trifluoride over a period of about 3 h, keeping the internal temperature less than 25° C. using a cold water bath. The mixture was stirred at ambient temperature overnight. The mixture was poured into a large extractor containing ice and solid sodium bicarbonate. Eight liters of ethyl acetate were then added and the mixture was made basic with sodium bicarbonate. The organic layer was dried over magnesium sulfate and concentrated to 309 g of a brown oil. Purification by flash chromatography (silica gel, 10 to 20% ethyl acetate/hexane gradient) gave the title compound.

Step C: 3,3-Difluoropyrrolidine hydrochloride

A 242 g (1.00 mol) portion of benzyl 3,3-difluoropyrrolidine-1-carboxylate was converted to the title compound essentially following the procedure outlined in Intermediate 1, Step C. $^1$H NMR (500 MHz, CD$_3$OD): δ 3.7 (t, 2H), 3.6 (t, 2H), 2.55 (m, 2H).

Intermediate 4

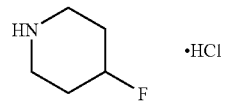

4-Fluoropiperidine hydrochloride

Step A: Benzyl 4-fluoro-1-piperidinecarboxylate

A 1-L, round bottom flask was charged with 12.64 g (51.4 mmol) of benzyl 4-oxo-1-piperidinecarboxylate and 300 mL of dichloromethane. To the stirring solution at −78° C. was added 19 mL (102.8 mmol) of [bis(2-methoxyethyl)amino]sulfur trifluoride via addition funnel over a period of about 1 h. The reaction mixture was allowed to warm slowly to ambient temperature overnight. The reaction mixture was added portionwise with caution to a large extractor containing water and saturated aqueous sodium bicarbonate solution. The mixture was extracted with dichloromethane (3×300 mL). The combined organic layers were washed once with saturated aqueous sodium bicarbonate solution, twice with 10% aqueous hydrochloric acid solution and saturated aqueous brine, dried over sodium sulfate, and concentrated in vacuo. Purification by flash chromatography on a Biotage® system (gradient, hexane to 65% ethyl acetate/hexane) afforded the desired product. LC/MS 242.1 (M+1).

Step B: 4-Fluoropiperidine hydrochloride

Benzyl 4-fluoro-1-piperidinecarboxylate (5.5 g, 23.2 mmol) was dissolved in 80 mL of ethanol and 1.0 g of 20% palladium hydroxide (dry basis) on carbon was added to the mixture. The mixture was shaken under 40 psi hydrogen for about 12 h then filtered through a Celite pad and washed with 100 mL of methanol. The combined filtrate and washings were treated with 60 mL of 1 M hydrogen chloride in diethyl ether and concentrated to a white waxy solid. The solid was dried in vacuo to give the title compound as a solid. The material was used without further purification. $^1$H NMR (CDCl$_3$): δ 4.95 (d, J=47.4 Hz, 1H), 3.70 (br s, 1H), 3.34-3.27 (m, 4H), 2.29 (dt, J=37.1, 12.3 Hz, 2H), 2.16 (br s, 2H).

Intermediate 5

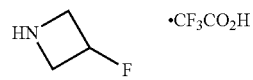

3-Fluoroazetidine trifluoroacetic acid salt

Step A: 1-Benzhydryl-3-fluoroazetidine

A 250 mL, round bottom flask was charged with 3.0 g (12.5 mmol) of 1-benzhydryl-3-fluoroazetidine and 80 mL of dichloromethane. To the stirring solution at −78° C. was added 4.6 mL (25 mmol) of [bis(2-methoxyethyl)amino]sulfur trifluoride via addition funnel over a period of about 3 h. The reaction mixture was allowed to warm slowly to ambient temperature overnight. The reaction mixture was added portionwise (with caution) to a large extractor containing water and saturated aqueous sodium bicarbonate solution. The mixture was extracted three times with 80 mL of dichloromethane. The combined organic layers were washed sequentially with saturated aqueous sodium bicarbonate solution, water and saturated aqueous brine, dried over sodium sulfate, and concentrated in vacuo. Purification by flash chromatography using a Biotage® system (gradient, hexane to 80% ethyl acetate/hexane) afforded the desired product. LC/MS 242.1 (M+1).

Step B: 3-Fluoroazetidine trifluoroacetic acid salt

1-Benzhydryl-3-fluoroazetidine (1.7 g, 7.04 mmol) was dissolved in 60 mL of ethanol and 500 mg of 20% palladium hydroxide (dry basis) on carbon. The mixture was shaken under 40 psi hydrogen for about 12 h. The mixture was filtered through a Celite pad and the filter cake washed with 100 mL of methanol. The combined washings were treated with 10 mL of trifluoroacetic acid and concentrated to give two oils, the more dense of which is the desired fluoroazetidine salt. The mixture was not purified further. $^1$H NMR (CDCl$_3$): δ 5.45-4.30 (dm, J=56.7 Hz, 1H), 4.46-4.38 (m, 2H), 4.24-2.17 (m, 2H).

Intermediate 6

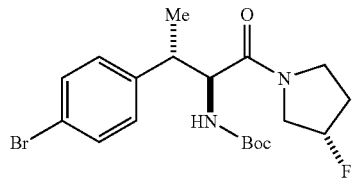

(3S)-1-[(2S,3S)-2-[(tert-Butoxycarbonyl)amino]-3-(4-bromophenyl)-1-oxobutanyl]-3-fluoropyrrolidine Step A: (4R)-3-[(2E)-3-(4-Bromophenyl)prop-2-enoyl]-4-phenyl-1,3-oxazolidin-2-one To a stirred solution of 4-bromocinnamic acid (5.79 g, 22.5 mmol) in anhydrous THF (250 mL) was added triethylamine (4.60 mL, 34.6 mmol) followed by trimethylacetyl chloride (3.54 mL, 24.7 mmol) at −78° C. The resultant suspension was stirred at −78° C. for 15 min, 0° C. for 1 h, and at −78° C. for 15 min before being transferred via cannula into a slurry of lithium 4(R)-4-phenyl-2-oxazolidinone at 0° C., which was prepared 15 min in advance at −78° C. by addition of n-butyllithium (19.1 mL, 30.5 mmol) to a solution of 4(R)-4-phenyl-2-oxazolidinone (5.0 g, 30.6 mmol) in anhydrous THF (150 mL) at −78° C. The resultant slurry was stirred at −78° C. for 1 h and room temperature for 12 h. The reaction was quenched with saturated aqueous ammonium chloride solution. The organic phase was separated, concentrated in vacuo, and the crude product was used directly for the next step. LC/MS 372.0 (M+1).

Step B: (4R)-3-[(3R)-3-(4-Bromophenyl)butanoyl]-4-phenyl-1,3-oxazolidin-2-one

To a stirred solution of copper(II) bromide dimethylsulfide complex (8.78 g, 42.7 mmol) in THF (60 mL) and dimethylsulfide (30 mL) was added methylmagnesium bromide (12.7 mL, 3.0M in diethyl ether, 38.1 mmol) at −40° C. The resultant mixture was stirred at −40° C. for 30 min, then warmed to −20° C. The product from Step A (3.53 g, 9.48 mmol) in THF (30 mL) was added to the above reaction mixture over 1 h at −20° C. The resultant mixture was stirred at −20° C. for 2 h, then slowly warmed to room temperature and stirred at room temperature for 12 h. The reaction was quenched by slow addition of saturated aqueous ammonium chloride solution. The organic phase was separated and the aqueous phase was extracted with two portions of ethyl acetate. The combined organic layers were washed with brine and concentrated in vacuo. Purification by flash chromatography (silica gel, 83:17 hexanes/ethyl acetate) afforded the desired product.

Step C: (4R)-3-[(2R,3S)-2-Bromo-3-(4-bromophenyl)butanoyl]-4-phenyl-1,3-oxazolidin-2-one To a stirred solution of the product from Step B (2.87 g, 7.39 mmol) in dichloromethane (40 mL) was added N,N-diisopropylethylamine (1.93 mL, 11.1 mmol) and dibutylborontriflate (9.6 mL, 1M solution in dichloromethane, 9.60 mmol) at −78° C. The light yellow solution was stirred at −78° C. for 15 min, 0° C. for 1 h and recooled to −78° C. for 15 min. The above solution was transferred to a precooled suspension of N-bromosuccinimide (3.93 g, 22.2 mmol) in dichloromethane (40 mL) via cannula. The resultant mixture was stirred at −78° C. for 1 h and 0° C. for 3 h. The reaction was quenched by addition of 0.5N aqueous sodium bisulfite solution. The organic phase was separated and the aqueous phase was extracted with two portions of ethyl acetate. The combined organic layers were washed with brine and concentrated in vacuo. Purification by flash chromatography (silica gel, 83:17 hexanes/ethyl acetate) afforded the desired product.

Step D: (4R)-3-[(2S,3S)-2-Azido-3-(4-bromophenyl)butanoyl]-4-phenyl-1,3-oxazolidin-2-one To a stirred solution of the product from Step C (2.71 g, 6.39 mmol) in acetonitrile (40 mL) was added tetramethylguanidinium azide (3.51 g, 22.2 mmol). The reaction was stirred at room temperature for 12 h. The solid was filtered off, and the filtrate was evaporated. The crude product was purified by flash chromatography (83:17 hexanes/ethyl acetate) to give the desired product.

Step E: (2S,3S)-2-Azido-3-(4-bromophenyl)butanoic acid

To a stirred solution of the product from Step D (2.77 g, 6.23 mmol) in THF (60 mL) was added water (20 mL). The solution was stirred at 0° C. for 15 min, and then 30% hydrogen peroxide (6.0 mL, 52.9 mmol) was added followed by slow addition of lithium hydroxide (0.50 g, 21.2 mmol). The resultant mixture was stirred at 0° C. for 4 h. The reaction was quenched by addition of saturated aqueous sodium sulfite solution and stirred at room temperature for 30 min. The aqueous phase was separated and washed with three portions of dichloromethane. The aqueous phase was then acidified to pH 1 with 3N hydrochloric acid and extracted with three portions of ethyl acetate. The ethyl acetate extracts were combined, dried over sodium sulfate, and evaporated in vacuo to give the product, which was used in the next step directly.

Step F: (3S)-1-[(2S,3S)-2-[(tert-Butoxycarbonyl)amino]-3-(4-bromophenyl)-1-oxobutanyl]-3-fluoropyrrolidine To 1.20 g (4.22 mmol) of the acid prepared in Step E dissolved in anhydrous DMF (10 mL) was added EDC (2.29 g, 11.9 mmol), HOBT (1.62 g, 11.9 mmol), (3S)-3-fluoropyrrolidine hydrochloride (Intermediate 1) (1.50 g, 11.9 mmol) and N,N-diisopropylethylamine (4.2 mL, 23.6 mmol). After stirring at room temperature for 12 h, the reaction was diluted with ethyl acetate. The organic phase was washed sequentially with brine, 1N aqueous hydrochloride acid and 1N aqueous sodium hydroxide solution, dried over sodium sulfate, and evaporated in vacuo to yield a yellow colored foam. To this foam was added 40 mL of dioxane, 4 mL of water and triphenylphosphine (4.70 g, 17.9 mmol). The reaction was heated at 90° C. for 12 h before it was cooled to room temperature. The solvent was removed in vacuo, and the residue was dissolved in 20 mL of dioxane and 20 mL of saturated aqueous sodium bicarbonate solution. To the resultant mixture was added 7.8 g of di-tert-butyldicarbonate (35.8 mmol). The reaction was stirred at room temperature for 12 h. The reaction mixture was diluted with ethyl acetate and acidified to pH 1 with 1N hydrochloric acid. The layers were separated, and the aqueous layer was extracted with two portions of ethyl acetate. The organic extracts were combined, washed with brine, dried over sodium sulfate, and concentrated in vacuo. Purification by flash chromatography (silica gel, 66:34 hexanes/ethyl acetate) afforded the desired product. LC/MS 429.1 (M+1).

Intermediate 7

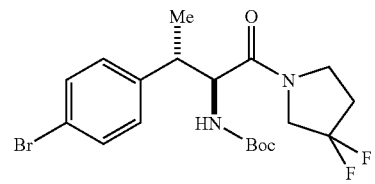

tert-Butyl {(1S,2S)-2-(4-bromophenyl)-1-[(3,3-difluoropyrrolidin-1-yl)carbonyl]propyl}carbamate The title compound was prepared using the procedures provided in the preparation of Intermediate 6, utilizing Intermediate 3 in Step F. LC/MS 469.2 (M+Na).

Intermediate 8

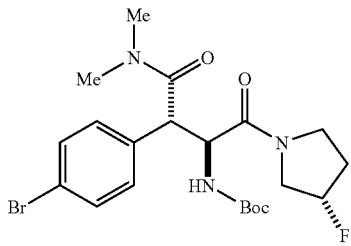

(3S)-1-[(2S,3S)-3-(4-Bromophenyl)-2-(tert-butoxy-carbonylamino)-3-(dimethylaminocarbonyl)-1-oxo-propanyl]-3-difluoropyrrolidine

Step A: trans-4-(4-Bromophenyl)-3-buten-2-one

To 25.0 g (110 mmol) of 4-bromocinnamic acid dissolved in anhydrous dichloromethane (500 mL) was added EDC (28.8 g, 150 mmol), HOBT (20.3 g, 150 mmol), N,O-dimethylhydroxylamine hydrochloride (14.6 g, 150 mmol) and N,N-diisopropylethylamine (23 mL, 150 mmol). After stirring at room temperature for 24 h, the reaction was concentrated then diluted with 400 mL of 10% aqueous hydrochloric acid. The resultant mixture was then extracted with three 300-mL portions of diethyl ether, the organic phases combined and washed sequentially with 10% hydrochloric acid, saturated aqueous sodium bicarbonate solution, and saturated aqueous brine (100 mL each). The organic phase was then dried over magnesium sulfate, filtered, and evaporated in vacuo to yield the Weinreb amide as a viscous oil that was used without further purification. To this oil was added 300 mL of anhydrous THF and the resultant solution was cooled to −78° C. To this solution was added 60 mL of methylmagnesium bromide (180 mmol, 3N in diethyl ether). The stirred mixture was allowed to warm slowly to 0° C. over 1 h. The mixture was then quenched carefully with water and 5% aqueous hydrochloric acid (100 mL each) then concentrated to remove the THF. The resultant mixture was extracted with three 300-mL portions of diethyl ether, the organic phases combined and washed sequentially with 5% hydrochloric acid, saturated aqueous sodium bicarbonate solution, and saturated aqueous brine (100 mL each). The organic phase was then dried over magnesium sulfate, filtered, and evaporated in vacuo to yield a viscous oil. The crude material was then purified by flash chromatography on a Biotage® system (silica gel, 0 to 15% ethyl acetate/hexanes gradient) to give the title compound as pale yellow crystalline solid. LC/MS 225.0 (M+1), 227.0 (M+3).

Step B: (2S,3E)-4-(4-Bromophenyl)-3-buten-2-ol

To 5.55 g (24.7 mmol) of the ketone from Step A dissolved in 100 mL of toluene was added 3.7 mL (3.7 mmol, 1M in toluene) of (R)-2-methyl-CBS-oxazaborolidine catalyst and the resultant mixture was stirred at ambient temperature for 15 min. The mixture was cooled to −78° C. and 4.0 mL (37.1 mmol) of catecholborane in 30 mL of toluene was added dropwise over 30 min. After the addition, the slurry was stirred at −78° C. for 60 min while slowly turning homogeneous. The solution was then stirred at −78° C. an additional 4 h (reaction time varies from 4-24 h) until TLC revealed complete disappearance of starting material. Next, the reaction mixture was diluted with 100 mL of water and the resultant mixture was extracted with three 100-mL portions of diethyl ether. The organic phases were then combined and washed with two 100-mL portions of 1N aqueous sodium hydroxide solution, two 100-mL portions of 5% hydrochloric acid solution, one 100-mL portion of saturated aqueous brine, dried over magnesium sulfate, filtered, and evaporated in vacuo to yield the crude waxy solid. The crude material was then purified by flash chromatography on a Biotage® system (silica gel, 0 to 20% ethyl acetate/hexanes gradient) to give the alcohol as a colorless crystalline solid. This compound was recrystallized in hexanes to yield the alcohol as colorless crystals (96% ee by Mosher ester analysis). LC/MS 209.0 (M-water+1), 211.0 (M-water+3).

Step C: (1S,2E)-3-(4-Bromophenyl)-1-methylprop-2-enyl N-(tert-butoxycarbonyl)glycinate To 12.6 g (55 mmol) of the alcohol from Step B dissolved in anhydrous dichloromethane (300 mL) was added EDC (23 g, 120 mmol), HOBT (16 g, 120 mmol), N-(tert-butoxycarbonyl)glycine (21 g, 120 mmol) and N,N-diisopropylethylamine (19 mL, 120 mmol). After 5 h, the mixture was concentrated and diluted with 200 mL of 10% aqueous hydrochloric acid. The resultant mixture was then extracted with three 300-mL portions of diethyl ether, the organic phases combined and washed sequentially with 5% hydrochloric acid, saturated aqueous sodium bicarbonate solution, and saturated aqueous brine (100 mL each). The organic phase was then dried over magnesium sulfate, filtered, and evaporated in vacuo to yield the crude material as a viscous oil. The crude material was purified by flash chromatography on a Biotage® system (silica gel, 0 to 20% ethyl acetate/hexanes gradient) to give the title compound as a colorless crystalline solid. LC/MS 328.1 (M-tBu+1), 330.1 (M-tBu+3).

Step D: Methyl(βS)-4-Bromo-N-(tert-butoxycarbonyl)-β-[(1E)-prop-1-enyl]-L-phenylalaninate The ester from Step C (18.1 g, 47 mmol) in anhydrous THF (50 mL) was added via cannula to 105 mL (105 mmol, 1M in THF) of lithium hexamethyldisilazide solution precooled to −78° C. After stirring for 10 min at that temperature, 55 mL of zinc chloride solution (55 mmol, 1M in diethyl ether) was added at −78° C. The resultant mixture was stirred at −78° C. for 5 h then allowed to warm slowly to room temperature over 3 h. After stirring an additional 2 h at room temperature, the mixture was quenched with water and 5% hydrochloric acid (100 mL each). The resultant mixture was then extracted with three 300-mL portions of ethyl acetate, the organic phases combined and washed sequentially with 5% hydrochloric acid, saturated aqueous sodium bicarbonate solution, and saturated aqueous brine (200 mL each). The organic phase was then dried over magnesium sulfate, filtered, and evaporated in vacuo to yield the crude material as a yellow foam. LC/MS 384.1 (M+1), 386.1 (M+3). This crude material was dissolved in 500 mL of 1:1 diethyl ether/methanol and cooled to 0° C. Trimethylsilyldiazomethane solution (75 mL, 150 mmol, 2M in hexanes) was added in portions until a yellow color persisted. After warming to room temperature, the solution was stirred an additional 8 h, then concentrated in vacuo. The crude material was purified by flash chromatography on a Biotage® system (silica gel, 0 to 15% ethyl acetate/hexanes gradient) to give the title compound as a colorless oil. LC/MS 298.0 (M-Boc+1), 300.0 (M-Boc+3).

Step E: (βS)-4-Bromo-N-(tert-butoxycarbonyl)-β-[(1E)-prop-1-enyl]-L-phenylalanine To a solution of 25 g (62.8 mmol) of methyl(□S)-4-bromo-N-(tert-butoxycarbonyl)-□-[(1E)-prop-1-enyl]-L-phenylalaninate (Step D) in 600 mL of THF was added in succession 200 mL of methanol and 200 mL (200 mmol) of 1N aqueous sodium hydroxide solution. The reaction mixture was stirred at ambient temperature for 3 h, and then the methanol and THF were removed under reduced pressure. To the aqueous mixture was added 250 mL of 1N hydrochloric acid and the mixture was extracted with ethyl acetate (3×300 mL). The combined organic extracts were washed with brine (300 mL) then dried over sodium sulfate, filtered, and concentrated in vacuo to afford the carboxylic acid, which was used without further purification in Step F below.

Step F: (3S)-1-[(2S,3S,4E)-3-(4-Bromophenyl)-2-(tert-butoxycarbonylamino)hex-4-enoyl]-3-fluoropyrrolidine To a solution of 2.00 g (5.21 mmol) of (PS)-4-bromo-N-(tert-butoxycarbonyl)-β-[(1E)-prop-1-enyl]-L-phenylalanine from Step E and 0.781 g (6.25 mmol) of (3S)-3-fluoropyrrolidine hydrochloride (Intermediate 1) in 50 mL of DMF were added 2.71 mL (15.6 mmol) of N,N-diisopropylethylamine, 0.774 g (5.73 mmol) of HOBT, and 1.10 g (5.73 mmol) of EDC. After 16 h at ambient temperature, the reaction was quenched by the addition of 200 mL of 0.5N aqueous sodium bicarbonate solution. The mixture was extracted with two 300-mL portions of ethyl acetate. The organic layers were washed with two additional 200-mL portions of 0.5 M aqueous sodium bicarbonate solution, brine, dried (magnesium sulfate) and concentrated in vacuo to give a clear oil. Purification by silica gel chromatography (20-50% ethyl acetate/hexanes gradient) afforded the title compound as a colorless oil. LC/MS 355.3 (M+1) and 357.3 (M+3).

Step G: (3S)-1-[(2S,3S)-3-(4-Bromophenyl)-2-(tert-butoxycarbonylamino)-3-(dimethylaminocarbonyl)-1-oxopanyl]-3-difluoropyrrolidine To solution of 2.37 g (11.1 mmol) of sodium periodate, 0.306 g (2.21 mmol) of potassium carbonate, and 0.087 g (0.550 mmol) of potassium permanganate in 30 mL of water was added 70 mL of tert-butanol at ambient temperature. The resulting suspension was added to a solution of 2.21 g (1.01 mmol) of (3S)-1-[(2S,3S,4E)-3-(4-bromophenyl)-2-(tert-butoxycarbonylamino)hex-4-enoyl]-3-fluoropyrrolidine from Step F in 20 mL of tert-butanol. The resulting mixture was then heated to 40° C. for 9 h. The mixture was then cooled to ambient temperature and poured onto 200 mL of 1 M aqueous sodium bisulfate solution. The resulting mixture was extracted with two 250-mL portions of ethyl acetate. The organic layers were washed with brine, dried (magnesium sulfate), and concentrated in vacuo to afford a yellow solid. This material was dissolved in 26 mL of DMF. To this solution was added 1.33 mL (2.65 mmol) of a 2.0 M solution of dimethylamine in THF, followed by 1.15 mL (6.63 mmol) of N,N-diisopropylethylamine, 0.328 g (2.43 mmol) of HOBT, and 0.466 g (2.43 mmol) of EDC. After stirring for 16 h at ambient temperature, the reaction was diluted with 100 mL of 0.5 M aqueous sodium bicarbonate solution. The mixture was extracted with two 250-mL portions of ethyl acetate. The organic layers were washed with an additional two 100-mL portions of 0.5 M aqueous sodium bicarbonate solution and brine, then dried (magnesium sulfate) and concentrated in vacuo affording a yellow oil. Purification by silica gel chromatography (0-10% methanol/ethyl acetate gradient) afforded the title compound as a yellow solid. LC/MS 385.8 (M+1) and 387.8 (M+3).

Intermediate 9

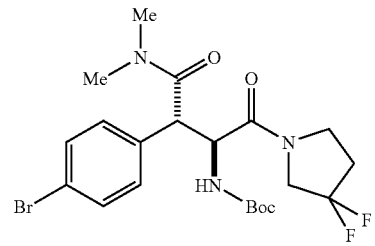

tert-Butyl[(1S,2S)-2-(4-bromophenyl)-1-[(3,3-difluoropyrrolidin-1-yl)carbonyl]-3-(dimethylamino)-3-oxopropyl]carbamate The title compound was prepared using the procedures outline in the preparation of Intermediate 8, utilizing Intermediate 3 in Step F. LC/MS 504.2 (M+1).

Intermediate 10

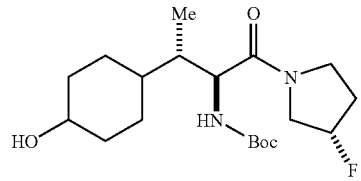

tert-Butyl[(1S,2S)-1-{[(3S)-3-fluoropyrrolidin-1-yl]carbonyl}-2-(4-hydroxycyclohexyl)propyl]carbamate

Step A: tert-Butyl {(1S,2S)-1-{[(3S)-3-fluoropyrrolidin-1-yl]carbonyl}-2-[4-(4,4,5,5-tetramethyl-1,3,2-dioxaborolan-2-yl)phenyl]propyl}carbamate A flask containing Intermediate 6 (0.50 g, 1.2 mmol), bis(pinacolato)diboron (0.59 g, 2.3 mmol), potassium acetate (0.34 g, 3.5 mmol), and [1,1'-bis(diphenylphosphino)ferrocene]dichloropalladium (II) (0.19 g, 0.23 mmol) was evacuated and then backfilled with nitrogen (3 times). DMSO (6 mL) was added and the resulting solution was heated at 90° C. for 14 h. The reaction mixture was cooled to ambient temperature and then poured into brine. The mixture was extracted with ethyl acetate, and the combined organic layers were washed with brine, dried (magnesium sulfate), and concentrated in vacuo. The residue was purified by silica gel chromatography (40% ethyl acetate in hexane) to give the title compound. LC/MS 499.4 (M+Na).

Step B: tert-Butyl[(1S,2S)-1-{[(3S)-3-fluoropyrrolidin-1-yl]carbonyl}-2-(4-hydroxyphenyl)propyl]carbamate To a solution of the material from Step A (0.5 g, 1.0 mmol) in THF (10 mL) at 0° C. was added sequentially 30% hydrogen peroxide (0.18 mL, 1.5 mmol) and 3N aqueous sodium hydroxide (0.35 g, 1.0 mmol). After 2 h at this temperature water (30 mL) was added, and the resulting solution was adjusted to pH 5 by the addition of 1N hydrochloric acid. The mixture was extracted with ethyl acetate, and the combined extracts were washed with saturated sodium thiosulfate until the organic phase showed a negative peroxide test. The combined organics were washed with brine, dried (magnesium sulfate), and concentrated in vacuo. The residue was purified by silica gel chromatography (50% ethyl acetate in hexane) to give the title compound as a white foam. LC/MS 389.3 (M+Na).

Step C: tert-Butyl[(1S,2S)-1-{[(3S)-3-fluoropyrrolidin-1-yl]carbonyl}-2-(4-hydroxycyclohexyl)propyl]carbamate The material from Step B (0.022 g, 0.060 mmol) was hydrogenated at 50 psi hydrogen in the presence of 5% rhodium on alumina (22 mg) in methanol (5 mL) using a Parr shaker. After 24 h, the reaction mixture was filtered by passage through a syringe filter. Concentration of the filtrate in vacuo afforded the title compound as a mixture of cis and trans isomers containing a small amount of the fully reduced cyclohexane. LC/MS 395.3 (M+Na)

Intermediate 11

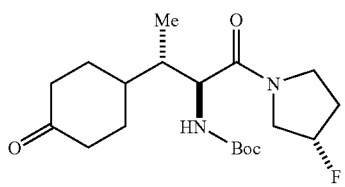

tert-Butyl[(1S,2S)-1-{[(3S)-3-fluoropyrrolidin-1-yl]carbonyl}-2-(4-oxocyclohexyl)propyl]carbamate To a solution of Intermediate 10 (0.024 g, 0.064 mmol) in dichloromethane (1.5 mL) was added a solution of 15 wt % of Dess-Martin periodinane in dichloromethane (0.17 g, 0.084 mmol). After 1 h, the reaction mixture was diluted with dichloromethane (4 mL), washed with saturated aqueous sodium bicarbonate, brine, dried (magnesium sulfate), and concentrated in vacuo. The residue was purified by silica gel chromatography (50% ethyl acetate in hexane, then 100% ethyl acetate) to give the title compound. LC/MS 393.3 (M+Na).

Intermediate 12

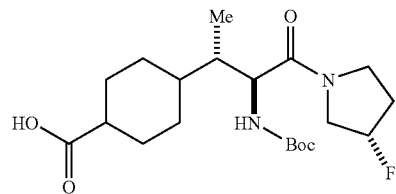

4-{(1S,2S)-2-[(tert-Butoxycarbonyl)amino]-3-[(3S)-3-fluoropyrrolidin-1-yl]-1-methyl-3-oxopropyl}cyclohexanecarboxylic acid

Step A: Butyl 4-{(1S,2S)-2-[(tert-butoxycarbonyl)amino]-3-[(3S)-3-fluoropyrrolidin-1-yl]-1-methyl-3-oxopropyl}benzoate To a solution of Intermediate 6 (3.0 g, 7.0 mmol) in anhydrous n-butanol (100 mL) was added triethylamine (30 mL) and [1,1'-bis(diphenylphosphino)ferrocene]-dichloropalladium (II) (0.57 g, 0.70 mmol). The mixture was purged with carbon monoxide gas, then heated to 90° C. under 1 atm carbon monoxide atmosphere for 24 h. The mixture was then cooled to ambient temperature and filtered through Celite, and the filter washed with ethyl acetate. The solution was concentrate in vacuo, and the residue was purified by silica gel chromatography (50% ethyl acetate in hexanes) affording the title compound as a beige solid. LC/MS 351.4 (M+1-Boc).

Step B: Butyl 4-{(1S,2S)-2-[(tert-butoxycarbonyl)amino]-3-[(3S)-3-fluoropyrrolidin-1-yl]-1-methyl-3-oxopropyl}cyclohexanecarboxylate To a solution of the material prepared in Step A (2.8 g, 6.1 mmol) in acetic acid (100 mL) was added solid platinum(IV) oxide (0.75 g). The mixture was placed under 3 atm of hydrogen gas at ambient temperature for 36 h. The mixture was filtered through Celite, and the resulting solution was concentrated in vacuo affording the title compound as a 2:1 mixture of cis and trans cyclohexyl diastereomers, which was used without further purification.

Step C: 4-{(1S,2S)-2-[(tert-Butoxycarbonyl)amino]-3-[(3S)-3-fluoropyrrolidin-1-yl]-1-methyl-3-oxopropyl}cyclohexanecarboxylic acid To a solution of the material prepared in Step B (3.0 g, 6.1 mmol) in THF (30 mL) was added methanol (10 mL) followed by 1N aqueous lithium hydroxide (30 mL). After 24 h at ambient temperature the mixture was brought to pH 1 with 1N aqueous sodium bisulfate. The mixture was extracted with 100 mL of ethyl acetate. The organic layer was washed with brine, dried (magnesium sulfate), and concentrated in vacuo, affording the title compound. This was used without further purification. LC/MS 406.2 (M+1).

Intermediate 13

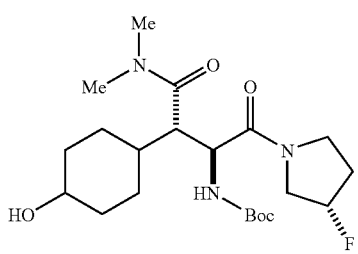

tert-Butyl[(1S,2S)-3-(dimethylamino)-1-{[(3S)-3-fluoropyrrolidin-1-yl]carbonyl}-2-(4-hydroxycyclohexyl)-3-oxopropyl]carbamate Step A: tert-Butyl {(1S,2S)-3-(dimethylamino)-1-{[(3S)-3-fluoropyrrolidin-1-yl]carbonyl}-3-oxo-2-[4-(4,4,5,5-tetramethyl-1,3,2-dioxaborolan-2-yl)phenyl]propyl}carbamate A flask containing Intermediate 8 (0.50 g, 1.0 mmol), bis(pinacolato)diboron (0.52 g, 2.0 mmol), potassium acetate (0.30 g, 3.1 mmol), and [1,1'-bis(diphenylphosphino)ferrocene]dichloropalladium (II) (0.17 g, 0.20 mmol) was evacuated and then backfilled with nitrogen (3 times). DMSO (5 mL) was added and the resulting solution was heated at 90° C. for 14 h. The reaction mixture was cooled to ambient temperature and then poured into brine. The mixture was extracted with ethyl acetate, and the combined organic layers were washed with brine, dried (magnesium sulfate), and concentrated in vacuo. The residue was purified by silica gel chromatography (0-10% methanol in dichloromethane gradient) to give the title compound. LC/MS 534.1 (M+1).

Step B: tert-Butyl[(1S,2S)-3-(dimethylamino)-1-{[(3S)-3-fluoropyrrolidin-1-yl]carbonyl}-2-(4-hydroxyphenyl)-3-oxopropyl]carbamate To a solution of the material from Step A (0.5 g, 0.94 mmol) in THF (10 mL) at 0° C. was added sequentially 30% hydrogen peroxide (0.16 mL, 1.4 mmol) and 3N aqueous sodium hydroxide (0.31 g, 0.94 mmol). After 1.5 h at this temperature, the mixture was allowed to warm to ambient temperature, and then water (50 mL) was added, and the resulting solution was adjusted to pH 5 by the addition of 1N hydrochloric acid. The mixture was extracted with ethyl acetate, and the combined extracts were washed with 10% aqueous sodium thiosulfate until the organic phase showed a negative peroxide test. The combined organics were washed with brine, dried (magnesium sulfate), and concentrated in vacuo. The residue was purified by silica gel chromatography (0-10% methanol in ethyl acetate) to give the title compound as a white foam. LC/MS 424.3 (M+1).

Step C: tert-Butyl[(1S,2S)-3-(dimethylamino)-1-{[(3S)-3-fluoropyrrolidin-1-yl]carbonyl}-2-(4-hydroxycyclohexyl)-3-oxopropyl]carbamate The material from Step B (0.33 g, 0.77 mmol) was hydrogenated at 50 psi hydrogen in the presence of 5% rhodium on alumina (0.33 g) in methanol (10 mL) using a Parr shaker. After 24 h, the reaction mixture was filtered by passage through a syringe filter. Concentration of the filtrate in vacuo afforded the title compound as a mixture of cis and trans isomers containing a small amount of the fully reduced cyclohexane. LC/MS 430.1 (M+1), 452.1 (M+Na).

Intermediate 14

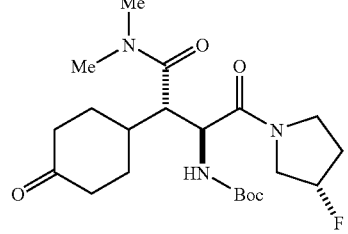

tert-Butyl[(1S,2S)-1-{[(3S)-3-fluoropyrrolidin-1-yl]carbonyl}-2-(4-oxocyclohexyl)propyl]carbamate To a solution of Intermediate 13 (0.024 g, 0.064 mmol) in dichloromethane (1.5 mL) was added a solution of 15 wt % of Dess-Martin periodinane in dichloromethane (0.17 g, 0.084 mmol). After 1 h, the reaction mixture was diluted with dichloromethane (4 mL), washed with saturated aqueous sodium bicarbonate, brine, dried (magnesium sulfate), and concentrated in vacuo. The residue was purified by silica gel chromatography (50% ethyl acetate in hexane, then 100% ethyl acetate) to give the title compound. LC/MS 393.3 (M+Na).

Intermediate 15

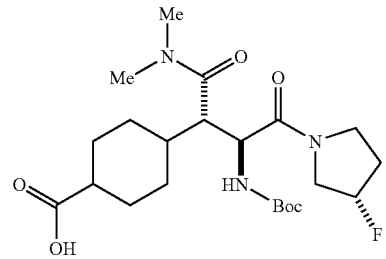

(2S,3S)-3-[(tert-Butoxylcarbonyl)amino]-4-[(3S)-3-fluoropyrrolidin-1-yl]-2-(4-carboxylcyclohexyl)-N,N-dimethyl-4-oxobutanamide Step A: (3S)-1-[(2S,3S)-3-4-(n-Butoxycarbonyl)phenyl-2-(tert-butoxycarbonylamino)-3-(dimethylaminocarbonyl)-1-oxopropanyl]-3-difluoropyrrolidine To a solution of Intermediate 8 (1.0 g, 2.1 mmol) in anhydrous n-butanol (100 mL) was added triethylamine (10 mL) and [1,1'-bis(diphenylphosphino)ferrocene]-dichloropalladium (II) (0.168 g, 0.21 mmol). The mixture was purged with carbon monoxide gas, then heated under 1 atm carbon monoxide atmosphere for 24 h. The mixture was then cooled to ambient temperature and filtered through Celite, and the filter washed with ethyl acetate. The solution was concentrated in vacuo, and the residue was purified by reversed phase liquid chromatography (30%-70% acetonitrile in water gradient) affording the title compound as a beige solid. LC/MS 408.3 (M+1-Boc).

Step B: (2S,3S)-3-[(tert-Butoxylcarbonyl)amino]-4-[(3S)-3-fluoropyrrolidin-1-yl]-2-[4-(n-butoxycarboxylcyclohexyl)]-N,N-dimethyl-4-oxobutanamide To a solution of the material from Step A (0.79 g, 1.6 mmol) in acetic acid (100 mL) was added platinum(IV) oxide (0.35 g). The mixture was placed under 3 atm of hydrogen for 36 h at ambient temperature. The mixture was then filtered through Celite, and concentrated in vacuo. Purification by silica gel chromatography (5% methanol in dichloromethane) afforded the title compound as a mixture of cis and trans cyclohexyl diastereomers as a colorless oil. LC/MS 514.4 (M+1).

Step C: (2S,3S)-3-[(tert-Butoxylcarbonyl)amino]-4-[(3S)-3-fluoropyrrolidin-1-yl]-2-(4-carboxylcyclohexyl)-N,N-dimethyl-4-oxobutanamide To a solution of the material from Step B (0.66 g, 1.3 mmol) in an 8:3 mixture of THF and water (11 mL) was added 1N aqueous lithium hydroxide solution (8 mL). After 48 h at ambient temperature, the reaction was adjusted to pH 1 by the addition of 1N aqueous sodium bisulfate. The mixture was diluted with ethyl acetate (100 mL), and the organic layer was washed with brine, dried (magnesium sulfate), and concentrated in vacuo, affording the title compound as a mixture of cis and trans cyclohexyl diastereomers as a colorless oil. LC/MS 359 (M+1-Boc).

Intermediate 16

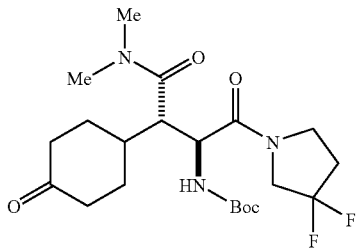

tert-Butyl[(1S,2S)-1-{[(3S)-3,3-difluoropyrrolidin-1-yl]carbonyl}-2-(4-oxocyclohexyl)propyl]carbamate The title compound was prepared using the procedures provided in the preparation of Intermediate 14, utilizing Intermediate 3. LC/MS 468.3 (M+Na).

Intermediate 17

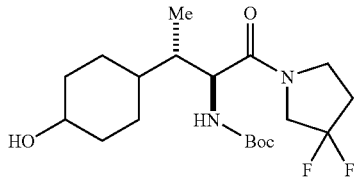

tert-Butyl[(1S,2S)-1-{[(3S)-3,3-difluoropyrrolidin-1-yl]carbonyl}-2-(4-hydroxycyclohexyl)propyl]carbamate The title compound was prepared using the procedures provided in the preparation of Intermediate 10, utilizing Intermediate 3. LC/MS 413.1 (M+Na).

Intermediate 18

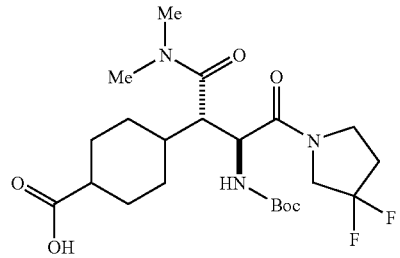

(2S,3S)-3-[(tert-Butoxylcarbonyl)amino]-4-[(3S)-3,3-difluoropyrrolidin-1-yl]-2-(4-carboxylcyclohexyl)-N,N-dimethyl-4-oxobutanamide The title compound was prepared using the procedures provided in the preparation of Intermediate 15, utilizing Intermediate 3.

Example 1

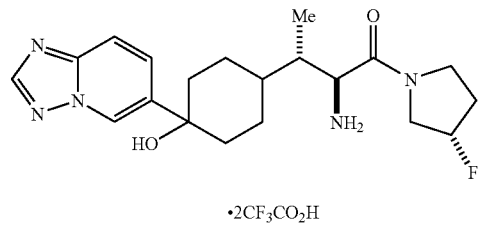

4-{(1S,2S)-2-Amino-3-[(3S)-3-fluoropyrrolidin-1-yl]-1-methyl-3-oxopropyl}-1-[1,2,4]triazolo[1,5-a]pyridin-6-ylcyclohexanol, bis(trifluoroacetic acid) salt Step A: N'-(5-Bromopyridin-2-yl)-N,N-dimethylimidoformamide To a stirred solution of 5-bromo-2-aminopyridine (3.0 g, 17.3 mmol) in N,N-dimethylformamide (6 mL) was added N,N-dimethylformamide dimethyl acetal (5.37 g, 45.0 mmol). The reaction mixture was heated to 130° C. overnight. After cooling to room temperature, the volatiles were removed under reduced pressure to afford the desired product as a brown oil. LC/MS 227.8 (M+1).

Step B: 6-Bromo[1,2,4]triazolo[1,5-a]pyridine

To an ice-cooled, stirred solution of the crude product from Step A (3.94 g, 17.3 mmol) in methanol (30 mL) and pyridine (2.73 g, 35.6 mmol) was added hydroxylamine-O-sulfonic acid (2.54 g, 22.5 mmol). The reaction mixture was allowed to warm to room temperature and was stirred overnight. The volatiles were removed under reduced pressure, and the residue was partitioned between aqueous sodium bicarbonate solution and ethyl acetate. The aqueous layer was further extracted with ethyl acetate, and the combined organic layers were washed sequentially with water (100 mL) and saturated aqueous brine solution (100 mL), dried (magnesium sulfate) and concentrated in vacuo to yield a brown solid, which was recrystallized from dichloromethane to afford the title compound as an orange solid. LC/MS 197.9 and 199.9 (M+1).

Step C: tert-Butyl[(1S,2S)-1-{[(3S)-3-fluoropyrroli-din-1-yl]carbonyl}-2-(4-hydroxy-4-[1,2,4]triazolo[1,5-a]pyridin-6-ylcyclohexyl)propyl]carbamate To a solution of 6-bromo[1,2,4]triazolo[1,5-a]pyridine prepared in Step B (0.11 g, 0.56 mmol) in THF (1.8 mL) at −78° C. was added a solution of n-butyllithium in hexane (2.4 M, 0.45 mL, 1.1 mmol). The resulting solution was stirred at −78° C. for 40 min, whereupon Intermediate 11 (0.068 g, 0.18 mmol) was added as a solution in THF (1 mL). After an additional 1 h at −78° C., saturated aqueous ammonium chloride was added and the mixture was allowed to warm to ambient temperature. A small amount of water was added and the mixture was extracted with ethyl acetate. The combined organic layers were washed with brine, dried (anhydrous sodium sulfate), and concentrated in vacuo. The residue was purified by preparative thin layer chromatography to deliver the title compound. LC/MS 512.5 (M+Na), 390.4 (M+1-Boc), 372.4 (M+1-Boc-water).

Step D: 4-{(1S,2S)-2-Amino-3-[(3S)-3-fluoropyrrolidin-1-yl]-1-methyl-3-oxopropyl}-1-[1,2,4]triazolo[1,5-a]pyridin-6-ylcyclohexanol, bis(trifluoroacetic acid) salt To a solution of the material from Step C (0.005 g, 0.010 mmol) in dichloromethane (2 mL) was added trifluoroacetic acid (1 mL). After 0.5 h at ambient temperature the reaction mixture was concentrated in vacuo. The crude product was purified by reverse phase HPLC (10-50% acetonitrile in water gradient). Lyophilization of the appropriate fractions afforded the title compound as a mixture of cis and trans isomers. LC/MS 390.4 (M+1), 412.4 (M+Na), 372.4 (M+1-water).

Example 2

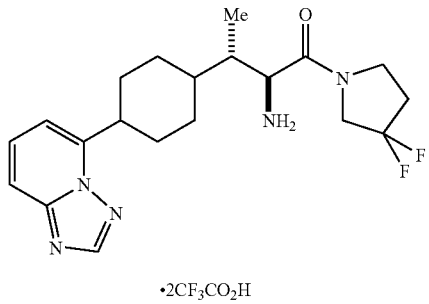

·2CF₃CO₂H (2S,3S)-1-(3,3-Difluoropyrrolidin-1-yl)-1-oxo-3-(4-[1,2,4]triazolo[1,5-a]pyridin-5-ylcyclohexyl)butan-2-amine, bis(trifluoroacetic acid) salt Step A: tert-Butyl[(1S,2S)-1-[(3,3-difluoropyrrolidin-1-yl)carbonyl]-2-(4-hydroxy-4-[1,2,4]triazolo[1,5-a]pyridin-5-ylcyclohexyl)propyl]carbamate To a solution of [1,2,4]triazolo[1,5-a]pyridine (0.067 g, 0.56 mmol) in THF (4 mL) at −78° C. was added a solution of n-butyllithium in hexane (3.2 M, 0.18 mL, 0.57 mmol). After 30 min at this temperature, Intermediate 11 (0.10 g, 0.26 mmol) was added as a solution in THF (1 mL). The reaction mixture was allowed to warm to 0° C. After 0.5 h at 0° C., water was added and the mixture was extracted with ethyl acetate. The combined organic layers were dried (anhydrous sodium sulfate) and concentrated. The residue was purified by silica gel chromatography (0-5% methanol in dichloromethane gradient) to afford the title compound. LC/MS 530.1 (M+Na).

Step B: tert-Butyl[(1S,2S)-1-[(3,3-difluoropyrrolidin-1-yl)carbonyl]-2-(4-[1,2,4]triazolo[1,5-a]pyridin-5-ylcyclohex-3-en-1-yl)propyl]carbamate To a solution of the compound prepared in Step A (0.13 g, 0.26 mmol) in THF (5 mL) was added Burgess reagent (0.19 g, 0.78 mmol). After 1 h at ambient temperature, the reaction mixture was concentrated to 1 mL in vacuo. The remaining solution was added to saturated aqueous sodium bicarbonate and the resulting mixture was extracted with dichloromethane. The combined organic layers were dried (anhydrous sodium sulfate) and concentrated in vacuo to give the title compound. LC/MS 490.4 (M+1).

Step C: tert-Butyl[(1S,2S)-1-[(3,3-difluoropyrrolidin-1-yl)carbonyl]-2-(4-[1,2,4]triazolo[1,5-a]pyridin-5-ylcyclohexyl)propyl]carbamate The material from Step B (0.13 g, 0.27 mmol) was hydrogenated at 50 psi hydrogen in the presence of 10% palladium on carbon (0.13 g) in methanol (5 mL) containing 30 drops of acetic acid using a Parr shaker. After 1 h, the reaction mixture was filtered by passage through a syringe filter. The filtrate was concentrated and the residue was dissolved in chloroform and washed with saturated aqueous sodium bicarbonate. The organic layer was dried (anhydrous sodium sulfate) and concentrated in vacuo. The residue was purified by silica gel chromatography (0-5% methanol in dichloromethane) gradient to afford the title compound. LC/MS 492.1 (M+1).

Step D: (2S,3S)-1-(3,3-Difluoropyrrolidin-1-yl)-1-oxo-3-(4-[1,2,4]triazolo[1,5-a]pyridin-5-ylcyclohexyl)butan-2-amine, bis(trifluoroacetic acid) salt To a solution of the material from Step C (0.050 g, 0.10 mmol) in dichloromethane (3 mL) at ambient temperature was added trifluoroacetic acid (1 mL). After 1 h, the reaction mixture was concentrated in vacuo. The residue was purified by reverse phase HPLC (10-40% acetonitrile in water gradient). Lyophilization of the appropriate fractions afforded the title compound as a mixture of cis and trans isomers. LC/MS 392.1 (M+1).

Following the procedures outlined in Example 2, and using the appropriate intermediate, Examples 3-6 listed in Table 1 were prepared.

TABLE 1

![Structure with R2, R3, NH2, and thiazolidine group]

| Example | R³ | R² | X | MS (M+1) |
|---------|-----|------|--------|----------|
| 3 | 4-fluorophenyl | Me | (S)-CHF | 351.3 |
| 4 | 4-fluorophenyl | CONMe₂ | (S)-CHF | 408.3 |
| 5 | [1,2,4]triazolo[1,5-a]pyridin-6-yl | CONMe₂ | (S)-CHF | 431.1 |
| 6 | [1,2,4]triazolo[1,5-a]pyridin-6-yl | CONMe₂ | CF₂ | 449.4 |

Example 7

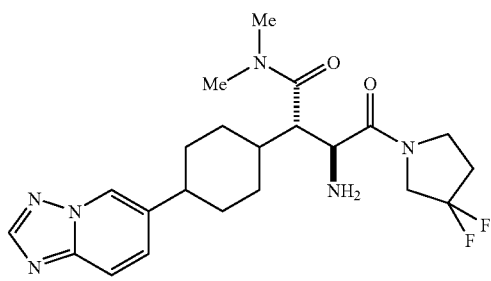

·2CF₃CO₂H (2S,3S)-3-Amino-4-(3,3-difluoropyrrolidin-1-yl)-N,
N-dimethyl-4-oxo-2-(4-[1,2,4]triazolo[1,5-a]pyridin-
6-ylcyclohexyl)butanamide, bis trifluoroacetic acid
salt Step A: 4-{(1S,2S)-2-[(tert-Butoxycarbonyl)amino]-
3-(3,3-difluoropyrrolidin-1-yl)-1-[(dimethylamino)
carbonyl]-3-oxopropyl}cyclohex-1-en-1-yl trifluo-
romethanesulfonate To a solution of Intermediate 16 (2.5 g, 5.7 mmol) in THF (57 mL) at −78° C. was added a solution of lithium hexamethyldisilazide in THF (1.0 M, 12.6 mL, 12.6 mmol). After 2 h at −78° C., a solution of N-phenyltrifluoromethanesulfonimide (2.1 g, 6.0 mmol) in THF (5 mL) was added. The reaction mixture was allowed to warm slowly to ambient temperature and then stirred overnight. Water was added and the mixture was extracted with ethyl acetate and the combined organic layers were washed with 1N sodium hydroxide, water, brine, dried (magnesium sulfate), and concentrated in vacuo. The residue was purified by silica gel chromatography (3% methanol in dichloromethane) to afford the title compound. LC/MS 578.2 (M+1).

Step B: tert-Butyl {(1S,2S)-1-[(3,3-difluoropyrroli-
din-1-yl)carbonyl]-3-(dimethylamino)-3-oxo-2-[4-(4,
4,5,5-tetramethyl-1,3,2-dioxaborolan-2-yl)cyclohex-
3-en-1-yl]propyl}carbamate The material from Step A (3.0 g, 5.1 mmol) was combined with bis(pinacolato)diboron (1.4 g, 5.4 mmol), [1,1'-bis(diphenylphosphino)ferrocene]dichloropalladium (II) (0.84 g, 1.0 mmol), diphenylphosphinoferrocene (0.57 g, 1.0 mmol), and potassium acetate (1.5, 15 mmol) and the flask was flushed with nitrogen. Dioxane (36 mL) was added, and the resulting mixture was heated at 80° C. for 14 h. The reaction mixture was cooled to ambient temperature and then partitioned between brine and ethyl acetate. The layers were separated and the aqueous phase was extracted with ethyl acetate. The combined organic layers were washed with brine, dried (magnesium sulfate), and concentrated in vacuo. The residue was purified by silica gel chromatography (10-30% acetone in hexane gradient) to afford the title compound. LC/MS 556.3 (M+1).

Step C: tert-Butyl[(1S,2S)-1-[(3,3-difluoropyrroli-
din-1-yl)carbonyl]-3-(dimethylamino)-3-oxo-2-(4-[1,
2,4]triazolo[1,5-a]pyridin-6-ylcyclohex-3-en-1-yl)
propyl]carbamate The material from Step B (2.0 g, 3.6 mmol) was combined with [1,1'-bis(diphenylphosphino)ferrocene]dichloropalladium (II) (0.43 g, 0.53 mmol), potassium carbonate (1.5 g, 11 mmol), and 6-bromo[1,2,4]triazolo[1,5-a]pyridine (80% pure, 1.1 g, 4.3 mmol) and the flask was flushed with nitrogen. DMF (35 mL) was added, and the resulting mixture was heated at 80° C. for 14 h. The reaction mixture was diluted with ethyl acetate and washed with water. The aqueous layer was extracted with ethyl acetate and the combined organic extracts were washed with brine, dried (anhydrous sodium sulfate), and concentrated in vacuo. The residue was purified by silica gel chromatography twice (0-5% methanol in dichloromethane, then 0-5% methanol in ethyl acetate) to afford the title compound. LC/MS 547.3 (M+1).

Step D: tert-Butyl[(1S,2S)-1-[(3,3-difluoropyrroli-
din-1-yl)carbonyl]-3-(dimethylamino)-3-oxo-2-(4-[1,
2,4]triazolo[1,5-a]pyridin-6-ylcyclohexyl)propyl]
carbamate The material from Step C (0.79 g, 1.5 mmol) was placed under 1 atmosphere of hydrogen gas in the presence of 10% palladium on carbon (1.6 g) in methanol (40 mL). After 24 h, the reaction mixture was filtered and the filtrate was concentrated in vacuo to give a mixture of cis and trans diastereomers. These diastereomers were separated by chiral HPLC (Chiralcel OD column eluting with 20% isopropanol in heptane) to afford the title compounds as single isomers (Analytical retention times: Diastereomer A $T_r$=11.8 min, Diastereomer B $T_r$=13.9 min. LC/MS 549.3 (M+1).

Step E: (2S,3S)-3-Amino-4-(3,3-difluoropyrrolidin-1-yl)-N,N-dimethyl-4-oxo-2-(4-[1,2,4]triazolo[1,5-a]pyridin-6-ylcyclohexyl)butanamide, bis trifluoroacetic acid salt Diastereomer A: To a solution of the faster eluting diastereomer (Diastereomer A) (0.009 g, 0.016 mmol) from Step D in dichloromethane (3 mL) was added trifluoroacetic acid (1 mL). After 0.75 h at ambient temperature, additional trifluoroacetic acid (0.5 mL) was added. When the reaction was complete by LC/MS analysis, the reaction mixture was concentrated in vacuo. The residue was purified by reverse phase HPLC (5-35% acetonitrile in water gradient). Lyophilization of the appropriate fractions afforded the title compound as a single isomer (1:1 mixture of rotamers). $^1$H NMR (500 MHz, CD$_3$OD): δ 8.70 (m, 1H), 8.45 (m, 1H), 7.76 (app s, 2H), 4.44 (d, J=7.3 Hz, 0.5H), 4.33 (d, J=7.8 Hz, 0.5H), 4.14-3.95 (m, 2H), 3.88-3.81 (m, 1H), 3.76-3.56 (m, 2H), 3.48 (t, J=6.7 Hz, 0.5H), 3.44 (t, J=6.2 Hz, 0.5H), 3.11 (s, 1.5H), 3.10 (s, 1.5H), 2.86 (s, 1.5H), 2.85 (s, 1.5H), 2.52-2.37 (m, 2H), 2.23-2.20 (m, 2H), 2.03-1.92 (m, 3H), 1.77-1.75 (m, 2H), 1.61-1.57 (m, 1H), 1.49-1.42 (m, 1H); LC/MS 449.3 (M+1).

Diastereomer B: To a solution of the slower eluting diastereomer (Diastereomer B) (0.019 g, 0.035 mmol) from Step D in dichloromethane (3 mL) was added trifluoroacetic acid (1 mL). After 0.75 h at ambient temperature, additional trifluoroacetic acid (0.5 mL) was added. When the reaction was complete, the reaction mixture was concentrated in vacuo. The residue was purified by reverse phase HPLC (5-35% acetonitrile in water gradient). Lyophilization of the appropriate fractions afforded the title compound as a single isomer (1:1 mixture of rotamers). $^1$H NMR (500 MHz, CD$_3$OD): δ 8.63 (s, 1H), 8.43-8.42 (m, 1H), 7.75 (d, J=9.2 Hz, 1H), 7.70 (d, J=9.2 Hz), 4.49 (d, J=8.2 Hz, 0.5H), 4.37 (d, J=8.5. Hz, 0.5H), 4.22-4.14 (m, 0.5H), 4.09-4.01 (m, 1H), 3.90-3.79 (m, 1H), 3.76-3.67 (m, 1H), 3.63-3.57 (m, 1H), 3.53-3.49 (m 1H), 3.14 (s, 1.5H), 3.14 (s, 1.5H), 2.95 (s, 1.5H), 2.95 (s, 1.5H), 2.69 (br t, J=8.7 Hz, 1H) 2.54-2.37 (m, 2H) 2.06-1.86 (m, 5H), 1.67-1.55 (m, 3H), 1.42-1.34 (m, 1H); LC/MS 449.3 (M+1).

Following the procedures outlined in Example 7, Examples 8 and 9 listed in Table 2 were prepared.

TABLE 2

| Example | R$^3$ | R$^2$ | MS (M + 1) |
|---|---|---|---|
| 8 | 4-fluorophenyl | CONMe$_2$ | 426.2 |
| 9 | pyridin-3-yl | Me | 352.4 |

Example 10

4-[(1S,2S)-2-Amino-3-(3,3-difluoropyrrolidin-1-yl)-1-methyl-3-oxopropyl]cyclohexyl diethylcarbamate, trifluoroacetic acid salt Step A: 4-[(1S,2S)-2-[(tert-Butoxycarbonyl)amino]-3-(3,3-difluoropyrrolidin-1-yl)-1-methyl-3-oxopropyl]cyclohexyl diethylcarbamate The cis and trans isomers of Intermediate 17 were separated by chiral HPLC (Chiracel AS column, 5% isopropanol in heptane) and the second eluting diastereomer was carried on. A solution of this compound (0.015 g, 0.038 mmol), diethylcarbamoyl chloride (0.010 mL, 0.076 mmol), and 4-dimethylaminopyridine (spatula tip) in pyridine (1.5 mL) was heated at 115° C. Additional diethylcarbamoyl chloride and 4-dimethylaminopyridine were added periodically until the reaction was complete. The reaction mixture was concentrated in vacuo, and the residue was purified by reverse phase HPLC (10-100% acetonitrile in water gradient). The title compound was obtained by extraction of the appropriate fractions with ethyl acetate followed by drying (magnesium sulfate) and concentration in vacuo. LC/MS 512.0 (M+Na).

Step B: 4-[(1S,2S)-2-Amino-3-(3,3-difluoropyrrolidin-1-yl)-1-methyl-3-oxopropyl]cyclohexyl diethylcarbamate, trifluoroacetic acid salt To a solution of the material obtained in Step A (0.0055 g, 0.011 mmol) in dichloromethane (1.5 mL) was added trifluoroacetic acid (0.5 mL). After 1 h at ambient temperature, the reaction mixture was concentrated in vacuo. The residue was purified by reverse phase HPLC (20-40% acetonitrile in water gradient). Lyophilization of the appropriate fractions afforded the title compound. LC/MS 390.5 (M+1), 412.5 (M+Na).

Example 11

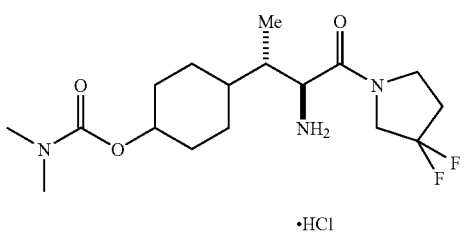

·HCl

4-[(1S,2S)-2-Amino-3-(3,3-difluoropyrrolidin-1-yl)-1-methyl-3-oxopropyl]cyclohexyl dimethylcarbamate, hydrochloride salt A procedure similar to the one used in Example 10 was employed utilizing dimethylcarbamoyl chloride in the preparation of the title compound. LC/MS 362.8 (M+1), 384.7 (M+Na).

Example 12

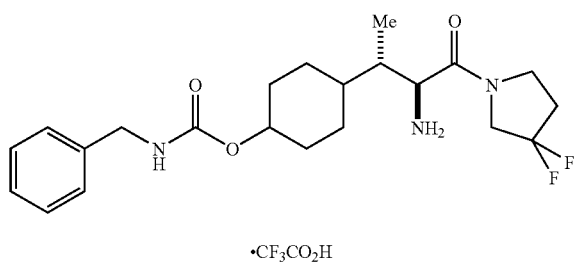

·CF₃CO₂H

4-[(1S,2S)-2-Amino-3-(3,3-difluoropyrrolidin-1-yl)-1-methyl-3-oxopropyl]cyclohexyl benzylcarbamate, trifluoroacetic acid salt Step A: 4-[(1S,2S)-2-[(tert-Butoxycarbonyl)amino]-3-(3,3-difluoropyrrolidin-1-yl)-1-methyl-3-oxopropyl]cyclohexyl benzylcarbamate To a solution of Intermediate 17 (0.050 g, 0.13 mmol) in dichloromethane (1.2 mL) was added pyridine (0.020 mL, 0.25 mmol) and benzyl isocyanate (0.020 mL, 0.16 mmol). Additional portions of pyridine and benzyl isocyanate were added periodically until the reaction was complete. The reaction mixture was diluted with ethyl acetate and washed with 0.5N aqueous hydrochloric acid, water, and brine, dried (magnesium sulfate), and concentrated in vacuo. The residue was purified by silica gel chromatography eluting with 30-70% ethyl acetate in hexane gradient. Concentration of the appropriate fractions gave the title compound as a mixture of cis and trans diastereomers. These diastereomers were separated by chiral HPLC (Chiralcel OD column eluting with 10% isopropanol in heptane) to afford the title compounds as single isomers: The faster eluting diastereomer: LC/MS 546.5 (M+Na). The slower eluting diastereomer: LC/MS 546.5 (M+Na).

Step B: 4-[(1S,2S)-2-Amino-3-(3,3-difluoropyrrolidin-1-yl)-1-methyl-3-oxopropyl]cyclohexyl benzylcarbamate, trifluoroacetic acid salt To a solution of the faster eluting diastereomer from Step A (0.012 g, 0.023 mmol) in dichloromethane (1.5 mL) was added trifluoroacetic acid (0.5 mL). After 1 h at ambient temperature, the reaction mixture was concentrated in vacuo. The residue was dissolved in 1:1 acetonitrile/water (+0.1% trifluoroacetic acid) and lyophilized to give the title compound. LC/MS 424.4 (M+1), 446.4 (M+Na).

Following the procedures outlined in Example 12, Examples 13-15 listed in Table 3 were prepared.

TABLE 3

| Example | R³ | MS (M + 1) |
|---|---|---|
| 13 | 2,4-dichlorobenzyl-NH-C(O)-O- | 492.3 |
| 14 | 4-(trifluoromethyl)phenyl-NH-C(O)-O- | 478.4 |
| 15 | ethyl-NH-C(O)-O- | 362.3 |

Example 16

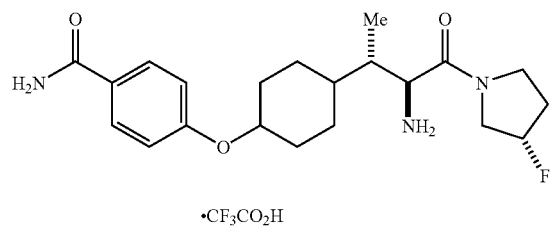

·CF₃CO₂H

4-[(4-{(1S,2S)-2-Amino-3-[(3S)-3-fluoropyrrolidin-1-yl]-1-methyl-3-oxopropyl}cyclohexyl)oxy]benzamide, trifluoroacetic acid salt Step A: tert-Butyl((1S,2S)-2-{4-[4-(aminocarbonyl)phenoxy]cyclohexyl}-1-{[(3S)-3-fluoropyrrolidin-1-yl]carbonyl}propyl)carbamate To a solution of Intermediate 10 (0.068 g, 0.18 mmol) in THF (1 mL) at 0° C. was added triphenylphosphine (0.072 g, 0.27 mmol) followed by 4-hydroxybenzamide (0.037 g, 0.27 mmol) and diisopropyl azodicarboxylate (0.054 mL, 0.27 mmol). The resulting solution was allowed to warm to ambient temperature. After 14 h the reaction mixture was concentrated in vacuo and the residue was purified by preparative TLC eluting with 70% ethyl acetate in hexane to afford a mixture of cis and trans isomers. These diastereomers were separated by chiral HPLC (Chiralcel OJ column eluting with 20% ethanol in hexane) to afford the faster eluting diastereomer as a pure isomer. LC/MS 392.3 (M+1-Boc).

Step B: 4-[(4-{(1S,2S)-2-Amino-3-[(3S)-3-fluoropyrrolidin-1-yl]-1-methyl-3-oxopropyl}cyclohexyl)oxy]benzamide, trifluoroacetic acid salt To a solution of the faster eluting diastereomer from Step A (0.0083 g, 0.017 mmol) in dichloromethane (1.5 mL) was added trifluoroacetic acid (0.1 mL). After 1 h at ambient temperature, an additional portion of trifluoroacetic acid was added. After an additional 1 h, the reaction mixture was concentrated in vacuo. The residue was purified by reverse phase HPLC (10-70% acetonitrile in water gradient). Lyophilization of the appropriate fractions afforded the title compound. LC/MS 392.1 (M+1).

Example 17

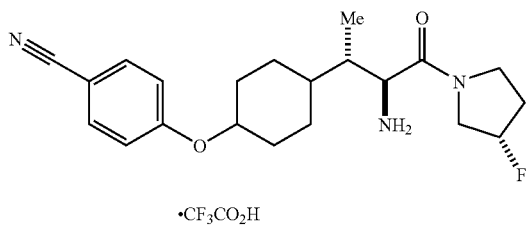

(2S,3S)-3-[4-(4-cyanophenoxy)cyclohexyl]-1-[(3S)-3-fluoropyrrolidin-1-yl]-1-oxobutan-2-aminium trifluoroacetate The compound was prepared in a fashion similar to Example 16. LC/MS 374.0 (M+1).

Example 18

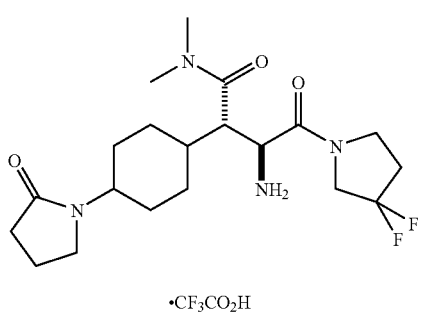

(2S,3S)-1-(3,3-Difluoropyrrolidin-1-yl)-4-(dimethylamino)-1,4-dioxo-3-[4-(2-oxopyrrolidin-1-yl)cyclohexyl]butan-2-aminium trifluoroacetate Step A: (2S,3S)-3-[(tert-Butoxycarbonyl)amino]-4-(3,3-difluoropyrrolidin-1-yl)-N,N-dimethyl-4-oxo-2-[4-(2-oxopyrrolidin-1-yl)phenyl]butanamide To a solid mass of copper iodide (0.019 g, 0.099 mmol) and potassium carbonate (0.29 g, 2.1 mmol) was added a solution of Intermediate 9 (0.50 g, 0.99 mmol), pyrrolidine-2-one (0.29 g, 1.2 mmol), and N,N'-dimethylethylenediamine (0.022 mL, 0.20 mmol) in 3 mL of toluene under a nitrogen atmosphere. The vessel was sealed and the mixture was heated to 100° C. for 72 h. The mixture was then cooled to ambient temperature and diluted with 200 mL of ethyl acetate. The mixture was washed with saturated aqueous sodium bicarbonate and brine. The organic layer was dried (magnesium sulfate) and concentrated in vacuo. Purification by flash chromatography on silica gel (5%-10% methanol in ethyl acetate gradient) afforded the title compound as a clear oil. LC/MS 509.5 (M+1).

Step B: (2S,3S)-3-[(tert-Butoxycarbonyl)amino]-4-(3,3-difluoropyrrolidin-1-yl)-N,N-dimethyl-4-oxo-2-[4-(2-oxopyrrolidin-1-yl)cyclohexyl]butanamide To a solution of the material prepared in Step A (0.46 g, 0.91 mmol) in 100 mL of acetic acid was placed solid platinum (IV) oxide (200 mg). The mixture was placed under 3 atm hydrogen for 24 h at ambient temperature. The mixture was then filtered through Celite, and concentrated in vacuo. Purification by reverse phase liquid chromatography (25%-65% acetonitrile in water gradient) afforded the title compound as a mixture of cis and trans 1,4-disubstituted cyclohexyl diastereomers. These diastereomers were separated by chiral HPLC (Chiracel OD column, 5% ethanol in hexanes) affording each pure diastereomer: The faster eluting diastereomer: LC/MS 514.4 (M+1); the slower eluting diastereomer: LC/MS 414.4 (M+1-Boc).

Step C: (2S,3S)-1-(3,3-Difluoropyrrolidin-1-yl)-4-(dimethylamino)-1,4-dioxo-3-[4-(2-oxopyrrolidin-1-yl)cyclohexyl]butan-2-aminium trifluoroacetate (the slower eluting diastereomer)

The slower eluting diastereomer from Step B was treated with 3 mL of hydrogen chloride (4 M in Et$_2$O). After 75 min at ambient temperature the solution was concentrated in vacuo. The crude product was purified by reverse phase liquid chromatography (10%-25% acetonitrile in water gradient) affording the title compound as a white solid. $^1$H NMR (500 MHz, CD$_3$OD): δ 4.43 (d, J=8.5 Hz, 1H), 4.31 (s, J=8.5 Hz, 1H), 4.12 (q, J=11.5 Hz, 1H), 4.04 (m, 2H), 3.85 (m, 2H), 3.70 (m, 5H), 3.56 (m, 2H), 3.47 (m, 2H), 3.41 (t, J=7.0 Hz, 2H), 3.10 (s, 3H), 2.92 (s, 3H), 2.50 (m, 2H), 2.42 (m, 2H), 2.35 (t, 2H, J=6.0 Hz, 3H), 2.00 (quint., J=5.5 Hz, 2H), 1.80 (m, 2H), 1.71 (m, 2H), 1.57 (m, 2H), 1.50 (m, 2H), 1.29 (m, 2H); LC/MS 415.4 (M+1).

Following the procedures outlined in Example 18, and using the appropriately R$^2$ substituted intermediate (either Intermediate 7 or Intermediate 9), Examples 19-22 listed in Table 4 were prepared.

TABLE 4

| Example | R³ | R² | MS (M + 1) |
|---|---|---|---|
| 19 | Me-N⟨imidazolidin-2-one⟩N- | CONMe₂ | 430.2 |
| 20 | ⟨piperidin-2-one⟩N- | CONMe₂ | 429.4 |
| 21 | ⟨oxazolidin-2-one⟩N- | CONMe₂ | 417.1 |
| 22 | Me-C(O)-N(Me)- | Me | 346.4 |

Example 23

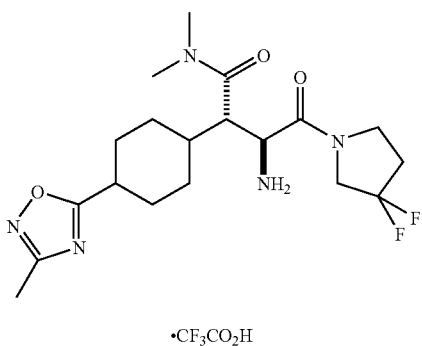

·CF₃CO₂H (2S,3S)-1-(3,3-Difluoropyrrolidin-1-yl)-4-(dimethylamino)-3-[4-(3-methyl-1,2,4-oxadiazol-5-yl)cyclohexyl]-1,4-dioxobutan-2-aminium trifluoroacetate Step A (2S,3S)-4-(3,3-Difluoropyrrolidin-1-yl)-3-[(tert-butoxylcarbonyl)amino]-N,N-dimethyl-2-[4-(3-methyl-1,2,4-oxadiazol-5-yl)cyclohexyl]-4-oxobutanamide To a solution of Intermediate 18 (0.071 g, 0.15 mmol) in acetonitrile (10 mL) was added HOBT (0.030 g, 0.22 mmol) and EDC (0.043 g, 0.22 mmol). The solution was stirred at ambient temperature for 4 h, followed by addition of (1Z)-N'-hydroxyethanimidamide (0.055 g, 0.74 mmol). The resulting solution was stirred for an additional 3 h at ambient temperature, then concentrated in vacuo. The resulting solid was dissolved in diglyme (8 mL) and heated to 100° C. for 18 h. The solution was again concentrated in vacuo. The resulting solid was purified by reverse phase liquid chromatography (20%-80% acetonitrile in water gradient) affording the title compound as a mixture of cis and trans disubstituted cyclohexyl diastereomers. These diastereomers were separated by chiral HPLC (Chiracel OD column, 3% ethanol in hexanes) affording each pure diastereomer: The faster eluting diastereomer: LC/MS 536.5 (M+Na); the slower eluting diastereomer: LC/MS 536.4 (M+Na).

Step B: (2S,3S)-1-(3,3-Difluoropyrrolidin-1-yl)-4-(dimethylamino)-3-[4-(3-methyl-1,2,4-oxadiazol-5-yl)cyclohexyl]-1,4-dioxobutan-2-aminium trifluoroacetate To a solution of the faster eluting diastereomer from Step A (0.032 g, 0.062 mmol) in dichloromethane (2 mL) was added trifluoroacetic acid (2 mL). The solution was stirred at ambient temperature for 1 h, and then concentrated in vacuo to afford the title compound as a white solid. ¹H NMR (500 MHz, CD₃OD): δ 4.45 (d, J=8.5 Hz, 1H), 4.33 (d, J=8.7 Hz, 1H), 4.11 (q, J=14.7 Hz, 1H), 4.00 (m, 2H), 3.89 (m, 2H), 3.82 (m, 2H), 3.72 (m, 2H), 3.59 (m, 2H), 3.45 (m, 4H), 3.10 (s, 3H), 2.88 (s, 3H), 2.49 (m, 2H), 2.36 (s, 3H), 2.33 (m, 2H), 1.91 (m, 2H), 1.72 (m, 2H), 1.42 (m, 2H); LC/MS 414.4 (M+1).

Example 24

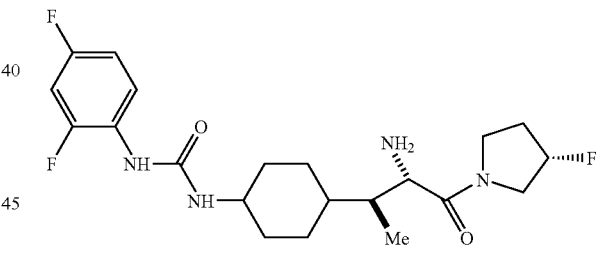

·CF₃CO₂H (2S,3S)-3-[4-({[(2,4-Difluorophenyl)amino]carbonyl}amino)cyclohexyl]-1-[(3S)-3-fluoropyrrolidin-1-yl]-1-oxobutan-2-aminium trifluoroacetate Step A: Benzyl (4-{(1S,2S)-2-[(tert-butoxycarbonyl)amino]-3-[(3S)-3-fluoropyrrolidin-1-yl]-1-methyl-3-oxopropyl}cyclohexyl)carbamate To a solution of Intermediate 12 (2.5 g, 6.1 mmol) in toluene (150 mL) was added triethylamine (1.3 mL, 9.2 mmol) and diphenylphosphoryl azide (2.1 mL, 9.2 mmol). The solution was heated to 110° C. for 90 min, then cooled to ambient temperature. To the solution was added benzyl alcohol (1.9 mL, 19 mmol), and the mixture was again heated to 110° C. for 36 h. The mixture was cooled to ambient temperature and diluted with 400 mL of ethyl acetate. The organic layer was washed with saturated aqueous sodium bicarbonate and brine, dried (magnesium sulfate) and concentrated in vacuo. Purification by silica gel chromatography (65% ethyl acetate in hexanes) afforded the title compound as a 2:1 mixture of cis and trans cyclohexyl diastereomers. This mixture was separated by chiral HPLC (Chiracel OD column, 10% ethanol in hexanes) to afford each pure diastereomer: The faster eluting diastereomer (major): ¹H NMR (500 MHz, CDCl₃): δ 7.35 (m, 5H), 5.33 (d, J=19.5 Hz, 1H), 5.23 (d, J=19.5 Hz, 1H), 5.10 (m, 3H), 4.99 (s, 2H), 4.41 (t, J=10 Hz, 1H), 4.28 (t, J=10 Hz, 1H), 3.91 (m, 8H), 3.73 (t, J=4.5 Hz, 1H), 3.57 (dd, J=3.5 Hz, J=14 Hz, 1H), 3.51 (m, 2H), 2.36 (m, 1H), 2.28 (m, 1H), 2.05 (m, 1H), 1.89 (m, 2H), 1.79 (m, 2H), 1.58 (m, 2H), 1.43 (s, 9H), 1.34 (m, 2H), 1.22 (d, J=6.0 Hz, 2H), 1.16 (m, 1H), 0.83 (d, J=7.0 Hz, 2H), 0.80 (d, J=7.0 Hz, 2H); LC/MS 406.2 (M+1-Boc). The slower eluting diastereomer (minor) ¹H NMR (500 MHz, CDCl₃): δ 7.35 (m, 5H), 5.34 (d, J=18.5 Hz, 1H), 5.23 (d, J=18.5 Hz, 1H), 5.10 (s, 2H), 5.06 (d, J=9.5 Hz, 2H), 4.64 (d, J=6.5 Hz, 2H), 4.38 (t, J=10 Hz, 1H), 4.26 (t, J=10 Hz, 1H), 3.88 (m, 8H), 3.76 (t, J=9.5 Hz, 1H), 3.58 (dd, J=3.5 Hz, J=14 Hz, 1H), 3.49 (m, 3H), 2.37 (m, 1H), 2.29 (m, 1H), 2.07 (m, 1H), 1.81 (m, 2H), 1.73 (m, 1H), 1.50 (m, 2H), 1.43 (s, 9H), 1.21 (m, 2H), 1.14 (m, 2H), 0.82 (d, J=7.0 Hz, 2H), 0.78 (d, J=7.0 Hz, 2H); LC/MS 406.2 (M+1-Boc).

Step B: tert-Butyl((1S,2S)-2-(4-aminocyclohexyl)-1-{[(3S)-3-fluoropyrrolidin-1-yl]carbonyl}propyl)carbamate To a solution of the slower eluting diastereomer of the material prepared in Step A (0.60 g, 1.2 mmol) in methanol (100 mL) was added 10% palladium on carbon (0.20 g). The mixture was placed under 3 atm of hydrogen gas for 3 h, then filtered through Celite. The solution was then concentrated in vacuo, affording the title compound as a clear oil. LC/MS 372.3 (M+H).

Step C: tert-Butyl((1S,2S)-2-[4-({[(2,4-difluorophenyl)amino]carbonyl}amino)cyclohexyl]-1-{[(3S)-3-fluoropyrrolidin-1-yl]carbonyl}propyl)carbamate To a solution of the material prepared in Step B (0.020 g, 0.054 mmol) in dichloromethane (2 mL) was added N,N-diisopropylethylamine (0.019 mL, 0.11 mmol) and 2,6-difluorophenylisocyanate (0.010 mL, 0.081 mmol). After 8 h at ambient temperature the reaction was diluted with ethyl acetate, and washed with saturated aqueous sodium bicarbonate and brine, dried (magnesium sulfate) and concentrated in vacuo. Purification by reverse phase HPLC (32%-70% acetonitrile in water) afforded the title compound as a while solid. LC/MS 427.2 (M+1-Boc).

Step D: (2S,3S)-3-[4-({[(2,4-Difluorophenyl)amino]carbonyl}amino)cyclohexyl]-1-[(3S)-3-fluoropyrrolidin-1-yl]-1-oxobutan-2-aminium trifluoroacetate To a solution of the material prepared in Step C (0.23 g, 0.48 mmol) in dichloromethane (3 mL) was added trifluoroacetic acid (1 mL). After 3 h at ambient temperature the reaction was concentrated in vacuo. Purification by reverse phase HPLC (20%-50% acetonitrile in water) afforded the title compound as a white solid. LC/MS 427.2 (M+H).

Example 25

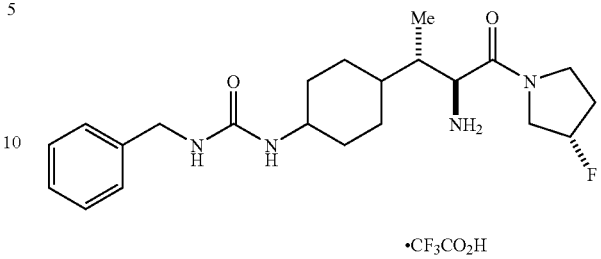

•CF₃CO₂H (2S,3S)-3-(4-{[(Benzylamino)carbonyl]amino}cyclohexyl)-1-[(3S)-3-fluoropyrrolidin-1-yl]-1-oxobutan-2-aminium trifluoroacetate The title compound was prepared from the slower eluting diastereomer of Step A in Example 24, using the procedures detailed in Steps B-D of Example 24. LC/MS 405.2 (M+1).

Example 26

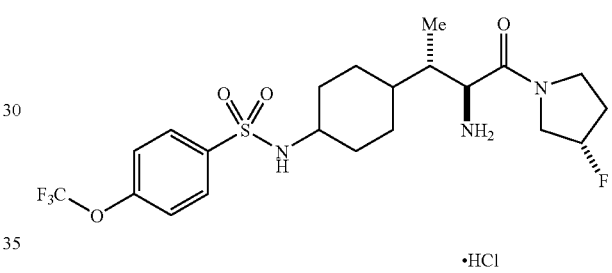

•HCl (2S,3S)-1-[(3S)-3-Fluoropyrrolidin-1-yl]-1-oxo-3-[4-({[4-(trifluoromethoxy)phenyl]sulfonyl}amino)cyclohexyl]butan-2-aminium chloride Step A: tert-Butyl {(1S,2S)-1-{[(3S)-3-fluoropyrrolidin-1-yl]carbonyl}-2-[4-({[4-(trifluoromethoxy)phenyl]sulfonyl}amino)cyclohexyl]propyl}carbamate To a solution of the material from Step B of Example 24 (32 mg, 0.085 mmol) in dichloromethane (2 mL) was added N,N-diisopropylethylamine (0.022 mL, 0.13 mmol), and 4-(trifluoromethoxy)-benzenesulfonyl chloride (0.034 mL, 0.094 mmol). After 2 h at ambient temperature the reaction was diluted with 100 mL of ethyl acetate and washed with saturated aqueous sodium bicarbonate and brine, dried (magnesium sulfate) and concentrated in vacuo. Purification by preparative thin layer chromatography (65% ethyl acetate in hexanes) afforded the title compound as a white solid. LC/MS 496.1 (M+1-Boc).

Step B: (2S,3S)-1-[(3S)-3-Fluoropyrrolidin-1-yl]-1-oxo-3-[4-({[4-(trifluoromethoxy)phenyl]sulfonyl}amino)cyclohexyl]butan-2-aminium chlo To the solid material prepared in Step A (0.028 g, 0.047 mmol) was added a 4 M solution of hydrogen chloride in dioxane (2 mL). After 2 h at ambient temperature the reaction was concentrated in vacuo, affording the title compound as a white solid. ¹H NMR (CD₃OD): δ 7.99 (d, J=5.5 Hz, 2H), 7.47 (d, J=8.0 Hz, 2H), 5.42 (s, 0.5H as a single rotamer), 5.36 (t, J=3.0 Hz, 0.5H as a single rotamer), 5.31 (s, 0.5H as a single rotamer), 5.26 (t, J=3.0 Hz, 0.5H as a single rotamer), 4.01 (d, J=9.0 Hz, 1H), 3.96 (d, J=9.0 Hz, 1H), 3.76 (m, 6H), 3.68 (s, 3H), 3.49 (m, 2H), 3.03 (m, 2H), 2.20 (m, 3H), 1.94 (m, 1H), 1.83 (m, 2H), 1.55 (m, 2H), 1.32 (m, 2H), 1.15 (m, 2H), 0.89 (dd, J=2.0 Hz, J=7.0 Hz, 3H); LC/MS 496.1 (M+1).

Following the procedures outlined in Example 26, and using the appropriately R² substituted intermediate, Examples 27-29 listed in Table 5 were prepared.

TABLE 5

| Example | R³ | R² | MS (M + 1) |
|---|---|---|---|
| 27 | 2,4-difluorophenylsulfonamide | Me | 448.1 |
| 28 | 2,4-difluorophenylsulfonamide | CONMe₂ | 505.2 |
| 29 | 4-(trifluoromethoxy)phenylsulfonamide | CONMe₂ | 553.2 |

Example 30

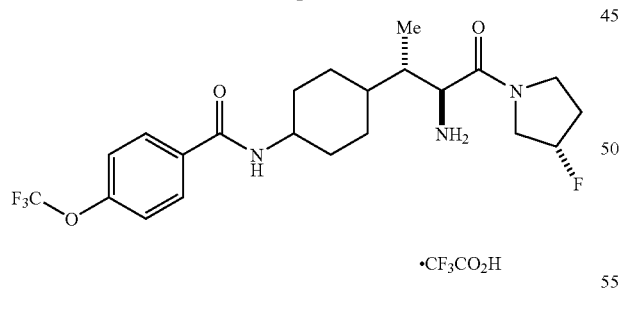

•CF₃CO₂H (2S,3S)-1-[(3S)-3-Fluoropyrrolidin-1-yl]-1-oxo-3-(4-{[4-(trifluoromethoxy)benzoyl]amino}cyclohexyl)butan-2-aminium trifluoroacetate Step A: tert-Butyl[(1S,2S)-1-{[(3S)-3-fluoropyrrolidin-1-yl]carbonyl}-2-(4-{[4-(trifluoromethoxy)benzoyl]amino}cyclohexyl)propyl]carbamate To a solution of the material prepared in Step B of Example 24 (0.020 g, 0.054 mmol) in DMF (2 mL) was added 4-(trifluoromethoxy)benzoic acid (0.0090 g, 0.059 mmol), HOAT (0.0080 g, 0.059 mmol), N,N-diisopropylethylamine (0.047 mL, 0.27 mmol) and HATU (0.022 g, 0.059 mmol). After 24 h at ambient temperature the reaction was diluted with 100 mL of ethyl acetate and washed with 100 mL of 0.5 M aqueous sodium bicarbonate. The organic layer was washed with brine, dried (magnesium sulfate) and concentrated in vacuo. Purification by reverse phase HPLC (30%-60% acetonitrile in H₂0 gradient) afforded the title compound as a white solid. LC/MS 506.3 (M+1).

Step B: (2S,3S)-1-[(3S)-3-Fluoropyrrolidin-1-yl]-1-oxo-3-(4-{[4-(trifluoromethoxy)benzoyl]amino}cyclohexyl)butan-2-aminium trifluoroacetate To a solution of the material prepared in Step A (0.017 g, 0.036 mmol) in dichloromethane (3 mL) was added trifluoroacetic acid (1 mL). After 3 h at ambient temperature the reaction was concentrated in vacuo, affording the title compound as a white solid. LC/MS 406.3 (M+1).

Example 31

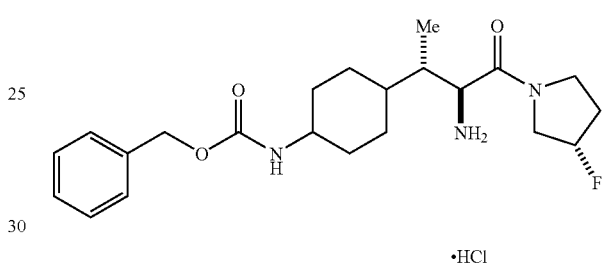

•HCl (2S,3S)-3-(4-{[(Benzyloxy)carbonyl]amino}cyclohexyl)-1-[(3S)-3-fluoropyrrolidin-1-yl]-1-oxobutan-2-aminium chloride Step A: (2S,3S)-3-(4-{[(Benzyloxy)carbonyl]amino}cyclohexyl)-1-[(3S)-3-fluoropyrrolidin-1-yl]-1-oxobutan-2-aminium chloride To the slower eluting diastereomer from Step B of Example 24 (0.020 g, 0.040 mmol) was added a 4 M solution of hydrogen chloride in dioxane (1 mL). After 2 h at ambient temperature the reaction was concentrated in vacuo, affording the title compound as a white solid. LC/MS 406.2 (M+1).

Example 32

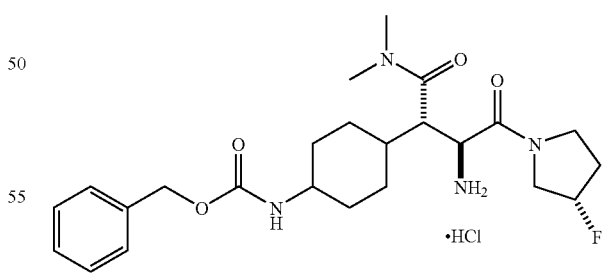

•HCl (2S,3S)-3-(4-{[(Benzyloxy)carbonyl]amino}cyclohexyl)-4-(dimethylamino)-1-[(3S)-3-fluoropyrrolidin-1-yl]-1,4-dioxobutan-2-aminium trifluoroacetate The title compound was prepared from Intermediate 15 in a similar fashion to the synthesis of Example 31. LC/MS 463.2 (M+1).

Example 33

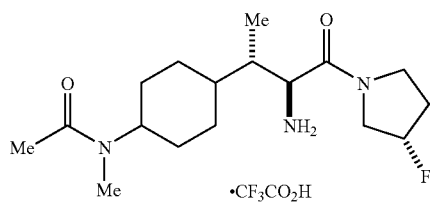

(2S,3S)-3-{4-[Acetyl(methyl)amino]cyclohexyl}-1-
[(3S)-3-fluoropyrrolidin-1-yl]-1-oxobutan-2-
aminium trifluoroacetate Step A: N-Benzyl-4-{(1S,2S)-2-[(tert-butoxycarbonyl)amino]-3-[(3S)-3-fluoropyrrolidin-1-yl]-1-methyl-3-oxopropyl}cyclohexanaminium trifluoroacetate To a solution of the material prepared in Step B of Example 24 (0.23 g, 0.61 mmol) in dichloroethane (7 mL) was added benzaldehyde (0.068 mL, 0.67 mmol) and sodium triacetoxyborohydride (0.19 g, 0.92 mmol). After 90 min at ambient temperature the reaction was diluted with 100 mL of dichloromethane and washed with saturated aqueous sodium bicarbonate. The organic layer was dried (anhydrous sodium sulfate) and concentrated in vacuo. Purification by reverse phase HPLC (15%-60% acetonitrile in water gradient) afforded the title compound as a white solid. LC/MS 462.5 (M+1).

Step B: tert-Butyl((1S,2S)-2-{4-[benzyl(methyl)amino]cyclohexyl}-1-{[(3S)-3-fluoropyrrolidin-1-yl]carbonyl}propyl)carbamate To a solution of the material prepared in Step A (0.25 g, 0.54 mmol) in methanol (6 mL) was added a 37% aqueous solution of formaldehyde (0.10 mL, 1.62 mmol), followed by sodium triacetoxyborohydride (0.46 g, 2.16 mmol). After 3 h at ambient temperature the reaction was diluted with 100 mL of ethyl acetate, and the organic layer was washed with saturated aqueous sodium bicarbonate and brine, dried (magnesium sulfate) and concentrated in vacuo, affording the title compound as a clear oil. This material was used without further purification. LC/MS 476.5 (M+1).

Step C: tert-Butyl {(1S,2S)-1-{-[(3S)-3-fluoropyrrolidin-1-yl]carbonyl}-2-[4-(methylamino)cyclohexyl]propyl}carbamate To a solution of the material prepared in Step B (0.18 g, 0.37 mmol) in methanol (100 mL) was added palladium(II) hydroxide (0.10 g). The mixture was placed under 3 atm of hydrogen at ambient temperature for 6 h, then filtered through Celite. The solution was concentrated in vacuo, affording the title compound as a clear oil. This material was used without further purification. LC/MS 386.3 (M+1).

Step D: tert-Butyl((1S,2S)-2-{4-[acetyl(methyl)amino]cyclohexyl}-1-{[(3S)-3-fluoropyrrolidin-1-yl]carbonyl}propyl)carbamate To a solution of the material prepared in Step C (0.020 g, 0.052 mmol) in DMF (1 mL) was added acetic acid (0.003 mL, 0.06 mmol), N,N-diisopropylethylamine (0.045 mL, 0.26 mmol), HOAT (0.095 mL of a 0.6 M DMF solution, 0.095 mmol), and HATU (0.022 g, 0.095 mmol). After 3 h at ambient temperature the reaction was diluted with 100 mL of ethyl acetate and washed with 0.5 M aqueous sodium bicarbonate. The organic layer was washed with brine, dried (magnesium sulfate), and concentrated in vacuo. Purification by reverse phase liquid chromatography (20%-60% acetonitrile in water gradient) afforded the title compound as a white solid. LC/MS 450.3 (M+Na).

Step E: (2S,3S)-3-{4-[Acetyl(methyl)amino]cyclohexyl}-1-[(3S)-3-fluoropyrrolidin-1-yl]-1-oxobutan-2-aminium trifluoroacetate To a solution of the material prepared in Step D (0.012 g, 0.028 mmol) in dichloromethane (3 mL) was added trifluoroacetic acid (1 mL). After 3 h at ambient temperature the reaction was concentrated in vacuo, affording the title compound as a white solid. $^1$H NMR (500 MHz, CD$_3$OD): δ 5.41 (s, 0.5H as a single rotamer), 5.36 (s, 0.5H as a single rotamer), 5.31 (0.5H as a single rotamer), 5.26 (0.5H as a single rotamer), 4.28 (m, 1H), 4.06 (dd, J=5.5 Hz, J=9.0 Hz, 1H), 4.00 (dd, J=5.5 Hz, J=9.0 Hz, 1H), 3.78 (m, 6H), 3.64 (m, 2H), 3.51 (m, 1H), 2.90 (s, 1.5H as a single rotamer), 2.79 (s, 1.5H as a single rotamer), 2.31 (m, 2H), 2.13 (s, 3H), 2.07 (s, 3H), 1.98 (m, 2H), 1.70 (m, 6H), 1.30 (m, 2H), 0.93 (m, 3H); LC/MS 328.3 (M+1).

Following the procedures outlined in Example 33, and using the appropriately R$^2$ substituted and X substituted intermediates, Examples 34-48 listed in Table 6 were prepared.

TABLE 6

| Example | R$^3$ | R$^2$ | X | MS (M + 1) |
|---|---|---|---|---|
| 34 | ![cyclopropyl-C(=O)-N(Me)-] | Me | (S)-CHF | 354.2 |

TABLE 6-continued

| Example | R³ | R² | X | MS (M + 1) |
|---|---|---|---|---|
| 35 | 3-F-C₆H₄-C(O)-N(Me)- | Me | (S)-CHF | 408.4 |
| 36 | 4-(CF₃O)-C₆H₄-C(O)-N(Me)- | Me | (S)-CHF | 474.3 |
| 37 | 4-(CH₃O)-C₆H₄-C(O)-N(Me)- | Me | (S)-CHF | 420.1 |
| 38 | 3-(CF₃)-C₆H₄-C(O)-N(Me)- | Me | (S)-CHF | 458.3 |
| 39 | 4-F-C₆H₄-C(O)-N(Me)- | Me | (S)-CHF | 408.1 |
| 40 | 3-(CF₃O)-C₆H₄-C(O)-N(Me)- | Me | (S)-CHF | 474.3 |
| 41 | pyridin-3-yl-C(O)-N(Me)- | Me | (S)-CHF | 391.4 |
| 42 | pyridin-4-yl-C(O)-N(Me)- | Me | (S)-CHF | 391.4 |

TABLE 6-continued

| Example | R³ | R² | X | MS (M + 1) |
|---|---|---|---|---|
| 43 | Me-C(O)-N(Me)- | CONMe₂ | (S)-CHF | 407.4 (M + Na) |
| 44 | Me-C(O)-N(Me)- | CONMe₂ | CF₂ | 403.5 |
| 45 | Me-S(O)₂-N(Me)- | Me | (S)-CHF | 364.3 |
| 46 | BnO-C(O)-N(Me)- | Me | (S)-CHF | 420.4 |
| 47 | BnNH-C(O)-N(Me)- | Me | (S)-CHF | 419.4 |
| 48 | (2,4-F₂-C₆H₃)NH-C(O)-N(Me)- | Me | (S)-CHF | 441.5 |

Example of a Pharmaceutical Formulation

As a specific embodiment of an oral pharmaceutical composition, a 100 mg potency tablet is composed of 100 mg of any of the compounds of the present invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations of differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula I:

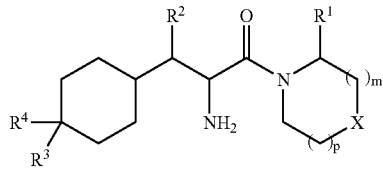

or a pharmaceutically acceptable salt thereof; wherein
each n is independently 0, 1, or 2;
m and p are independently 0 or 1;
X is $CH_2$, S, CHF or $CF_2$;
$R^1$ is hydrogen or cyano;
$R^2$ is selected from the group consisting of
  $C_{1-10}$ alkyl, wherein alkyl is unsubstituted or substituted with one to five substituents independently selected from halogen or hydroxy,
  $C_{2-10}$ alkenyl, wherein alkenyl is unsubstituted or substituted with one to five substituents independently selected from halogen or hydroxy,
  $(CH_2)_n$-aryl, wherein aryl is unsubstituted or substituted with one to five substituents independently selected hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$-heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$-heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$—$C_{3-6}$ cycloalkyl, wherein cycloalkyl is unsubstituted or substituted with one to three substituents independently selected from halogen, hydroxy, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$COOH,
  $(CH_2)_n$COO$C_{1-6}$ alkyl,
  $(CH_2)_n$CONR$^5$R$^6$, wherein $R^5$ and $R^6$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
    or $R^5$ and $R^6$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and
  wherein any individual methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
each $R^3$ is independently selected from the group consisting of
  halogen,
  cyano,
  hydroxy,
  phenyloxy, unsubstituted or substituted with one to five substituents independently selected from halogen, hydroxy, $CO_2H$, CONR$^5$R$^6$, cyano, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens;
  $C_{1-6}$ alkyl, wherein alkyl is unsubstituted or substituted with one to five halogens,
  $C_{1-6}$ alkoxy, wherein alkoxy is unsubstituted or substituted with one to five halogens,
  $(CH_2)_n$—NR$^5$R$^6$,
  $(CH_2)_n$—CONR$^5$R$^6$,
  $(CH_2)_n$—OCONR$^5$R$^6$,
  $(CH_2)_n$—SO$_2$NR$^5$R$^6$,
  $(CH_2)_n$—SO$_2$R$^7$,
  $(CH_2)_n$—NR$^8$SO$_2$R$^7$,
  $(CH_2)_n$—NR$^8$CONR$^5$R$^6$,
  $(CH_2)_n$—NR$^8$COR$^8$,
  $(CH_2)_n$—NR$^8$CO$_2$R$^7$,
  $(CH_2)_n$—COOH,
  $(CH_2)_n$—COO$C_{1-6}$ alkyl,
  $(CH_2)_n$-aryl, wherein aryl is unsubstituted or substituted with one to five substituents independently selected from halogen, hydroxy, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
  $(CH_2)_n$-heteroaryl, wherein heteroaryl is unsubstituted or substituted with one to three substituents independently selected from hydroxy, halogen, $CO_2H$, $C_{1-6}$ alkyloxycarbonyl, aryl, $C_{1-6}$ alkyl, $C_{3-6}$ cycloalkyl, and $C_{1-6}$ alkoxy, wherein aryl, alkyl and alkoxy are unsubstituted or substituted with one to five halogens,
  $(CH_2)_n$-heterocyclyl, wherein heterocyclyl is unsubstituted or substituted with one to three substituents independently selected from oxo, hydroxy, halogen, $CO_2H$, $C_{1-6}$ alkyloxycarbonyl, aryl, $C_{1-6}$ alkyl, $C_{3-6}$ cycloalkyl, and $C_{1-6}$ alkoxy, wherein aryl, alkyl and alkoxy are unsubstituted or substituted with one to five halogens,
  $(CH_2)_n$—$C_{3-6}$ cycloalkyl, wherein cycloalkyl is unsubstituted or substituted with one to three substituents independently selected from halogen, hydroxy, aryl, $C_{1-6}$ alkyl, and $C_{1-6}$ alkoxy, wherein aryl, alkyl and alkoxy are unsubstituted or substituted with one to five halogens,
  wherein any individual methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;

$R^4$ is selected from the group consisting of:
- hydrogen,
- hydroxy,
- halogen,
- cyano,
- $C_{1-6}$ alkyl, wherein alkyl is unsubstituted or substituted with one to five halogens, and
- $C_{1-6}$ alkoxy, wherein alkoxy is unsubstituted or substituted with one to five halogens;

$R^5$ and $R^6$ are each independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or $R^5$ and $R^6$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens;

$R^7$ is independently selected from the group consisting of $(CH_2)_n$-heteroaryl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein heteroaryl, phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens; and each $R^8$ is hydrogen or $R^7$.

2. The compound of claim 1 wherein the carbon atom marked with an * has the stereochemical configuration as depicted in formula Ia:

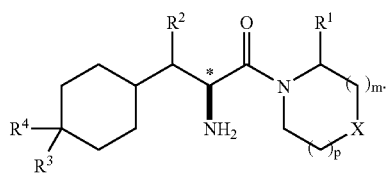
(Ia)

3. The compound of claim 2 wherein the carbon atom marked with an * and the carbon atom attached to $R^1$ marked with an ** have the stereochemical configurations as depicted in formula Ib:

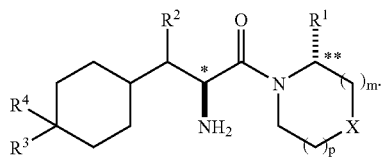
(Ib)

4. The compound of claim 3 wherein the carbon atom marked with an *, the carbon atom attached to $R^1$ marked with an , and the carbon atom attached to $R^2$ marked with an * have the stereochemical configurations as depicted in formula Ic:

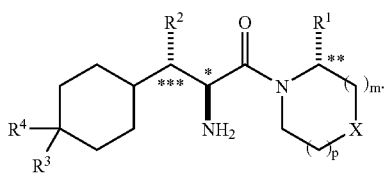
(Ic)

5. The compound of claim 1 wherein m is 1 and p is 0 as depicted in formula Id:

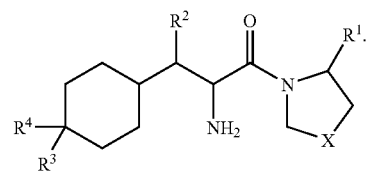
(Id)

6. The compound of claim 5 wherein the carbon atom marked with an * and the carbon atom attached to $R^1$ marked with an ** have the stereochemical configurations as depicted in formula Ie:

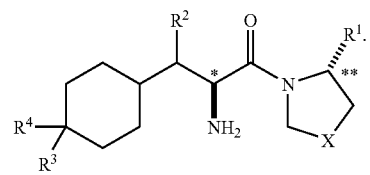
(Ie)

7. The compound of claim 6 wherein the carbon atom marked with an *, the carbon atom attached to $R^1$ marked with an , and the carbon atom attached to $R^2$ marked with an * have the stereochemical configurations as depicted in formula If:

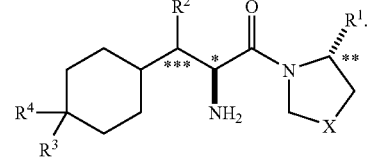
(If)

8. The compound of claim 7 wherein $R^1$ is hydrogen; $R^4$ is hydrogen or hydroxy; and X is CHF or $CF_2$.

9. The compound of claim 1 wherein $R^2$ is selected from the group consisting of:
  $C_{1-3}$ alkyl, wherein alkyl is unsubstituted or substituted with one to five substituents independently selected from halogen or hydroxy,
  $CH_2$—$C_{3-6}$ cycloalkyl,
  COOH,
  $COOC_{1-6}$ alkyl, and
  $CONR^5R^6$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
    or $R^5$ and $R^6$ together with the nitrogen atom to which they are attached form a heterocyclic ring selected from pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

10. The compound of claim 9 wherein $R^2$ is selected from the group consisting of:
  methyl,
  ethyl,
  $CH_2$-cyclopropyl,
  COOH,
  COOMe,
  COOEt,
  $CONMe_2$,
  $CONH_2$,
  CONHMe,
  CONHEt,
  pyrrolidin-1-ylcarbonyl,
  azetidin-1-ylcarbonyl, and
  [(tetrazol-5-yl)amino]carbonyl.

11. The compound of claim 1 wherein $R^3$ is selected from the group consisting of:
  phenyloxy, unsubstituted or substituted with one to five substituents independently selected from halogen, hydroxy, $CONR^5R^6$, cyano,
    $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens;
  $NR^5R^6$,
  $CONR^5R^6$,
  $OCONR^5R^6$,
  $NR^8SO_2R^7$,
  $NR^8CONR^5R^6$,
  $NR^8COR^8$,
  $NR^8CO_2R^7$,
  $(CH_2)_n$—$COOC_{1-6}$ alkyl,
  aryl, wherein aryl is unsubstituted or substituted with one to five substituents independently selected from halogen, hydroxy, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
  heteroaryl, wherein heteroaryl is unsubstituted or substituted with one to three substituents independently selected from hydroxy, halogen, $CO_2H$, $C_{1-6}$ alkyloxycarbonyl, aryl, $C_{1-6}$ alkyl, $C_{3-6}$ cycloalkyl, and $C_{1-6}$ alkoxy, wherein aryl, alkyl and alkoxy are unsubstituted or substituted with one to five halogens,
  heterocyclyl, wherein heterocyclyl is unsubstituted or substituted with one to three substituents independently selected from oxo, hydroxy, halogen, $CO_2H$, $C_{1-6}$ alkyloxycarbonyl, aryl, $C_{1-6}$ alkyl, $C_{3-6}$ cycloalkyl, and $C_{1-6}$ alkoxy, wherein aryl, alkyl and alkoxy are unsubstituted or substituted with one to five halogens,
  wherein any methylene ($CH_2$) carbon atom in $R^3$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens.

12. The compound of claim 11 wherein $R^2$ is selected from the group consisting of:
  methyl,
  ethyl,
  $CH_2$-cyclopropyl,
  COOH,
  COOMe,
  COOEt,
  $CONMe_2$,
  $CONH_2$,
  CONHMe,
  CONHEt,
  pyrrolidin-1-ylcarbonyl,
  azetidin-1-ylcarbonyl, and
  [(tetrazol-5-yl)amino]carbonyl.

13. The compound of claim 1 which is selected from the group consisting of:

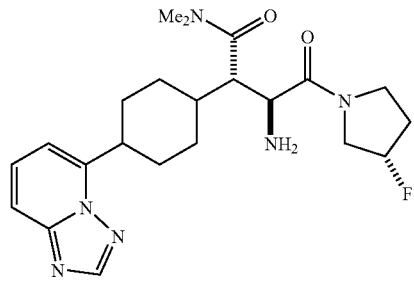

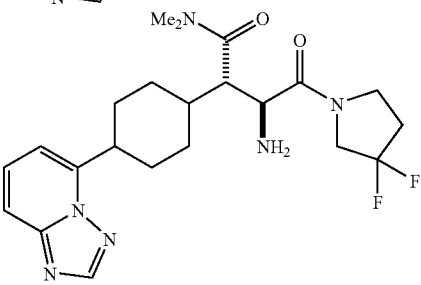

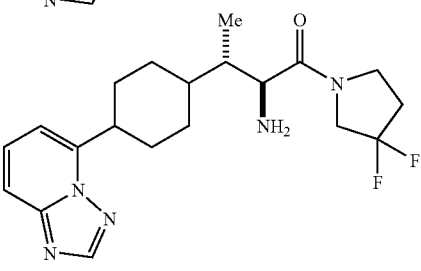

-continued
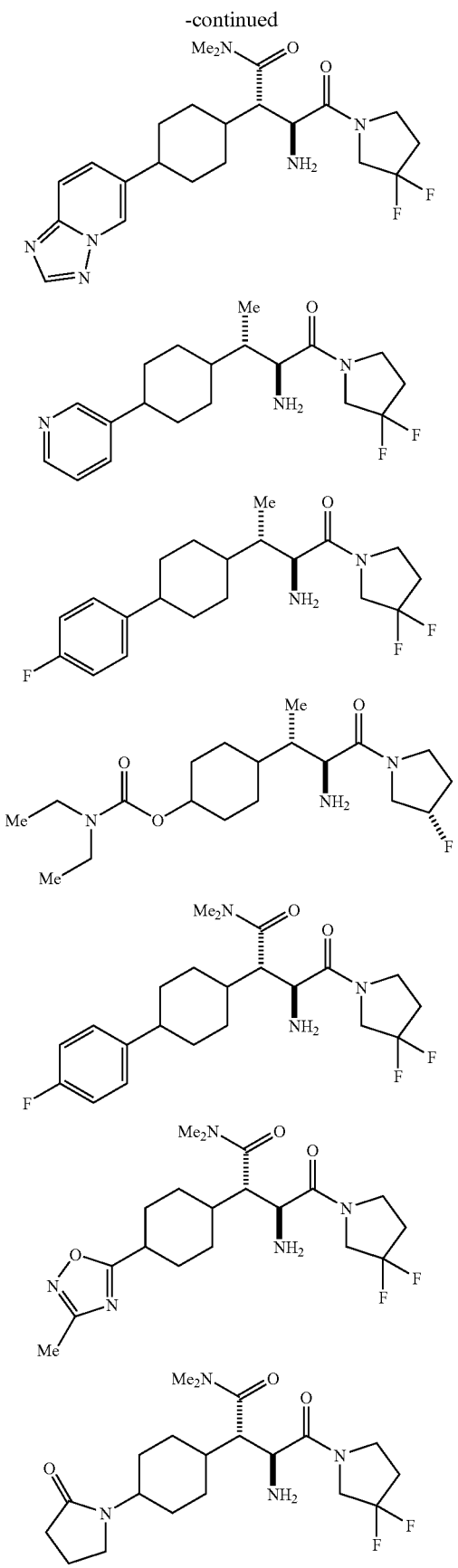
-continued
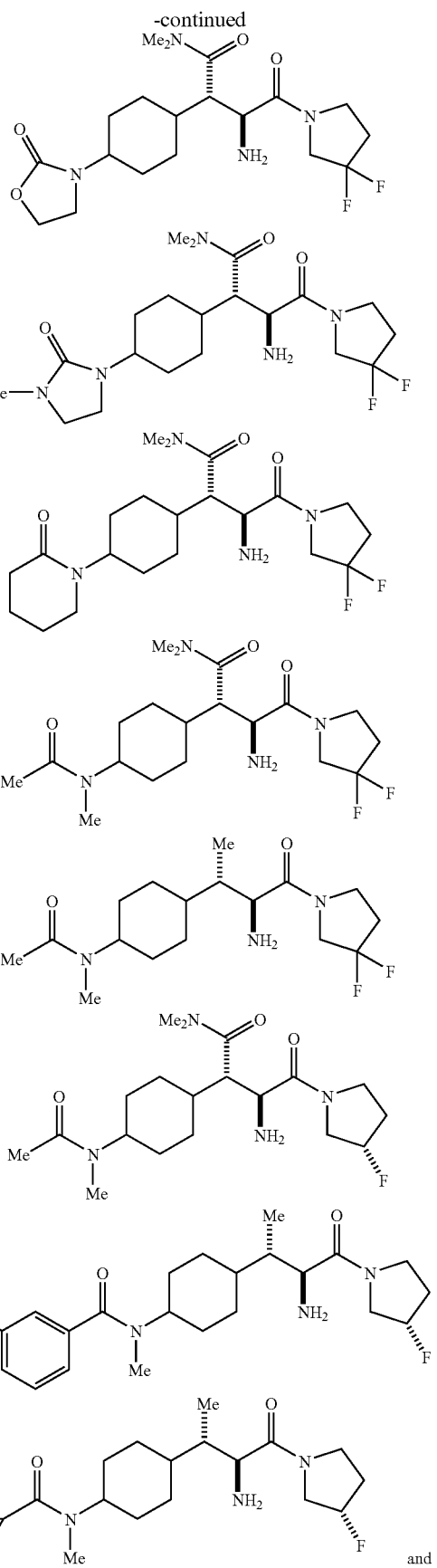
and

-continued

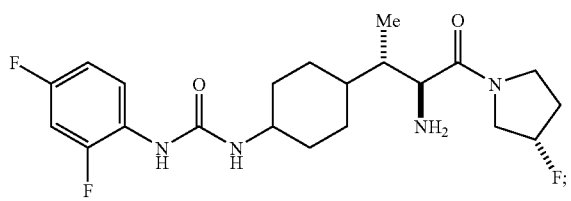

or a pharmaceutically acceptable salt thereof.

14. A pharmaceutical composition which comprises a compound of claim 1 and a pharmaceutically acceptable carrier.

15. A method for treating non-insulin dependent (Type 2) diabetes in a mammal in need thereof which comprises the administration to the mammal of a therapeutically effective amount of a compound of claim 1.

16. A method for treating hyperglycemia in a mammal in need thereof which comprises the administration to the mammal of a therapeutically effective amount of a compound of claim 1.

* * * * *